US010435676B2

(12) United States Patent
Champion et al.

(10) Patent No.: US 10,435,676 B2
(45) Date of Patent: Oct. 8, 2019

(54) VARIANTS OF TERMINAL DEOXYNUCLEOTIDYL TRANSFERASE AND USES THEREOF

(71) Applicant: DNA Script, Paris (FR)

(72) Inventors: Elise Champion, Paris (FR); Mikhael Soskine, Franconville (FR); Thomas Ybert, Paris (FR); Marc Delarue, Versailles (FR)

(*) Notice: Subject to any disclaimer, the term of this patent is extended or adjusted under 35 U.S.C. 154(b) by 0 days.

(21) Appl. No.: 16/242,904

(22) Filed: Jan. 8, 2019

(65) Prior Publication Data
US 2019/0211315 A1 Jul. 11, 2019

(30) Foreign Application Priority Data
Jan. 8, 2018 (EP) .................................. 18305006

(51) Int. Cl.
C12N 11/00 (2006.01)
C12N 9/12 (2006.01)

(52) U.S. Cl.
CPC .................................. C12N 9/1264 (2013.01)

(58) Field of Classification Search
CPC .......................... C12P 19/34; C12Y 207/07031
USPC ................................................. 435/174, 193
See application file for complete search history.

(56) References Cited

U.S. PATENT DOCUMENTS

| 4,448,883 | A | 5/1984 | Case |
| 4,772,691 | A | 9/1988 | Herman |
| 5,436,143 | A | 7/1995 | Hyman |
| 5,516,664 | A | 5/1996 | Hyman |
| 5,602,000 | A | 2/1997 | Hyman |
| 5,656,745 | A | 8/1997 | Bischofberger |
| 5,744,595 | A | 4/1998 | Srivastava |
| 5,763,594 | A | 6/1998 | Hiatt |
| 5,808,045 | A | 9/1998 | Hiatt |
| 5,872,244 | A | 2/1999 | Hiatt |
| 5,917,031 | A | 6/1999 | Miura |
| 5,935,527 | A | 8/1999 | Andrus |
| 5,990,300 | A | 11/1999 | Hiatt |
| 6,214,987 | B1 | 4/2001 | Hiatt |
| 6,232,465 | B1 | 5/2001 | Hiatt |
| 6,623,929 | B1 | 9/2003 | Densham |
| 6,777,189 | B2 | 8/2004 | Wei |
| 7,057,026 | B2 | 1/2006 | Barnes |
| 7,078,499 | B2 | 7/2006 | Odedra |
| 7,125,671 | B2 | 10/2006 | Sood |
| 7,270,951 | B1 | 9/2007 | Stemple |
| 7,407,757 | B2 | 8/2008 | Brenner |
| 7,494,797 | B2 | 2/2009 | Mueller |
| 7,544,794 | B1 | 6/2009 | Benner |
| 7,939,259 | B2 | 5/2011 | Kokoris |
| 8,034,923 | B1 | 10/2011 | Benner |
| 8,212,020 | B2 | 7/2012 | Benner |
| 8,263,335 | B2 | 9/2012 | Carr |
| 8,674,086 | B2 | 3/2014 | Liu |
| 8,808,988 | B2 | 8/2014 | Zhao |
| 8,808,989 | B1 | 8/2014 | Efcavitch |
| 9,896,709 | B2 | 2/2018 | Makarov |
| 10,059,929 | B2 | 8/2018 | Efcavitch |
| 2014/0363851 | A1 | 12/2014 | Efcavitch |
| 2014/0363852 | A1 | 12/2014 | Efcavitch |
| 2018/0023108 | A1 | 1/2018 | Chen |

FOREIGN PATENT DOCUMENTS

| WO | WO2016/064880 | 4/2016 |
| WO | 2016/128731 A1 | 8/2016 |
| WO | 2016/128731 A4 | 8/2016 |
| WO | 2017/216472 A2 | 12/2017 |
| WO | 2017/216472 A3 | 12/2017 |
| WO | WO/2018/215803 | 11/2018 |

OTHER PUBLICATIONS

Accession No. A4PCE2, May 15, 2007.*
Database EPO Proteins, "Sequence 8 from Patent WO2016128731", XP002779827, Oct. 5, 2016.
Database UniProt, SubName: Full=DNA nucleotidylexotransferase isoform X1 {EC0:0000313:RefSeq:XP_008057295.1}, XP002779838, May 10, 2017.
Delarue et al. (2002) "Crystal structures of a template-independent DNA polymerase: murine terminal deoxynucleotidyltransferase" The EMBO Journal 21(3): 427-439.
Yang et al. (1994) "Mutational Analysis of Residues in the Nucleotide Binding Domain of Human Terminal Deoxynucleotidyl Transferase" The Journal of Biological Chemistry 269(16): 11859-11868.
Aoufouchi et al, "Two novel human and mouse DNA polymerases of the polX family," Nucleic Acids Research, 28(18): 3684-3693 (2000).
Beabealashvilli et al, "Nucleoside 5'-triphosphates modified at sugar residues as substrates for calf thymus terminal deoxynucleotidyl transferase and for AMV reverse transcriptase," Biochim. Biophys. Acta., 868(2-3): 136-144 (1986).
Bentoila et al, "The two isoforms of mouse terminal deoxynucleotidyl transferase differ in both the ability to add N regions and subcellular localization," The EMBO Journal, 14(17): 4221-4229 (1995).
Boule et al, "High-level expression of murine terminal deoxynucleotidyl transferase in *Escherichia coli* grown at low temperature and overexpressing argU tRNA," Molecular Biotechnology, 10: 199-208 (1998).
Dominguez et al, "DNA polymerase mu (Polμ), homologous to TdT, could act as a DNA mutator in eukaryotic cells," The EMBO Journal, 19(17): 1731-1742 (2000).

(Continued)

*Primary Examiner* — Tekchand Saidha
(74) *Attorney, Agent, or Firm* — Edward J. Baba; Bozicevic, Field & Francis LLP

(57) ABSTRACT

The present invention relates to a variant of Terminal deoxynucleotidyl Transferase (TdT) which (i) comprises the amino acid sequence as set forth in SEQ ID N° 2 or a functionally equivalent sequence, with at least an amino acid substitution at position corresponding to residue C302 or functionally equivalent residue, wherein the position is numbered by reference to the amino acid sequence set forth in SEQ ID N° 1, (ii) is able to synthesize a nucleic acid fragment without template and (iii) is able to incorporate a modified nucleotide into the nucleic fragment.

11 Claims, 2 Drawing Sheets

Specification includes a Sequence Listing.

(56) References Cited

OTHER PUBLICATIONS

Flickinger et al, "Differential incorporation of biotinylated nucleotides by terminal deoxynucleotidyl transferase," Nucleic Acids Research, 20(9): 2382 (1992).
Gouge et al, "Structures of intermediates along the catalytic cycle of terminal deoxynucleotidyltransferase: dynamical aspects of the two-metal ion mechanism," J. Mol. Biol., 425: 4334-4352 (2013).
International Search Report from PCT International Application No. PCT/FR2017/051519 dated Jan. 18, 2018.
International Search Report from PCT International Application No. PCT/EP2019/050334 dated Feb. 22, 2019.
Koiwai et al, "Isolation and characterization of bovine and mouse terminal deoxynucleotidyltransferase cDNAS expressible in mammalian cells," Nucleic Acids Research, 14(14): 5777-5792 (1986).
Michelson et al, "Characterization of the homopolymer tailing reaction catalyzed by terminal deoxynucleotidyl transferase," J. Biol. Chem., 257(24): 14773-14782 (1982).
Motea et al, "Terminal deoxynucleotidyl transferase: The story of a misguided DNA polymerase," Biochim Biophys Acta, 1804(5): 1151-1166 (2010).
Romain et al, "Conferring a template-dependent polymerase activity to terminal deoxynucleotidyltransferase by mutations in the Loop1 region," Nucleic Acids Research, 37(14): 4642-4656 (2009).
Schmitz et al, "Solid-phase enzymatic synthesis of oligonucleotides," Organic Lett., 1(11): 1729-1731 (1999).
Schott et al, "Single-step elongation of oligodeoxynucleotides using terminal deoxynucleotidyl transferase," Eur. J. Biochem., 143: 613-620 (1984).
Troshchynsky et al, "Functional analyses of polymorphic variants of human terminal deoxynucleotidyl transferase," Genes and Immunity, 16: 388-398 (2015).
Ud-Dean, "A theoretical model for template-free synthesis of long DNA sequence," Syst. Synth. Biol., 2: 67-73 (2008).
Written Opinion from PCT International Application No. PCT/FR2017/051519 dated Jan. 18, 2018.
Yamtich et al, "DNA polymerase family X: function, structure, and cellular roles," Biochim. Biophys. Acta., 1804(5): 1136-1150 (2010).
Yang et al, "T-cell specific avian TdT: characterization of the cDNA and recombinant ezyme," Nucleic Acids Research, 23(11): 2041-2048 (1995).

* cited by examiner

SEQUENCE LISTING

<160> NUMBER OF SEQ ID NOS: 9

<210> SEQ ID NO 1
<211> LENGTH: 510
<212> TYPE: PRT
<213> ORGANISM: artificial sequence
<220> FEATURE:
<223> OTHER INFORMATION: murine TdT

<400> SEQUENCE: 1

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
            20                  25                  30

Arg Asp Leu Val Leu Phe Ile Leu Glu Lys Lys Met Gly Thr Thr Arg
        35                  40                  45

Arg Ala Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
            100                 105                 110

Ala Gly Lys Pro Val Glu Met Met Gly Arg His Gln Leu Val Val Asn
        115                 120                 125

Arg Asn Ser Ser Pro Ser Pro Val Pro Gly Ser Gln Asn Val Pro Ala
    130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

Arg Ala Ser Ser Val Leu Lys Ser Leu Pro Phe Pro Ile Thr Ser Met
        195                 200                 205

Lys Asp Thr Glu Gly Ile Pro Cys Leu Gly Asp Lys Val Lys Ser Ile
    210                 215                 220

Ile Glu Gly Ile Ile Glu Asp Gly Glu Ser Ser Glu Ala Lys Ala Val
225                 230                 235                 240

Leu Asn Asp Glu Arg Tyr Lys Ser Phe Lys Leu Phe Thr Ser Val Phe
                245                 250                 255

Gly Val Gly Leu Lys Thr Ala Glu Lys Trp Phe Arg Met Gly Phe Arg
            260                 265                 270

Thr Leu Ser Lys Ile Gln Ser Asp Lys Ser Leu Arg Phe Thr Gln Met
        275                 280                 285

Gln Lys Ala Gly Phe Leu Tyr Tyr Glu Asp Leu Val Ser Cys Val Asn
    290                 295                 300

Arg Pro Glu Ala Glu Ala Val Ser Met Leu Val Lys Glu Ala Val Val
305                 310                 315                 320

Thr Phe Leu Pro Asp Ala Leu Val Thr Met Thr Gly Gly Phe Arg Arg
                325                 330                 335

Gly Lys Met Thr Gly His Asp Val Asp Phe Leu Ile Thr Ser Pro Glu
            340                 345                 350

```
Ala Thr Glu Asp Glu Glu Gln Gln Leu Leu His Lys Val Thr Asp Phe
            355                 360                 365

Trp Lys Gln Gln Gly Leu Leu Leu Tyr Cys Asp Ile Leu Glu Ser Thr
    370                 375                 380

Phe Glu Lys Phe Lys Gln Pro Ser Arg Lys Val Asp Ala Leu Asp His
385                 390                 395                 400

Phe Gln Lys Cys Phe Leu Ile Leu Lys Leu Asp His Gly Arg Val His
                405                 410                 415

Ser Glu Lys Ser Gly Gln Gln Glu Gly Lys Gly Trp Lys Ala Ile Arg
                420                 425                 430

Val Asp Leu Val Met Cys Pro Tyr Asp Arg Arg Ala Phe Ala Leu Leu
            435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Arg
465                 470                 475                 480

Thr Lys Arg Val Phe Leu Glu Ala Glu Ser Glu Glu Ile Phe Ala
                485                 490                 495

His Leu Gly Leu Asp Tyr Ile Glu Pro Trp Glu Arg Asn Ala
                500                 505                 510

<210> SEQ ID NO 2
<211> LENGTH: 381
<212> TYPE: PRT
<213> ORGANISM: artificial sequence
<220> FEATURE:
<223> OTHER INFORMATION: murine TdT catalytic domain (CTdT)

<400> SEQUENCE: 2

Asn Ser Ser Pro Ser Pro Val Pro Gly Ser Gln Asn Val Pro Ala Pro
1               5                   10                  15

Ala Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Leu Arg Glu Asn Glu Gly Ser Cys Leu Ala Phe Met Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Ala Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Cys Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Arg Gly
        195                 200                 205
```

-continued

Lys Met Thr Gly His Asp Val Asp Phe Leu Ile Thr Ser Pro Glu Ala
210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Lys Val Asp Ala Leu Asp His Phe
            260                 265                 270

Gln Lys Cys Phe Leu Ile Leu Lys Leu Asp His Gly Arg Val His Ser
        275                 280                 285

Glu Lys Ser Gly Gln Gln Glu Gly Lys Gly Trp Lys Ala Ile Arg Val
290                 295                 300

Asp Leu Val Met Cys Pro Tyr Asp Arg Arg Ala Phe Ala Leu Leu Gly
305                 310                 315                 320

Trp Thr Gly Ser Arg Gln Phe Glu Arg Asp Leu Arg Arg Tyr Ala Thr
                325                 330                 335

His Glu Arg Lys Met Met Leu Asp Asn His Ala Leu Tyr Asp Arg Thr
            340                 345                 350

Lys Arg Val Phe Leu Glu Ala Glu Ser Glu Glu Glu Ile Phe Ala His
        355                 360                 365

Leu Gly Leu Asp Tyr Ile Glu Pro Trp Glu Arg Asn Ala
370                 375                 380

<210> SEQ ID NO 3
<211> LENGTH: 494
<212> TYPE: PRT
<213> ORGANISM: artificial sequence
<220> FEATURE:
<223> OTHER INFORMATION: Human Pol(mu)

<400> SEQUENCE: 3

Met Leu Pro Lys Arg Arg Ala Arg Val Gly Ser Pro Ser Gly Asp
1               5                   10                  15

Ala Ala Ser Ser Thr Pro Pro Ser Thr Arg Phe Pro Gly Val Ala Ile
                20                  25                  30

Tyr Leu Val Glu Pro Arg Met Gly Arg Ser Arg Arg Ala Phe Leu Thr
            35                  40                  45

Gly Leu Ala Arg Ser Lys Gly Phe Arg Val Leu Asp Ala Cys Ser Ser
        50                  55                  60

Glu Ala Thr His Val Val Met Glu Glu Thr Ser Ala Glu Glu Ala Val
65                  70                  75                  80

Ser Trp Gln Glu Arg Arg Met Ala Ala Ala Pro Pro Gly Cys Thr Pro
                85                  90                  95

Pro Ala Leu Leu Asp Ile Ser Trp Leu Thr Glu Ser Leu Gly Ala Gly
            100                 105                 110

Gln Pro Val Pro Val Glu Cys Arg His Arg Leu Glu Val Ala Gly Pro
        115                 120                 125

Arg Lys Gly Pro Leu Ser Pro Ala Trp Met Pro Ala Tyr Ala Cys Gln
    130                 135                 140

Arg Pro Thr Pro Leu Thr His His Asn Thr Gly Leu Ser Glu Ala Leu
145                 150                 155                 160

Glu Ile Leu Ala Glu Ala Ala Gly Phe Glu Gly Ser Glu Gly Arg Leu
                165                 170                 175

Leu Thr Phe Cys Arg Ala Ala Ser Val Leu Lys Ala Leu Pro Ser Pro
            180                 185                 190

```
Val Thr Thr Leu Ser Gln Leu Gln Gly Leu Pro His Phe Gly Glu His
            195                 200                 205

Ser Ser Arg Val Val Gln Glu Leu Leu Glu His Gly Val Cys Glu Glu
210                 215                 220

Val Glu Arg Val Arg Arg Ser Glu Arg Tyr Gln Thr Met Lys Leu Phe
225                 230                 235                 240

Thr Gln Ile Phe Gly Val Gly Val Lys Thr Ala Asp Arg Trp Tyr Arg
            245                 250                 255

Glu Gly Leu Arg Thr Leu Asp Asp Leu Arg Glu Gln Pro Gln Lys Leu
            260                 265                 270

Thr Gln Gln Gln Lys Ala Gly Leu Gln His His Gln Asp Leu Ser Thr
            275                 280                 285

Pro Val Leu Arg Ser Asp Val Asp Ala Leu Gln Gln Val Val Glu Glu
            290                 295                 300

Ala Val Gly Gln Ala Leu Pro Gly Ala Thr Val Thr Leu Thr Gly Gly
305                 310                 315                 320

Phe Arg Arg Gly Lys Leu Gln Gly His Asp Val Asp Phe Leu Ile Thr
            325                 330                 335

His Pro Lys Glu Gly Gln Glu Ala Gly Leu Leu Pro Arg Val Met Cys
            340                 345                 350

Arg Leu Gln Asp Gln Gly Leu Ile Leu Tyr His Gln His Gln His Ser
            355                 360                 365

Cys Cys Glu Ser Pro Thr Arg Leu Ala Gln Gln Ser His Met Asp Ala
            370                 375                 380

Phe Glu Arg Ser Phe Cys Ile Phe Arg Leu Pro Gln Pro Gly Ala
385                 390                 395                 400

Ala Val Gly Gly Ser Thr Arg Pro Cys Pro Ser Trp Lys Ala Val Arg
            405                 410                 415

Val Asp Leu Val Val Ala Pro Val Ser Gln Phe Pro Phe Ala Leu Leu
            420                 425                 430

Gly Trp Thr Gly Ser Lys Leu Phe Gln Arg Glu Leu Arg Arg Phe Ser
            435                 440                 445

Arg Lys Glu Lys Gly Leu Trp Leu Asn Ser His Gly Leu Phe Asp Pro
450                 455                 460

Glu Gln Lys Thr Phe Phe Gln Ala Ala Ser Glu Glu Asp Ile Phe Arg
465                 470                 475                 480

His Leu Gly Leu Glu Tyr Leu Pro Pro Glu Gln Arg Asn Ala
            485                 490

<210> SEQ ID NO 4
<211> LENGTH: 401
<212> TYPE: PRT
<213> ORGANISM: artificial sequence
<220> FEATURE:
<223> OTHER INFORMATION: Tag TdT

<400> SEQUENCE: 4

Thr Met Gly Ser Ser His His His His His Ser Ser Gly Leu Val
1               5                   10                  15

Pro Arg Gly Ser His Met Ser Pro Ser Pro Val Pro Gly Ser Gln Asn
                20                  25                  30

Val Pro Ala Pro Ala Val Lys Lys Ile Ser Gln Tyr Ala Cys Gln Arg
            35                  40                  45

Arg Thr Thr Leu Asn Asn Tyr Asn Gln Leu Phe Thr Asp Ala Leu Asp
50                  55                  60
```

Ile Leu Ala Glu Asn Asp Glu Leu Arg Glu Asn Glu Gly Ser Cys Leu
65                  70                  75                  80

Ala Phe Met Arg Ala Ser Ser Val Leu Lys Ser Leu Pro Phe Pro Ile
                85                  90                  95

Thr Ser Met Lys Asp Thr Glu Gly Ile Pro Cys Leu Gly Asp Lys Val
            100                 105                 110

Lys Ser Ile Ile Glu Gly Ile Ile Glu Asp Gly Glu Ser Ser Glu Ala
        115                 120                 125

Lys Ala Val Leu Asn Asp Glu Arg Tyr Lys Ser Phe Lys Leu Phe Thr
130                 135                 140

Ser Val Phe Gly Val Gly Leu Lys Thr Ala Glu Lys Trp Phe Arg Met
145                 150                 155                 160

Gly Phe Arg Thr Leu Ser Lys Ile Gln Ser Asp Lys Ser Leu Arg Phe
                165                 170                 175

Thr Gln Met Gln Lys Ala Gly Phe Leu Tyr Tyr Glu Asp Leu Val Ser
            180                 185                 190

Cys Val Asn Arg Pro Glu Ala Glu Ala Val Ser Met Leu Val Lys Glu
        195                 200                 205

Ala Val Val Thr Phe Leu Pro Asp Ala Leu Val Thr Met Thr Gly Gly
210                 215                 220

Phe Arg Arg Gly Lys Met Thr Gly His Asp Val Asp Phe Leu Ile Thr
225                 230                 235                 240

Ser Pro Glu Ala Thr Glu Asp Glu Glu Gln Gln Leu Leu His Lys Val
                245                 250                 255

Thr Asp Phe Trp Lys Gln Gln Gly Leu Leu Leu Tyr Cys Asp Ile Leu
            260                 265                 270

Glu Ser Thr Phe Glu Lys Phe Lys Gln Pro Ser Arg Lys Val Asp Ala
        275                 280                 285

Leu Asp His Phe Gln Lys Cys Phe Leu Ile Leu Lys Leu Asp His Gly
290                 295                 300

Arg Val His Ser Glu Lys Ser Gly Gln Gln Glu Gly Lys Gly Trp Lys
305                 310                 315                 320

Ala Ile Arg Val Asp Leu Val Met Cys Pro Tyr Asp Arg Arg Ala Phe
                325                 330                 335

Ala Leu Leu Gly Trp Thr Gly Ser Arg Gln Phe Glu Arg Asp Leu Arg
            340                 345                 350

Arg Tyr Ala Thr His Glu Arg Lys Met Met Leu Asp Asn His Ala Leu
        355                 360                 365

Tyr Asp Arg Thr Lys Arg Val Phe Leu Glu Ala Glu Ser Glu Glu Glu
370                 375                 380

Ile Phe Ala His Leu Gly Leu Asp Tyr Ile Glu Pro Trp Glu Arg Asn
385                 390                 395                 400

Ala

<210> SEQ ID NO 5
<211> LENGTH: 20
<212> TYPE: DNA
<213> ORGANISM: artificial sequence
<220> FEATURE:
<223> OTHER INFORMATION: T7-pro primer

<400> SEQUENCE: 5
taatacgact cactataggg                                              20

-continued

<210> SEQ ID NO 6
<211> LENGTH: 19
<212> TYPE: DNA
<213> ORGANISM: artificial sequence
<220> FEATURE:
<223> OTHER INFORMATION: T7-ter primer

<400> SEQUENCE: 6
gctagttatt gctcagcgg                                                    19

<210> SEQ ID NO 7
<211> LENGTH: 18
<212> TYPE: DNA
<213> ORGANISM: artificial sequence
<220> FEATURE:
<223> OTHER INFORMATION: primer

<400> SEQUENCE: 7
aaaaaaaaaa aaaagggg                                                     18

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
tttttttttt ttaaataagg                                                   20

<210> SEQ ID NO 9
<211> LENGTH: 401
<212> TYPE: PRT
<213> ORGANISM: artificial sequence
<220> FEATURE:
<223> OTHER INFORMATION: Reference TdT variant

<400> SEQUENCE: 9

Thr Met Gly Ser Ser His His His His His Ser Ser Gly Leu Val
1               5                   10                  15

Pro Arg Gly Ser His Met Ser Pro Ser Pro Val Pro Gly Ser Gln Asn
            20                  25                  30

Val Pro Ala Pro Ala Val Lys Lys Ile Ser Gln Tyr Ala Cys Gln Arg
        35                  40                  45

Arg Thr Thr Leu Asn Asn Tyr Asn Gln Leu Phe Thr Asp Ala Leu Asp
    50                  55                  60

Ile Leu Ala Glu Asn Asp Glu Leu Arg Glu Asn Glu Gly Ser Cys Leu
65                  70                  75                  80

Ala Phe Met Arg Ala Ser Ser Val Leu Lys Ser Leu Pro Phe Pro Ile
                85                  90                  95

Thr Ser Met Lys Asp Thr Glu Gly Ile Pro Cys Leu Gly Asp Lys Val
            100                 105                 110

Lys Ser Ile Ile Glu Gly Ile Ile Glu Asp Gly Glu Ser Ser Glu Ala
        115                 120                 125

Lys Ala Val Leu Asn Asp Glu Arg Tyr Lys Ser Phe Lys Leu Phe Thr
    130                 135                 140

Ser Val Phe Gly Val Gly Leu Lys Thr Ala Glu Lys Trp Phe Arg Met
145                 150                 155                 160

Gly Phe Arg Thr Leu Ser Lys Ile Gln Ser Asp Lys Ser Leu Arg Phe
                165                 170                 175

-continued

```
Thr Gln Met Gln Lys Ala Gly Phe Leu Tyr Tyr Glu Asp Leu Val Ser
            180                 185                 190
Cys Val Asn Arg Pro Glu Ala Glu Ala Val Ser Met Leu Val Lys Glu
        195                 200                 205
Ala Val Val Thr Phe Leu Pro Asp Ala Leu Val Thr Met Thr Gly Gly
        210                 215                 220
Phe Arg Arg Gly Lys Met Thr Gly His Asp Val Asp Phe Leu Ile Thr
225                 230                 235                 240
Ser Pro Glu Ala Thr Glu Asp Glu Glu Gln Gln Leu Leu His Lys Val
                245                 250                 255
Thr Asp Phe Trp Lys Gln Gln Gly Leu Leu Leu Tyr Cys Asp Ile Leu
                260                 265                 270
Glu Ser Thr Phe Glu Lys Phe Lys Gln Pro Ser Arg Lys Val Asp Ala
            275                 280                 285
Leu Asp His Phe Gln Lys Cys Phe Leu Ile Leu Lys Leu Asp His Gly
            290                 295                 300
Arg Val His Ser Glu Lys Ser Gly Gln Gln Glu Gly Lys Gly Trp Lys
305                 310                 315                 320
Ala Ile Arg Val Asp Leu Val Met Cys Pro Tyr Asp Arg Arg Ala Phe
                325                 330                 335
Ala Leu Leu Gly Trp Thr Gly Ser Ala Gln Phe Ser Arg Asp Leu Arg
                340                 345                 350
Arg Tyr Ala Thr His Glu Arg Lys Met Met Leu Asp Asn His Ala Leu
            355                 360                 365
Tyr Asp Arg Thr Lys Arg Val Phe Leu Glu Ala Glu Ser Glu Glu Glu
    370                 375                 380
Ile Phe Ala His Leu Gly Leu Asp Tyr Ile Glu Pro Trp Glu Arg Asn
385                 390                 395                 400
Ala
```

VARIANTS OF TERMINAL DEOXYNUCLEOTIDYL TRANSFERASE AND USES THEREOF

FIELD OF THE INVENTION

The invention relates to variants of Terminal deoxynucleotidyl Transferase (TdT) and uses thereof for the enzymatic synthesis of nucleic acid sequences without template. More particularly, the present invention relates to such variants suitable to incorporate modified nucleotides, for the synthesis of nucleic acid molecules with determined or controlled sequences.

BACKGROUND

Methods for de novo chemical synthesis of nucleic acids based on solid-phase phosphoramidite chemistry have been largely used and refined over the past 40 years. The technique consists of a four-step chain elongation cycle that adds one base per cycle onto a growing oligonucleotide chain attached to a solid support matrix. Although it has been the method of choice to synthesize nucleic acids during the past decades, this technology has some notable limitations: It requires the use of multiple solvents and reagents, and due to limitations in chemical reaction efficiency, the length of synthetic oligonucleotides typically do not exceed 150-200 bases. Moreover, these short fragments need to be further assembled to provide the desired DNA sequence.

One alternative to chemical synthesis consists in using template independent DNA polymerases that will add reversible terminator modified nucleotides to a growing single stranded chain of nucleic acids. This allows the addition of one type of nucleotide per cycle in a controlled fashion.

Some native enzymes are able to act on natural nucleotides in the absence of template and so can catalyze the synthesis of nucleic acids in an uncontrolled fashion. However, they are particularly inefficient to incorporate modified nucleotides and more particularly reversible terminator modified nucleotides. Efforts have been made to develop new DNA polymerases able to act on modified nucleotides but the resulting enzymes are not fully satisfactory in terms of performances for the synthesis of any type of nucleic acids.

So far, only few DNA polymerases that can act efficiently on single strand DNA (without the use of template) have been identified. The most characterized polymerase having such template-independent activity is the Terminal deoxynucleotidyl Transferase (TdT). TdT enzymes have been extensively used to modify single stranded DNA for various types of applications including biotechnology, biomedical research and synthetic biology. However, native TdT is poorly able to use modified nucleotides.

Several attempts to develop modified TdT with acceptable performance for the incorporation of modified nucleotides have been carried over. However, the performances of the incorporation of such modified nucleotides is still a limiting factor. Incorporation efficiency is the key parameter driving the overall purity and yield of synthesis. These two characteristics of the synthesis process have a significant impact of quality, turnaround time and cost of nucleic acid products.

There is therefore a need to develop improved TdT capable to use modified nucleotides in the absence of template, for developing efficient and cost-effective methods for the nucleic acid synthesis.

SUMMARY OF THE INVENTION

By working on TdT for de novo synthesis of polynucleotides with controlled sequence and without the use of a template, the inventors have discovered that some targeted amino acid residues of the catalytic domain of the TdT may be specifically modified to improve the ability of such modified TdT for synthesizing polynucleotides. More particularly, the inventors have developed modified TdT with targeted amino acid substitution(s) that lead to reduce the overall cost of synthesizing custom nucleic acids, even with modified nucleotides. The modified TdT may present one or more targeted amino acids substitution as compared to wild-type TdT. More particularly, the modified TdT present at least the amino acid sequence of the catalytic domain (SEQ ID N° 2) with one or more targeted amino acid substitution(s). The template-independent polymerases of the invention allow to synthesize polynucleotides faster, cheaper and of better quality.

It is therefore an object of the invention to provide a variant of Terminal deoxynucleotidyl Transferase (TdT) which (i) comprises the amino acid sequence as set forth in SEQ ID N° 2 or a functionally equivalent sequence, with at least an amino acid substitution at position corresponding to residue C302, or functionally equivalent residue, wherein the position is numbered by reference to the amino acid sequence set forth in SEQ ID N° 1, (ii) is able to synthesize a nucleic acid fragment without template and (iii) is able to incorporate a modified nucleotide into the nucleic fragment.

In a particular embodiment, the substitution is selected from C302G/R/P/A/V/S/N/Q/D, preferably from C302G/R.

In some embodiments, the invention is directed to compositions comprising TdT variants having at least 80 percent identity with the reference or wild type TdT sequence SEQ ID NO: 1 wherein (i) such TdT variants have a mutation from C302G/R/P/A/V/S/N/Q/D, more preferably C302G/R, or functional equivalents thereof, and (ii) such TdT variants incorporate 3'-O-modified nucleoside triphosphates with greater efficiency than the reference or wild type TdT.

It is also an object of the invention to provide a variant of Terminal deoxynucleotidyl Transferase (TdT) which (i) comprises the amino acid sequence as set forth in SEQ ID N° 2 or a functionally equivalent sequence, with at least two amino acid substitutions, preferably at least three amino acid substitutions selected from M192R/Q, L260P, C302G/R, R336L/N, D379V, R454P/N and E457N/L/T/S, or functionally equivalent residues, wherein the positions are numbered by reference to the amino acid sequence set forth in SEQ ID N° 1, (ii) is able to synthesize a nucleic acid fragment without template and (iii) is able to incorporate a modified nucleotide into the nucleic fragment.

It is another object of the invention to provide a nucleic acid molecule encoding a variant of a TdT as defined above and/or an expression vector comprising such nucleic acid molecule, and/or a host cell comprising such nucleic acid molecule or expression vector.

It is a further object of the invention to provide a process for producing a variant of TdT according to the invention, wherein a host cell as defined above is cultivated under culture conditions allowing the expression of the nucleic acid encoding said variant, and wherein the variant is optionally retrieved.

The invention further relates to the use of a variant of TdT, for synthesizing a nucleic acid molecule without template, with one or more 3'O-modified nucleotides. In some embodiments, such methods comprise the steps of (a) providing an initiating fragment comprising an oligonucleotide having a free 3'-hydroxyl; (b) reacting under enzymatic extension conditions a TdT variant of the invention with the initiating fragment or an extended initiating fragment in the presence of a 3'-O-reversibly blocked nucleoside. In some embodiments, such method further includes steps of (c) deblocking the extended initiating fragments to form extended initiating fragments with free 3'-hydroxyls and (d) repeating steps (b) and (c) until a nucleic acid molecule of a predetermined sequence is synthesized.

It is also an object of the invention to provide a process for synthesizing a nucleic acid molecule without template, comprising a step of contacting a nucleic acid primer with both at least one nucleotide, preferably at least one 3' O-modified nucleotide, and a variant of TdT according to the invention.

The present invention further provides a kit for performing a nucleotide incorporation reaction comprising a variant of TdT according to the invention, and one or more nucleotides, preferably one or more 3'O-modified nucleotides, and optionally at least one nucleic acid primer.

DESCRIPTION OF THE INVENTION

Figure 1:
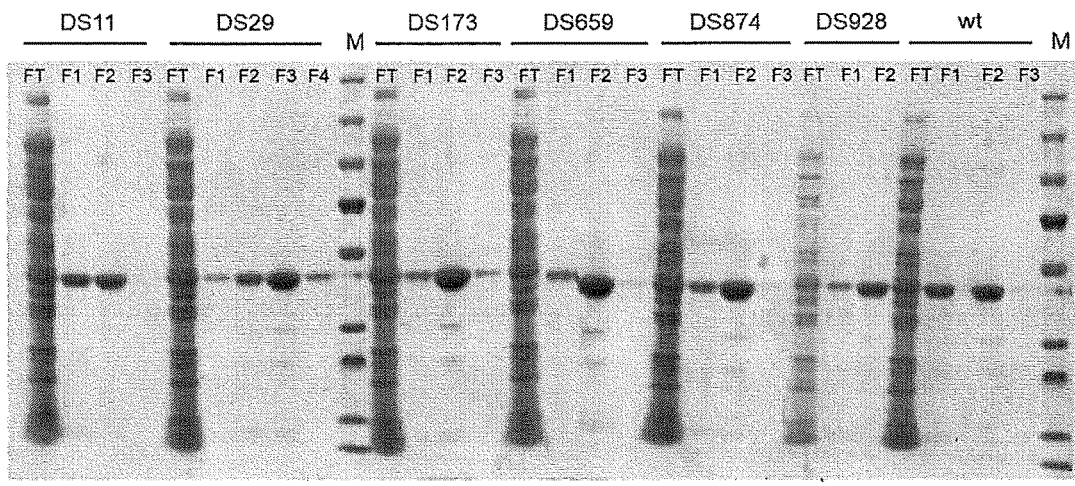
FIG. 1: Purification assay of wild type (wt) TdT and different TdT variants of the invention. Protein samples were loaded on SDS-PAGE analysis gel and migrated through electrophoresis.

The DNA polymerase families are divided into seven families based on their sequence homology and crystal structure. Among them, the polymerases of PolX family represent a wide variety of polymerases from replicative polymerases to terminal transferase enzymes. Polymerases from PolX family are present across a very wide range of eukaryotic organisms. Polymerases from the PolX family are implicated in a vast variety of biological processes and in particular in DNA damage repair mechanisms or error correction mechanisms. The PolX family regroups polymerase β (Pol β), μ (Pol μ), λ (Pol λ), IV from yeast (Pol IV) and the Terminal deoxynucleotidyl Transferase (TdT). TdT is naturally implicated in DNA repair and maintenance mechanisms. In particular, TdT has the unique ability to conserve a nucleotide polymerization activity even in absence of template strand. In specific conditions and with natural nucleotides, TdT is able to elongate DNA fragments with several hundred nucleotides, in absence of any complementary strand. However, wild type TdT is totally unable to efficiently incorporate sugar-modified nucleotides.

It is thus the purpose of the present invention to provide variants of TdT with targeted mutation(s) that allow them to incorporate modified nucleotides into a nucleic fragment during synthesize of said nucleotide fragment. More particularly, the inventors have identified specific amino acid residues that may be advantageously substituted, alone or in combination, to improve the ability of the enzyme to synthesize nucleic acid fragments of various length and with pre-determined sequence, including by using modified nucleotides.

Definitions

As used therein, the terms "mutant" and "variant" may be used interchangeably to refer to polypeptides derived from SEQ ID N° 2 and comprising a modification or an alteration, i.e., a substitution, insertion, and/or deletion, at one or more (e.g., several) positions and having both a polymerase activity without template and ability to incorporate one or more modified terminator nucleotides. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consist in deleting, inserting or substituting one or several amino-acids in the sequence of a protein or in the case of the invention of a polymerase. Targeted amino-acids could be concomitant or distributed along the whole sequence of the polymerase. Specific motifs or structural features could be targeted for example.

The terms "modification" or "alteration" as used herein in relation to a position or amino acid mean that the amino acid in the specific position has been modified compared to the amino acid of the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions.

The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

As used herein, the terms "sequence identity" or "identity" refer to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Herein, the terms "peptide", "polypeptide", "protein", "enzyme", refer to a chain of amino acids linked by peptide bonds, regardless of the number of amino acids forming said chain.

Unless otherwise specified, the positions disclosed in the present application are numbered by reference to the amino acid sequence set forth in SEQ ID N° 1, which corresponds to the amino acid sequence of murine TdT.

Variants of TdT

The present invention provides variants of TdT enzyme that can be used for synthesizing polynucleotides of predetermined sequences, such as DNA or RNA, without the use of template strand. The TdT variants of the invention allow modified nucleotides, and more particularly 3'O-modified nucleotides, to be used in an enzyme-mediated method of polynucleotide synthesis.

In the context of the invention, "modified Terminal desoxyribonucleotidyl Transferase", "modified TdT", "variants of Terminal desoxyribonucleotidyl Transferase" and "variants of TdT" refer to enzymes that share at least 25% identity with the amino acid sequence of a TdT and comprises at least the amino acid sequence as set forth in SEQ ID N° 2, or any functionally equivalent fragment, excepting at least one amino acid residue substitution. Preferably, the variant of TdT shares at least 40% identity with SEQ ID N° 1.

It is known that TdT is composed of distinct domains from N-terminus to C-terminus that correspond to nuclear localization domain (NLS), BRCT-like domain and catalytic domain (C-TdT), respectively. The catalytic domain (SEQ ID N° 2) exhibits the polymerase activity.

The variants of the present invention are described according to their mutations on specific residues, whose positions are determined by alignment with or reference to the enzymatic sequence SEQ ID N° 1, which corresponds to the amino acid sequence of murine TdT. More particularly, the variants of the invention comprise at least the catalytic domain of a TdT. In the present disclosure, the residues correspond to the residues of the catalytic domaine of murine TdT (SEQ ID N° 2). However, in the context of the invention, any variant having a functionally equivalent sequence to SEQ ID N° 2 and/or SEQ ID N° 1 is also part of the invention. In the same way, any variant bearing the same mutations on functionally equivalent residues is also part of the invention.

In the context of the invention, "functionally equivalent sequence" refers to a sequence of a TdT homologous to SEQ ID N° 1 or SEQ ID N° 2. By "functionally equivalent residue" is meant a residue in a sequence of a TdT of sequence homologous to SEQ ID N° 1 and having an identical functional role. Functionally equivalent residues are identified by using sequence alignments, for example, using the Mutalin line alignment software (http://multalin.toulouse.inra.fr/multalin/multalin.html; 1988, Nucl. Acids Res., 16 (22), 10881-10890). After alignment, the functionally equivalent residues are at homologous positions on the different sequences considered. Sequence alignments and identification of functionally equivalent residues may be between any TdT and their natural variants, including interspecies.

TdT could be found in many other organisms or microorganisms. All those TdT are good candidates for performing the present invention. In particular, modifications to alter a particular TdT sequence to give said polymerase an increased ability to incorporate modified nucleotides, can target any other TdT sequence. Accordingly, mutations or combinations described herein by reference to SEQ ID N° 1, and more particularly to SEQ ID N° 2 that corresponds to amino acid residues 130 to 510 of SEQ ID N° 1, can be transposed to any other TdT sequence.

According to a first aspect of the invention, the variant of Terminal deoxynucleotidyl Transferase (TdT) (i) comprises the amino acid sequence as set forth in SEQ ID N° 2 or a functionally equivalent sequence, with at least an amino acid substitution at position corresponding to residue C302, or functionally equivalent residue, wherein the position is numbered by reference to the amino acid sequence set forth in SEQ ID N° 1, (ii) is able to synthesize a nucleic acid fragment without template and (iii) is able to incorporate a reversible modified terminator nucleotide into the nucleic fragment. Indeed, the inventors have discovered that a substitution on the amino acid residue C302 or any functionally equivalent residue has a great impact on both surface and interaction properties of the enzyme with nucleotides, which may allow incorporation of 3'O-modified nucleotides in a nucleic acid sequence.

Advantageously, the substitution is selected from C302G/R/P/A/V/S/N/Q/D, preferably from C302G/R.

In a particular embodiment, the variant further comprises at least one amino acid substitution at position corresponding to residues selected from M192, L260, R336, D379, R454 and E457, or functionally equivalent residues. Interestingly, substitution(s) on residues M192, R336, R454 and/or E457 have an impact on both size and shape of the catalytic pocket, and substitution(s) on residues L260 and/or D379 have an impact on the interaction domain with the growing nucleic acid chain.

In a particular embodiment, the variant comprises the amino acid sequence as set forth in SEQ ID N° 2, or any functional equivalent sequence, and at least an amino acid substitution at both positions C302 and R336, or functionally equivalent residues.

Alternatively, or in addition, the variant further comprises at least two amino acid substitutions, preferably at least three, more preferably at least four, even more preferably at least five, and more preferably six amino acid substitutions at positions corresponding to residues selected from M192, L260, R336, D379, R454 and E457, or functionally equivalent residues.

Preferably, the substitutions are selected from M192R/Q/G/A/V/D/N/H/E, L260P/M/E/N/F/K/D/A/G, R336N/L/K/H/G/D/A/P, D379V/A/G/N/E/R/H/K/T, R454P/N/A/L/K/H/G/D, and E457N/T/S/L/V/K/H/G/D, preferably selected from M192R/Q, L260P, R336L/N, D379V, R454P/N and E457N/L/T/S.

Alternatively or in addition, the variant further comprises at least one substitution at position corresponding to residues selected from T340, G413, H416, E418, W450, and A510, or functionally equivalent residues, preferably selected from T340S/N/Q/C/G/M/K/D, G413L/S/P/R, H416D, E418A/V, W450Y/F/P/L/I/V/A/G/E, and A510V/T/G. Substitution(s) on residues T340, W450 and/or A510 have an impact on both size and shape of the catalytic pocket. Substitution(s) on residues G413, H416 and/or E418 have an impact on the protein loop secondary structure. Substitution on residue A510 has an impact on both size and shape of the catalytic pocket.

Interestingly, the inventors have discovered that the variant may advantageously comprise the combination of substitutions L181F+A237V+R480K and/or G413L/S+H416D+E418A, which are herein after presented as constant mutations, which have a great impact on the protein stability.

In a particular embodiment, the variant comprises the combination of two amino acid substitutions selected from M192R+C302R, M192R+C302G, M192Q+C302R, M192Q+C302G, L260P+C302R, L260P+C302G, C302R+R336L, C302R+R336N, C302R+D379V, C302R+R454P, C302R+R454A, C302R+E457L, C302R+E457N, C302G+R336L, C302G+R336N, C302G+D379V, C302G+R454P, C302G+R454A, C302G+E457L and C302G+E457N, preferably C302R+R336L or C302R+R336N.

In a particular embodiment, the variant comprises the combination of three amino acid substitutions selected from M192R+L260P+C302R, M192R+L260P+C302G, M192R+C302R+R336L, M192R+C302R+R336N, M192R+C302R+D379V, M192R+C302R+R454P, M192R+C302R+R454A, M192R+C302R+E457L, M192R+C302R+E457N, M192R+C302G+R336L, M192R+C302G+R336N, M192R+C302G+D379V, M192R+C302G+R454P, M192R+C302G+R454A, M192R+C302G+E457N, M192Q+L260P+C302R, M192Q+L260P+C302G, M192Q+C302R+R336L, M192Q+C302R+R336N, M192Q+C302R+D379V, M192Q+C302R+R454P, M192Q+C302R+R454A, M192Q+C302R+E457L, M192Q+C302R+E457N, M192Q+C302G+R336L, M192Q+C302G+R336N, M192Q+C302G+D379V, M192Q+C302G+R454P, M192Q+C302G+R454A, M192Q+C302G+E457L, M192Q+C302G+E457N, L260P+C302R+R336L, L260P+C302R+R336N, L260P+C302R+D379V, L260P+C302R+R454P, L260P+C302R+R454A, L260P+C302R+E457L, L260P+C302R+E457N, L260P+C302G+R336L, L260P+C302G+R336N, L260P+C302G+D379V, L260P+C302G+R454P, L260P+C302G+R454A, L260P+C302G+E457L, L260P+C302G+E457N, C302R+R336L+D379V, C302R+R336L+R454P, C302R+R336L+R454A, C302R+R336L+E457L, C302R+R336L+E457N, C302R+R336N+D379V, C302R+R336N+R454P, C302R+R336N+R454A, C302R+R336N+E457L, C302R+R336N+E457N, C302R+D379V+R454P, C302R+D379V+R454A, C302R+D379V+E457L, C302R+D379V+E457N, C302R+R454P+E457L, C302R+R454P+E457N, C302R+R454A+E457L, C302R+R454A+E457N, C302G+R336L+D379V, C302G+R336L+R454P, C302G+R336L+R454A, C302G+R336L+E457L, C302G+R336L+E457N, C302G+R336N+D379V, C302G+R336N+R454P, C302G+R336N+R454A, C302G+R336N+E457L, C302G+R336N+E457N, C302G+D379V+R454A, C302G+D379V+E457L, C302G+D379V+E457N, C302G+R454P+E457L, C302G+R454P+E457N, C302G+R454A+E457L and C302G+R454A+E457N, preferably M192R+C302R+R336L, M192R+C302R+R336N, M192R+C302G+R336L, M192R+C302G+R336N, M192Q+C302R+R336L, M192Q+C302R+R336N, M192Q+C302G+R336L, M192Q+C302G+R336N, L260P+C302R+R336L, L260P+C302R+R336N, L260P+C302G+R336L, L260P+C302G+R336N, C302R+R336L+D379V, C302R+R336L+R454P, C302R+R336L+R454A, C302R+R336L+E457N, C302R+R336L+E457N, C302R+R336N+D379V, C302R+R336N+R454P, C302R+R336N+R454A, C302R+R336N+E457L, C302R+R336N+E457N, C302G+R336L+D379V, C302G+R336L+R454P, C302G+R336L+R454A, C302G+R336L+E457L, C302G+R336L+E457N, C302G+R336N+D379V, C302G+R336N+R454P, C302G+R336N+R454A, C302G+R336N+E457L, and C302G+R336N+E457N.

In a particular embodiment, the variant of TdT comprises the amino acid sequence of SEQ ID N° 2, or functionally equivalent sequence, with the combination of substitutions M192R+L260P+C302R+R336L+R454P+E457N (DS11), or functionally equivalent residues.

In a particular embodiment, the variant of TdT comprises the amino acid sequence of SEQ ID N° 2, or functionally equivalent sequence, with the combination of substitutions M192R+L260P+C302R+R336N+R454P+E457N (DS29), or functionally equivalent residues.

In a particular embodiment, the variant of TdT comprises the amino acid sequence of SEQ ID N° 2, or functionally equivalent sequence, with the combination of substitutions M192R+C302R+R336L+R454P+E457N (DS173), or functionally equivalent residues.

In a particular embodiment, the variant of TdT comprises the amino acid sequence of SEQ ID N° 2, or functionally equivalent sequence, with the combination of substitutions L260P+C302R+R336L+R454P+E457N (DS659), or functionally equivalent residues.

In a particular embodiment, the variant of TdT comprises the amino acid sequence of SEQ ID N° 2, or functionally equivalent sequence, with the combination of substitutions C302G+R336L+R454P+E457L (DS874), or functionally equivalent residues.

In a particular embodiment, the variant of TdT comprises the amino acid sequence of SEQ ID N° 2, or functionally equivalent sequence, with the combination of substitutions M192R+C302G+R336L+R454P+E457L (DS226), or functionally equivalent residues.

In a particular embodiment, the variant of TdT comprises the amino acid sequence of SEQ ID N° 2, or functionally equivalent sequence, with the combination of substitutions M192Q+C302G+R336L+E457N (DS557), or functionally equivalent residues.

The present invention more particularly provides a variant of TdT having the amino acid sequence as set forth in SEQ ID N° 2 or functionally equivalent sequence, with at least one substitution or combination of substitution as listed in table 1. The variants of the invention comprise at least the amino acid substitutions listed in the left column and called "Variable Mutations", or functionally equivalent residues, and optionally one or both combination of substitutions listed in the right column and called "Optional Constant Mutations", or functionally equivalent sequence.

TABLE 1

Variants of TdT having the amino acid sequence of SEQ ID N° 2 with at least a substitution on residue C302

| Name | Variable Mutations | Optional Constant Mutations |
|---|---|---|
| DS1 | M192R + L260P + C302R + R336L + D379V + R454P + E457L | L181F + A237V + R480K and/or G413L/S + H416D + E418A |
| DS2 | M192R + L260P + C302R + R336L + D379V + R454P + E457N | L181F + A237V + R480K and/or G413L/S + H416D + E418A |
| DS3 | M192R + L260P + C302R + R336L + D379V + R454P | L181F + A237V + R480K and/or G413L/S + H416D + E418A |
| DS4 | M192R + L260P + C302R + R336L + D379V + R454A + E457L | L181F + A237V + R480K and/or G413L/S + H416D + E418A |
| DS5 | M192R + L260P + C302R + R336L + D379V + R454A + E457N | L181F + A237V + R480K and/or G413L/S + H416D + E418A |
| DS6 | M192R + L260P + C302R + R336L + D379V + R454A | L181F + A237V + R480K and/or G413L/S + H416D + E418A |
| DS7 | M192R + L260P + C302R + R336L + D379V + E457L | L181F + A237V + R480K and/or G413L/S + H416D + E418A |
| DS8 | M192R + L260P + C302R + R336L + D379V + E457N | L181F + A237V + R480K and/or G413L/S + H416D + E418A |
| DS9 | M192R + L260P + C302R + R336L + D379V | L181F + A237V + R480K and/or G413L/S + H416D + E418A |
| DS10 | M192R + L260P + C302R + R336L + R454P + E457L | L181F + A237V + R480K and/or G413L/S + H416D + E418A |
| DS11 | M192R + L260P + C302R + R336L + R454P + E457N | L181F + A237V + R480K and/or G413L/S + H416D + E418A |
| DS12 | M192R + L260P + C302R + R336L + R454P | L181F + A237V + R480K and/or G413L/S + H416D + E418A |
| DS13 | M192R + L260P + C302R + R336L + R454A + E457L | L181F + A237V + R480K and/or G413L/S + H416D + E418A |
| DS14 | M192R + L260P + C302R + R336L + R454A + E457N | L181F + A237V + R480K and/or G413L/S + H416D + E418A |
| DS15 | M192R + L260P + C302R + R336L + R454A | L181F + A237V + R480K and/or G413L/S + H416D + E418A |
| DS16 | M192R + L260P + C302R + R336L + E457L | L181F + A237V + R480K and/or G413L/S + H416D + E418A |
| DS17 | M192R + L260P + C302R + R336L + E457N | L181F + A237V + R480K and/or G413L/S + H416D + E418A |
| DS18 | M192R + L260P + C302R + R336L | L181F + A237V + R480K and/or G413L/S + H416D + E418A |
| DS19 | M192R + L260P + C302R + R336N + D379V + R454P + E457L | L181F + A237V + R480K and/or G413L/S + H416D + E418A |
| DS20 | M192R + L2G0P + C302R + R336N + D379V + R454P + E457N | L181F + A237V + R480K and/or G413L/S + H416D + E418A |
| DS21 | M192R + L260P + C302R + R336N + D379V + R454P | L181F + A237V + R480K and/or G413L/S + H416D + E418A |
| DS22 | M192R + L260P + C302R + R336N + D379V + R454A + E457L | L181F + A237V + R480K and/or G413L/S + H416D + E418A |
| DS23 | M192R + L260P + C302R + R336N + D379V + R454A + E457N | L181F + A237V + R480K and/or G413L/S + H416D + E418A |
| DS24 | M192R + L260P + C302R + R336N + D379V + R454A | L181F + A237V + R480K and/or G413L/S + H416D + E418A |
| DS25 | M192R + L260P + C302R + R336N + D379V + E457L | L181F + A237V + R480K and/or G413L/S + H416D + E418A |
| DS26 | M192R + L260P + C302R + R336N + D379V + E457N | L181F + A237V + R480K and/or G413L/S + H416D + E418A |
| DS27 | M192R + L260P + C302R + R336N + D379V | L181F + A237V + R480K and/or G413L/S + H416D + E418A |
| DS28 | M192R + L260P + C302R + R336N + R454P + E457L | L181F + A237V + R480K and/or G413L/S + H416D + E418A |
| DS29 | M192R + L260P + C302R + R336N + R454P + E457N | L181F + A237V + R480K and/or G413L/S + H416D + E418A |
| DS30 | M192R + L260P + C302R + R336N + R454P | L181F + A237V + R480K and/or G413L/S + H416D + E418A |
| DS31 | M192R + L260P + C302R + R336N + R454A + E457L | L181F + A237V + R480K and/or G413L/S + H416D + E418A |
| DS32 | M192R + L260P + C302R + R336N + R454A + E457N | L181F + A237V + R480K and/or G413L/S + H416D + E418A |
| DS33 | M192R + L260P + C302R + R336N + R454A | L181F + A237V + R480K and/or G413L/S + H416D + E418A |
| DS34 | M192R + L260P + C302R + R336N + E457L | L181F + A237V + R480K and/or G413L/S + H416D + E418A |
| DS35 | M192R + L260P + C302R + R336N + E457N | L181F + A237V + R480K and/or G413L/S + H416D + E418A |
| DS36 | M192R + L260P + C302R + R336N | L181F + A237V + R480K and/or G413L/S + H416D + E418A |
| DS37 | M192R + L260P + C302R + D379V + R454P + E457L | L181F + A237V + R480K and/or G413L/S + H416D + E418A |
| DS38 | M192R + L260P + C302R + D379V + R454P + E457N | L181F + A237V + R480K and/or G413L/S + H416D + E418A |
| DS39 | M192R + L260P + C302R + D379V + R454P | L181F + A237V + R480K and/or G413L/S + H416D + E418A |
| DS40 | M192R + L260P + C302R + D379V + R454A + E457L | L181F + A237V + R480K and/or G413L/S + H416D + E418A |
| DS41 | M192R + L260P + C302R + D379V + R454A + E457N | L181F + A237V + R480K and/or G413L/S + H416D + E418A |
| DS42 | M192R + L260P + C302R + D379V + R454A | L181F + A237V + R480K and/or G413L/S + H416D + E418A |
| DS43 | M192R + L260P + C302R + D379V + E457L | L181F + A237V + R480K and/or G413L/S + H416D + E418A |
| DS44 | M192R + L260P + C302R + D379V + E457N | L181F + A237V + R480K and/or G413L/S + H416D + E418A |
| DS45 | M192R + L260P + C302R + D379V | L181F + A237V + R480K and/or G413L/S + H416D + E418A |
| DS46 | M192R + L260P + C302R + R454P + E457L | L181F + A237V + R480K and/or G413L/S + H416D + E418A |
| DS47 | M192R + L260P + C302R + R454P + E457N | L181F + A237V + R480K and/or G413L/S + H416D + E418A |
| DS48 | M192R + L260P + C302R + R454P | L181F + A237V + R480K and/or G413L/S + H416D + E418A |
| DS49 | M192R + L260P + C302R + R454A + E457L | L181F + A237V + R480K and/or G413L/S + H416D + E418A |
| DS50 | M192R + L260P + C302R + R454A + E457N | L181F + A237V + R480K and/or G413L/S + H416D + E418A |
| DS51 | M192R + L260P + C302R + R454A | L181F + A237V + R480K and/or G413L/S + H416D + E418A |
| DS52 | M192R + L260P + C302R + E457L | L181F + A237V + R480K and/or G413L/S + H416D + E418A |
| DS53 | M192R + L260P + C302R + E457N | L181F + A237V + R480K and/or G413L/S + H416D + E418A |
| DS54 | M192R + L260P + C302R | L181F + A237V + R480K and/or G413L/S + H416D + E418A |
| DS55 | M192R + L260P + C302G + R336L + D379V + R454P + E457L | L181F + A237V + R480K and/or G413L/S + H416D + E418A |
| DS56 | M192R + L260P + C302G + R336L + D379V + R454P + E457N | L181F + A237V + R480K and/or G413L/S + H416D + E418A |
| DS57 | M192R + L260P + C302G + R336L + D379V + R454P | L181F + A237V + R480K and/or G413L/S + H416D + E418A |
| DS58 | M192R + L260P + C302G + R336L + D379V + R454A + E457L | L181F + A237V + R480K and/or G413L/S + H416D + E418A |
| DS59 | M192R + L260P + C302G + R336L + D379V + R454A + E457N | L181F + A237V + R480K and/or G413L/S + H416D + E418A |
| DS60 | M192R + L260P + C302G + R336L + D379V + R454A | L181F + A237V + R480K and/or G413L/S + H416D + E418A |
| DS61 | M192R + L260P + C302G + R336L + D379V + E457L | L181F + A237V + R480K and/or G413L/S + H416D + E418A |
| DS62 | M192R + L260P + C302G + R336L + D379V + E457N | L181F + A237V + R480K and/or G413L/S + H416D + E418A |
| DS63 | M192R + L260P + C302G + R336L + D379V | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS64 | M192R + L260P + C302G + R336L + R454P + E457L | L181F + A237V + R480K and/or G413L/S + H416D + E418A |
| DS65 | M192R + L260P + C302G + R336L + R454P + E457N | L181F + A237V + R480K and/or G413L/S + H416D + E418A |
| DS66 | M192R + L260P + C302G + R336L + R454P | L181F + A237V + R480K and/or G413L/S + H416D + E418A |
| DS67 | M192R + L260P + C302G + R336L + R454A + E457L | L181F + A237V + R480K and/or G413L/S + H416D + E418A |
| DS68 | M192R + L260P + C302G + R336L + R454A + E457N | L181F + A237V + R480K and/or G413L/S + H416D + E418A |
| DS69 | M192R + L260P + C302G + R336L + R454A | L181F + A237V + R480K and/or G413L/S + H416D + E418A |
| DS70 | M192R + L260P + C302G + R336L + E457L | L181F + A237V + R480K and/or G413L/S + H416D + E418A |
| DS71 | M192R + L260P + C302G + R336L + E457N | L181F + A237V + R480K and/or G413L/S + H416D + E418A |
| DS72 | M192R + L260P + C302G + R336L | L181F + A237V + R480K and/or G413L/S + H416D + E418A |
| DS73 | M192R + L260P + C302G + R336N + D379V + R454P + E457L | L181F + A237V + R480K and/or G413L/S + H416D + E418A |
| DS74 | M192R + L260P + C302G + R336N + D379V + R454P + E457N | L181F + A237V + R480K and/or G413L/S + H416D + E418A |
| DS75 | M192R + L260P + C302G + R336N + D379V + R454P | L181F + A237V + R480K and/or G413L/S + H416D + E418A |
| DS76 | M192R + L260P + C302G + R336N + D379V + R454A + E457L | L181F + A237V + R480K and/or G413L/S + H416D + E418A |
| DS77 | M192R + L260P + C302G + R336N + D379V + R454A + E457N | L181F + A237V + R480K and/or G413L/S + H416D + E418A |
| DS78 | M192R + L260P + C302G + R336N + D379V + R454A | L181F + A237V + R480K and/or G413L/S + H416D + E418A |
| DS79 | M192R + L260P + C302G + R336N + D379V + E457L | L181F + A237V + R480K and/or G413L/S + H416D + E418A |
| DS80 | M192R + L260P + C302G + R336N + D379V + E457N | L181F + A237V + R480K and/or G413L/S + H416D + E418A |
| DS81 | M192R + L260P + C302G + R336N + D379V | L181F + A237V + R480K and/or G413L/S + H416D + E418A |
| DS82 | M192R + L260P + C302G + R336N + R454P + E457L | L181F + A237V + R480K and/or G413L/S + H416D + E418A |
| DS83 | M192R + L260P + C302G + R336N + R454P + E457N | L181F + A237V + R480K and/or G413L/S + H416D + E418A |
| DS84 | M192R + L260P + C302G + R336N + R454P | L181F + A237V + R480K and/or G413L/S + H416D + E418A |
| DS85 | M192R + L260P + C302G + R336N + R454A + E457L | L181F + A237V + R480K and/or G413L/S + H416D + E418A |
| DS86 | M192R + L260P + C302G + R336N + R454A + E457N | L181F + A237V + R480K and/or G413L/S + H416D + E418A |
| DS87 | M192R + L260P + C302G + R336N + R454A | L181F + A237V + R480K and/or G413L/S + H416D + E418A |
| DS88 | M192R + L260P + C302G + R336N + E457L | L181F + A237V + R480K and/or G413L/S + H416D + E418A |
| DS89 | M192R + L260P + C302G + R336N + E457N | L181F + A237V + R480K and/or G413L/S + H416D + E418A |
| DS90 | M192R + L260P + C302G + R336N | L181F + A237V + R480K and/or G413L/S + H416D + E418A |
| DS91 | M192R + L260P + C302G + D379V + R454P + E457L | L181F + A237V + R480K and/or G413L/S + H416D + E418A |
| DS92 | M192R + L260P + C302G + D379V + R454P + E457N | L181F + A237V + R480K and/or G413L/S + H416D + E418A |
| DS93 | M192R + L260P + C302G + D379V + R454P | L181F + A237V + R480K and/or G413L/S + H416D + E418A |
| DS94 | M192R + L260P + C302G + D379V + R454A + E457L | L181F + A237V + R480K and/or G413L/S + H416D + E418A |
| DS95 | M192R + L260P + C302G + D379V + R454A + E457N | L181F + A237V + R480K and/or G413L/S + H416D + E418A |
| DS96 | M192R + L260P + C302G + D379V + R454A | L181F + A237V + R480K and/or G413L/S + H416D + E418A |
| DS97 | M192R + L260P + C302G + D379V + E457L | L181F + A237V + R480K and/or G413L/S + H416D + E418A |
| DS98 | M192R + L260P + C302G + D379V + E457N | L181F + A237V + R480K and/or G413L/S + H416D + E418A |
| DS99 | M192R + L260P + C302G + D379V | L181F + A237V + R480K and/or G413L/S + H416D + E418A |
| DS100 | M192R + L260P + C302G + R454P + E457L | L181F + A237V + R480K and/or G413L/S + H416D + E418A |
| DS101 | M192R + L260P + C302G + R454P + E457N | L181F + A237V + R480K and/or G413L/S + H416D + E418A |
| DS102 | M192R + L260P + C302G + R454P | L181F + A237V + R480K and/or G413L/S + H416D + E418A |
| DS103 | M192R + L260P + C302G + R454A + E457L | L181F + A237V + R480K and/or G413L/S + H416D + E418A |
| DS104 | M192R + L260P + C302G + R454A + E457N | L181F + A237V + R480K and/or G413L/S + H416D + E418A |
| DS105 | M192R + L260P + C302G + R454A | L181F + A237V + R480K and/or G413L/S + H416D + E418A |
| DS106 | M192R + L260P + C302G + E457L | L181F + A237V + R480K and/or G413L/S + H416D + E418A |
| DS107 | M192R + L260P + C302G + E457N | L181F + A237V + R480K and/or G413L/S + H416D + E418A |
| DS108 | M192R + L260P + C302G | L181F + A237V + R480K and/or G413L/S + H416D + E418A |
| DS163 | M192R + C302R + R336L + D379V + R454P + E457L | L181F + A237V + R480K and/or G413L/S + H416D + E418A |
| DS164 | M192R + C302R + R336L + D379V + R454P + E457N | L181F + A237V + R480K and/or G413L/S + H416D + E418A |
| DS165 | M192R + C302R + R336L + D379V + R454P | L181F + A237V + R480K and/or G413L/S + H416D + E418A |
| DS166 | M192R + C302R + R336L + D379V + R454A + E457L | L181F + A237V + R480K and/or G413L/S + H416D + E418A |
| DS167 | M192R + C302R + R336L + D379V + R454A + E457N | L181F + A237V + R480K and/or G413L/S + H416D + E418A |
| DS168 | M192R + C302R + R336L + D379V + R454A | L181F + A237V + R480K and/or G413L/S + H416D + E418A |
| DS169 | M192R + C302R + R336L + D379V + E457L | L181F + A237V + R480K and/or G413L/S + H416D + E418A |
| DS170 | M192R + C302R + R336L + D379V + E457N | L181F + A237V + R480K and/or G413L/S + H416D + E418A |
| DS171 | M192R + C302R + R336L + D379V | L181F + A237V + R480K and/or G413L/S + H416D + E418A |
| DS172 | M192R + C302R + R336L + R454P + E457L | L181F + A237V + R480K and/or G413L/S + H416D + E418A |
| DS173 | M192R + C302R + R336L + R454P + E457N | L181F + A237V + R480K and/or G413L/S + H416D + E418A |
| DS174 | M192R + C302R + R336L + R454P | L181F + A237V + R480K and/or G413L/S + H416D + E418A |
| DS175 | M192R + C302R + R336L + R454A + E457L | L181F + A237V + R480K and/or G413L/S + H416D + E418A |
| DS176 | M192R + C302R + R336L + R454A + E457N | L181F + A237V + R480K and/or G413L/S + H416D + E418A |
| DS177 | M192R + C302R + R336L + R454A | L181F + A237V + R480K and/or G413L/S + H416D + E418A |
| DS178 | M192R + C302R + R336L + E457L | L181F + A237V + R480K and/or G413L/S + H416D + E418A |
| DS179 | M192R + C302R + R336L + E457N | L181F + A237V + R480K and/or G413L/S + H416D + E418A |
| DS180 | M192R + C302R + R336L | L181F + A237V + R480K and/or G413L/S + H416D + E418A |
| DS181 | M192R + C302R + R336N + D379V + R454P + E457L | L181F + A237V + R480K and/or G413L/S + H416D + E418A |
| DS182 | M192R + C302R + R336N + D379V + R454P + E457N | L181F + A237V + R480K and/or G413L/S + H416D + E418A |
| DS183 | M192R + C302R + R336N + D379V + R454P | L181F + A237V + R480K and/or G413L/S + H416D + E418A |
| DS184 | M192R + C302R + R336N + D379V + R454A + E457L | L181F + A237V + R480K and/or G413L/S + H416D + E418A |
| DS185 | M192R + C302R + R336N + D379V + R454A + E457N | L181F + A237V + R480K and/or G413L/S + H416D + E418A |
| DS186 | M192R + C302R + R336N + D379V + R454A | L181F + A237V + R480K and/or G413L/S + H416D + E418A |
| DS187 | M192R + C302R + R336N + D379V + E457L | L181F + A237V + R480K and/or G413L/S + H416D + E418A |
| DS188 | M192R + C302R + R336N + D379V + E457N | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
| --- | --- | --- |
| DS189 | M192R + C302R + R336N + D379V | L181F + A237V + R480K and/or G413L/S + H416D + E418A |
| DS190 | M192R + C302R + R336N + R454P + E457L | L181F + A237V + R480K and/or G413L/S + H416D + E418A |
| DS191 | M192R + C302R + R336N + R454P + E457N | L181F + A237V + R480K and/or G413L/S + H416D + E418A |
| DS192 | M192R + C302R + R336N + R454P | L181F + A237V + R480K and/or G413L/S + H416D + E418A |
| DS193 | M192R + C302R + R336N + R454A + E457L | L181F + A237V + R480K and/or G413L/S + H416D + E418A |
| DS194 | M192R + C302R + R336N + R454A + E457N | L181F + A237V + R480K and/or G413L/S + H416D + E418A |
| DS195 | M192R + C302R + R336N + R454A | L181F + A237V + R480K and/or G413L/S + H416D + E418A |
| DS196 | M192R + C302R + R336N + E457L | L181F + A237V + R480K and/or G413L/S + H416D + E418A |
| DS197 | M192R + C302R + R336N + E457N | L181F + A237V + R480K and/or G413L/S + H416D + E418A |
| DS198 | M192R + C302R + R336N | L181F + A237V + R480K and/or G413L/S + H416D + E418A |
| DS199 | M192R + C302R + D379V + R454P + E457L | L181F + A237V + R480K and/or G413L/S + H416D + E418A |
| DS200 | M192R + C302R + D379V + R454P + E457N | L181F + A237V + R480K and/or G413L/S + H416D + E418A |
| DS201 | M192R + C302R + D379V + R454P | L181F + A237V + R480K and/or G413L/S + H416D + E418A |
| DS202 | M192R + C302R + D379V + R454A + E457L | L181F + A237V + R480K and/or G413L/S + H416D + E418A |
| DS203 | M192R + C302R + D379V + R454A + E457N | L181F + A237V + R480K and/or G413L/S + H416D + E418A |
| DS204 | M192R + C302R + D379V + R454A | L181F + A237V + R480K and/or G413L/S + H416D + E418A |
| DS205 | M192R + C302R + D379V + E457L | L181F + A237V + R480K and/or G413L/S + H416D + E418A |
| DS206 | M192R + C302R + D379V + E457N | L181F + A237V + R480K and/or G413L/S + H416D + E418A |
| DS207 | M192R + C302R + D379V | L181F + A237V + R480K and/or G413L/S + H416D + E418A |
| DS208 | M192R + C302R + R454P + E457L | L181F + A237V + R480K and/or G413L/S + H416D + E418A |
| DS209 | M192R + C302R + R454P + E457N | L181F + A237V + R480K and/or G413L/S + H416D + E418A |
| DS210 | M192R + C302R + R454P | L181F + A237V + R480K and/or G413L/S + H416D + E418A |
| DS211 | M192R + C302R + R454A + E457L | L181F + A237V + R480K and/or G413L/S + H416D + E418A |
| DS212 | M192R + C302R + R454A + E457N | L181F + A237V + R480K and/or G413L/S + H416D + E418A |
| DS213 | M192R + C302R + R454A | L181F + A237V + R480K and/or G413L/S + H416D + E418A |
| DS214 | M192R + C302R + E457L | L181F + A237V + R480K and/or G413L/S + H416D + E418A |
| DS215 | M192R + C302R + E457N | L181F + A237V + R480K and/or G413L/S + H416D + E418A |
| DS216 | M192R + C302R | L181F + A237V + R480K and/or G413L/S + H416D + E418A |
| DS217 | M192R + C302G + R336L + D379V + R454P + E457L | L181F + A237V + R480K and/or G413L/S + H416D + E418A |
| DS218 | M192R + C302G + R336L + D379V + R454P + E457N | L181F + A237V + R480K and/or G413L/S + H416D + E418A |
| DS219 | M192R + C302G + R336L + D379V + R454P | L181F + A237V + R480K and/or G413L/S + H416D + E418A |
| DS220 | M192R + C302G + R336L + D379V + R454A + E457L | L181F + A237V + R480K and/or G413L/S + H416D + E418A |
| DS221 | M192R + C302G + R336L + D379V + R454A + E457N | L181F + A237V + R480K and/or G413L/S + H416D + E418A |
| DS222 | M192R + C302G + R336L + D379V + R454A | L181F + A237V + R480K and/or G413L/S + H416D + E418A |
| DS223 | M192R + C302G + R336L + D379V + E457L | L181F + A237V + R480K and/or G413L/S + H416D + E418A |
| DS224 | M192R + C302G + R336L + D379V + E457N | L181F + A237V + R480K and/or G413L/S + H416D + E418A |
| DS225 | M192R + C302G + R336L + D379V | L181F + A237V + R480K and/or G413L/S + H416D + E418A |
| DS226 | M192R + C302G + R336L + R454P + E457L | L181F + A237V + R480K and/or G413L/S + H416D + E418A |
| DS227 | M192R + C302G + R336L + R454P + E457N | L181F + A237V + R480K and/or G413L/S + H416D + E418A |
| DS228 | M192R + C302G + R336L + R454P | L181F + A237V + R480K and/or G413L/S + H416D + E418A |
| DS229 | M192R + C302G + R336L + R454A + E457L | L181F + A237V + R480K and/or G413L/S + H416D + E418A |
| DS230 | M192R + C302G + R336L + R454A + E457N | L181F + A237V + R480K and/or G413L/S + H416D + E418A |
| DS231 | M192R + C302G + R336L + R454A | L181F + A237V + R480K and/or G413L/S + H416D + E418A |
| DS232 | M192R + C302G + R336L + E457L | L181F + A237V + R480K and/or G413L/S + H416D + E418A |
| DS233 | M192R + C302G + R336L + E457N | L181F + A237V + R480K and/or G413L/S + H416D + E418A |
| DS234 | M192R + C302G + R336L | L181F + A237V + R480K and/or G413L/S + H416D + E418A |
| DS235 | M192R + C302G + R336N + D379V + R454P + E457L | L181F + A237V + R480K and/or G413L/S + H416D + E418A |
| DS236 | M192R + C302G + R336N + D379V + R454P + E457N | L181F + A237V + R480K and/or G413L/S + H416D + E418A |
| DS237 | M192R + C302G + R336N + D379V + R454P | L181F + A237V + R480K and/or G413L/S + H416D + E418A |
| DS238 | M192R + C302G + R336N + D379V + R454A + E457L | L181F + A237V + R480K and/or G413L/S + H416D + E418A |
| DS239 | M192R + C302G + R336N + D379V + R454A + E457N | L181F + A237V + R480K and/or G413L/S + H416D + E418A |
| DS240 | M192R + C302G + R336N + D379V + R454A | L181F + A237V + R480K and/or G413L/S + H416D + E418A |
| DS241 | M192R + C302G + R336N + D379V + E457L | L181F + A237V + R480K and/or G413L/S + H416D + E418A |
| DS242 | M192R + C302G + R336N + D379V + E457N | L181F + A237V + R480K and/or G413L/S + H416D + E418A |
| DS243 | M192R + C302G + R336N + D379V | L181F + A237V + R480K and/or G413L/S + H416D + E418A |
| DS244 | M192R + C302G + R336N + R454P + E457L | L181F + A237V + R480K and/or G413L/S + H416D + E418A |
| DS245 | M192R + C302G + R336N + R454P + E457N | L181F + A237V + R480K and/or G413L/S + H416D + E418A |
| DS246 | M192R + C302G + R336N + R454P | L181F + A237V + R480K and/or G413L/S + H416D + E418A |
| DS247 | M192R + C302G + R336N + R454A + E457L | L181F + A237V + R480K and/or G413L/S + H416D + E418A |
| DS248 | M192R + C302G + R336N + R454A + E457N | L181F + A237V + R480K and/or G413L/S + H416D + E418A |
| DS249 | M192R + C302G + R336N + R454A | L181F + A237V + R480K and/or G413L/S + H416D + E418A |
| DS250 | M192R + C302G + R336N + E457L | L181F + A237V + R480K and/or G413L/S + H416D + E418A |
| DS251 | M192R + C302G + R336N + E457N | L181F + A237V + R480K and/or G413L/S + H416D + E418A |
| DS252 | M192R + C302G + R336N | L181F + A237V + R480K and/or G413L/S + H416D + E418A |
| DS253 | M192R + C302G + D379V + R454P + E457L | L181F + A237V + R480K and/or G413L/S + H416D + E418A |
| DS254 | M192R + C302G + D379V + R454P + E457N | L181F + A237V + R480K and/or G413L/S + H416D + E418A |
| DS255 | M192R + C302G + D379V + R454P | L181F + A237V + R480K and/or G413L/S + H416D + E418A |
| DS256 | M192R + C302G + D379V + R454A + E457L | L181F + A237V + R480K and/or G413L/S + H416D + E418A |
| DS257 | M192R + C302G + D379V + R454A + E457N | L181F + A237V + R480K and/or G413L/S + H416D + E418A |
| DS258 | M192R + C302G + D379V + R454A | L181F + A237V + R480K and/or G413L/S + H416D + E418A |
| DS259 | M192R + C302G + D379V + E457L | L181F + A237V + R480K and/or G413L/S + H416D + E418A |
| DS260 | M192R + C302G + D379V + E457N | L181F + A237V + R480K and/or G413L/S + H416D + E418A |
| DS261 | M192R + C302G + D379V | L181F + A237V + R480K and/or G413L/S + H416D + E418A |
| DS262 | M192R + C302G + R454P + E457L | L181F + A237V + R480K and/or G413L/S + H416D + E418A |
| DS263 | M192R + C302G + R454P + E457N | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS264 | M192R + C302G + R454P | L181F + A237V + R480K and/or G413L/S + H416D + E418A |
| DS265 | M192R + C302G + R454A + E457L | L181F + A237V + R480K and/or G413L/S + H416D + E418A |
| DS266 | M192R + C302G + R454A + E457N | L181F + A237V + R480K and/or G413L/S + H416D + E418A |
| DS267 | M192R + C302G + R454A | L181F + A237V + R480K and/or G413L/S + H416D + E418A |
| DS268 | M192R + C302G + E457L | L181F + A237V + R480K and/or G413L/S + H416D + E418A |
| DS269 | M192R + C302G + E457N | L181F + A237V + R480K and/or G413L/S + H416D + E418A |
| DS270 | M192R + C302G | L181F + A237V + R480K and/or G413L/S + H416D + E418A |
| DS325 | M1920 + L260P + C302R + R336L + D379V + R454P + E457L | L181F + A237V + R480K and/or G413L/S + H416D + E418A |
| DS326 | M1920 + L260P + C302R + R336L + D379V + R454P + E457N | L181F + A237V + R480K and/or G413L/S + H416D + E418A |
| DS327 | M1920 + L260P + C302R + R336L + D379V + R454P | L181F + A237V + R480K and/or G413L/S + H416D + E418A |
| DS328 | M1920 + L260P + C302R + R336L + D379V + R454A + E457L | L181F + A237V + R480K and/or G413L/S + H416D + E418A |
| DS329 | M1920 + L260P + C302R + R336L + D379V + R454A + E457N | L181F + A237V + R480K and/or G413L/S + H416D + E418A |
| DS330 | M1920 + L260P + C302R + R336L + D379V + R454A | L181F + A237V + R480K and/or G413L/S + H416D + E418A |
| DS331 | M1920 + L260P + C302R + R336L + D379V + E457L | L181F + A237V + R480K and/or G413L/S + H416D + E418A |
| DS332 | M1920 + L260P + C302R + R336L + D379V + E457N | L181F + A237V + R480K and/or G413L/S + H416D + E418A |
| DS333 | M1920 + L260P + C302R + R336L + D379V | L181F + A237V + R480K and/or G413L/S + H416D + E418A |
| DS334 | M1920 + L260P + C302R + R336L + R454P + E457L | L181F + A237V + R480K and/or G413L/S + H416D + E418A |
| DS335 | M1920 + L260P + C302R + R336L + R454P + E457N | L181F + A237V + R480K and/or G413L/S + H416D + E418A |
| DS336 | M1920 + L260P + C302R + R336L + R454P | L181F + A237V + R480K and/or G413L/S + H416D + E418A |
| DS337 | M1920 + L260P + C302R + R336L + R454A + E457L | L181F + A237V + R480K and/or G413L/S + H416D + E418A |
| DS338 | M1920 + L260P + C302R + R336L + R454A + E457N | L181F + A237V + R480K and/or G413L/S + H416D + E418A |
| DS339 | M1920 + L260P + C302R + R336L + R454A | L181F + A237V + R480K and/or G413L/S + H416D + E418A |
| DS340 | M1920 + L260P + C302R + R336L + E457L | L181F + A237V + R480K and/or G413L/S + H416D + E418A |
| DS341 | M1920 + L260P + C302R + R336L + E457N | L181F + A237V + R480K and/or G413L/S + H416D + E418A |
| DS342 | M1920 + L260P + C302R + R336L | L181F + A237V + R480K and/or G413L/S + H416D + E418A |
| DS343 | M1920 + L260P + C302R + R336N + D379V + R454P + E457L | L181F + A237V + R480K and/or G413L/S + H416D + E418A |
| DS344 | M1920 + L260P + C302R + R336N + D379V + R454P + E457N | L181F + A237V + R480K and/or G413L/S + H416D + E418A |
| DS345 | M1920 + L260P + C302R + R336N + D379V + R454P | L181F + A237V + R480K and/or G413L/S + H416D + E418A |
| DS346 | M1920 + L260P + C302R + R336N + D379V + R454A + E457L | L181F + A237V + R480K and/or G413L/S + H416D + E418A |
| DS347 | M1920 + L260P + C302R + R336N + D379V + R454A + E457N | L181F + A237V + R480K and/or G413L/S + H416D + E418A |
| DS348 | M1920 + L260P + C302R + R336N + D379V + R454A | L181F + A237V + R480K and/or G413L/S + H416D + E418A |
| DS349 | M1920 + L260P + C302R + R336N + D379V + E457L | L181F + A237V + R480K and/or G413L/S + H416D + E418A |
| DS350 | M1920 + L260P + C302R + R336N + D379V + E457N | L181F + A237V + R480K and/or G413L/S + H416D + E418A |
| DS351 | M1920 + L260P + C302R + R336N + D379V | L181F + A237V + R480K and/or G413L/S + H416D + E418A |
| DS352 | M1920 + L260P + C302R + R336N + R454P + E457L | L181F + A237V + R480K and/or G413L/S + H416D + E418A |
| DS353 | M1920 + L260P + C302R + R336N + R454P + E457N | L181F + A237V + R480K and/or G413L/S + H416D + E418A |
| DS354 | M1920 + L260P + C302R + R336N + R454P | L181F + A237V + R480K and/or G413L/S + H416D + E418A |
| DS355 | M1920 + L260P + C302R + R336N + R454A + E457L | L181F + A237V + R480K and/or G413L/S + H416D + E418A |
| DS356 | M1920 + L260P + C302R + R336N + R454A + E457N | L181F + A237V + R480K and/or G413L/S + H416D + E418A |
| DS357 | M1920 + L260P + C302R + R336N + R454A | L181F + A237V + R480K and/or G413L/S + H416D + E418A |
| DS358 | M1920 + L260P + C302R + R336N + E457L | L181F + A237V + R480K and/or G413L/S + H416D + E418A |
| DS359 | M1920 + L260P + C302R + R336N + E457N | L181F + A237V + R480K and/or G413L/S + H416D + E418A |
| DS360 | M1920 + L260P + C302R + R336N | L181F + A237V + R480K and/or G413L/S + H416D + E418A |
| DS361 | M1920 + L260P + C302R + D379V + R454P + E457L | L181F + A237V + R480K and/or G413L/S + H416D + E418A |
| DS362 | M1920 + L260P + C302R + D379V + R454P + E457N | L181F + A237V + R480K and/or G413L/S + H416D + E418A |
| DS363 | M1920 + L260P + C302R + D379V + R454P | L181F + A237V + R480K and/or G413L/S + H416D + E418A |
| DS364 | M1920 + L260P + C302R + D379V + R454A + E457L | L181F + A237V + R480K and/or G413L/S + H416D + E418A |
| DS365 | M1920 + L260P + C302R + D379V + R454A + E457N | L181F + A237V + R480K and/or G413L/S + H416D + E418A |
| DS366 | M1920 + L260P + C302R + D379V + R454A | L181F + A237V + R480K and/or G413L/S + H416D + E418A |
| DS367 | M1920 + L260P + C302R + D379V + E457L | L181F + A237V + R480K and/or G413L/S + H416D + E418A |
| DS368 | M1920 + L260P + C302R + D379V + E457N | L181F + A237V + R480K and/or G413L/S + H416D + E418A |
| DS369 | M1920 + L260P + C302R + D379V | L181F + A237V + R480K and/or G413L/S + H416D + E418A |
| DS370 | M1920 + L260P + C302R + R454P + E457L | L181F + A237V + R480K and/or G413L/S + H416D + E418A |
| DS371 | M1920 + L260P + C302R + R454P + E457N | L181F + A237V + R480K and/or G413L/S + H416D + E418A |
| DS372 | M1920 + L260P + C302R + R454P | L181F + A237V + R480K and/or G413L/S + H416D + E418A |
| DS373 | M1920 + L260P + C302R + R454A + E457L | L181F + A237V + R480K and/or G413L/S + H416D + E418A |
| DS374 | M1920 + L260P + C302R + R454A + E457N | L181F + A237V + R480K and/or G413L/S + H416D + E418A |
| DS375 | M1920 + L260P + C302R + R454A | L181F + A237V + R480K and/or G413L/S + H416D + E418A |
| DS376 | M1920 + L260P + C302R + E457L | L181F + A237V + R480K and/or G413L/S + H416D + E418A |
| DS377 | M1920 + L260P + C302R + E457N | L181F + A237V + R480K and/or G413L/S + H416D + E418A |
| DS378 | M1920 + L260P + C302R | L181F + A237V + R480K and/or G413L/S + H416D + E418A |
| DS379 | M1920 + L260P + C302G + R336L + D379V + R454P + E457L | L181F + A237V + R480K and/or G413L/S + H416D + E418A |
| DS380 | M1920 + L260P + C302G + R336L + D379V + R454P + E457N | L181F + A237V + R480K and/or G413L/S + H416D + E418A |
| DS381 | M1920 + L260P + C302G + R336L + D379V + R454P | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS382 | M1920 + L260P + C302G + R336L + D379V + R454A + E457L | L181F + A237V + R480K and/or G413L/S + H416D + E418A |
| DS383 | M1920 + L260P + C302G + R336L + D379V + R454A + E457N | L181F + A237V + R480K and/or G413L/S + H416D + E418A |
| DS384 | M1920 + L260P + C302G + R336L + D379V + R454A | L181F + A237V + R480K and/or G413L/S + H416D + E418A |
| DS385 | M1920 + L260P + C302G + R336L + D379V + E457L | L181F + A237V + R480K and/or G413L/S + H416D + E418A |
| DS386 | M1920 + L260P + C302G + R336L + D379V + E457N | L181F + A237V + R480K and/or G413L/S + H416D + E418A |
| DS387 | M1920 + L260P + C302G + R336L + D379V | L181F + A237V + R480K and/or G413L/S + H416D + E418A |
| DS388 | M1920 + L260P + C302G + R336L + R454P + E457L | L181F + A237V + R480K and/or G413L/S + H416D + E418A |
| DS389 | M1920 + L260P + C302G + R336L + R454P + E457N | L181F + A237V + R480K and/or G413L/S + H416D + E418A |
| DS390 | M1920 + L260P + C302G + R336L + R454P | L181F + A237V + R480K and/or G413L/S + H416D + E418A |
| DS391 | M1920 + L260P + C302G + R336L + R454A + E457L | L181F + A237V + R480K and/or G413L/S + H416D + E418A |
| DS392 | M1920 + L260P + C302G + R336L + R454A + E457N | L181F + A237V + R480K and/or G413L/S + H416D + E418A |
| DS393 | M1920 + L260P + C302G + R336L + R454A | L181F + A237V + R480K and/or G413L/S + H416D + E418A |
| DS394 | M1920 + L260P + C302G + R336L + E457L | L181F + A237V + R480K and/or G413L/S + H416D + E418A |
| DS395 | M1920 + L260P + C302G + R336L + E457N | L181F + A237V + R480K and/or G413L/S + H416D + E418A |
| DS396 | M1920 + L260P + C302G + R336L | L181F + A237V + R480K and/or G413L/S + H416D + E418A |
| DS397 | M1920 + L260P + C302G + R336N + D379V + R454P + E457L | L181F + A237V + R480K and/or G413L/S + H416D + E418A |
| DS398 | M1920 + L260P + C302G + R336N + D379V + R454P + E457N | L181F + A237V + R480K and/or G413L/S + H416D + E418A |
| DS399 | M1920 + L260P + C302G + R336N + D379V + R454P | L181F + A237V + R480K and/or G413L/S + H416D + E418A |
| DS400 | M1920 + L260P + C302G + R336N + D379V + R454A + E457L | L181F + A237V + R480K and/or G413L/S + H416D + E418A |
| DS401 | M1920 + L260P + C302G + R336N + D379V + R454A + E457N | L181F + A237V + R480K and/or G413L/S + H416D + E418A |
| DS402 | M1920 + L260P + C302G + R336N + D379V + R454A | L181F + A237V + R480K and/or G413L/S + H416D + E418A |
| DS403 | M1920 + L260P + C302G + R336N + D379V + E457L | L181F + A237V + R480K and/or G413L/S + H416D + E418A |
| DS404 | M1920 + L260P + C302G + R336N + D379V + E457N | L181F + A237V + R480K and/or G413L/S + H416D + E418A |
| DS405 | M1920 + L260P + C302G + R336N + D379V | L181F + A237V + R480K and/or G413L/S + H416D + E418A |
| DS406 | M1920 + L260P + C302G + R336N + R454P + E457L | L181F + A237V + R480K and/or G413L/S + H416D + E418A |
| DS407 | M1920 + L260P + C302G + R336N + R454P + E457N | L181F + A237V + R480K and/or G413L/S + H416D + E418A |
| DS408 | M1920 + L260P + C302G + R336N + R454P | L181F + A237V + R480K and/or G413L/S + H416D + E418A |
| DS409 | M1920 + L260P + C302G + R336N + R454A + E457L | L181F + A237V + R480K and/or G413L/S + H416D + E418A |
| DS410 | M1920 + L260P + C302G + R336N + R454A + E457N | L181F + A237V + R480K and/or G413L/S + H416D + E418A |
| DS411 | M1920 + L260P + C302G + R336N + R454A | L181F + A237V + R480K and/or G413L/S + H416D + E418A |
| DS412 | M1920 + L260P + C302G + R336N + E457L | L181F + A237V + R480K and/or G413L/S + H416D + E418A |
| DS413 | M1920 + L260P + C302G + R336N + E457N | L181F + A237V + R480K and/or G413L/S + H416D + E418A |
| DS414 | M1920 + L260P + C302G + R336N | L181F + A237V + R480K and/or G413L/S + H416D + E418A |
| DS415 | M1920 + L260P + C302G + D379V + R454P + E457L | L181F + A237V + R480K and/or G413L/S + H416D + E418A |
| DS416 | M1920 + L260P + C302G + D379V + R454P + E457N | L181F + A237V + R480K and/or G413L/S + H416D + E418A |
| DS417 | M1920 + L260P + C302G + D379V + R454P | L181F + A237V + R480K and/or G413L/S + H416D + E418A |
| DS418 | M1920 + L260P + C302G + D379V + R454A + E457L | L181F + A237V + R480K and/or G413L/S + H416D + E418A |
| DS419 | M1920 + L260P + C302G + D379V + R454A + E457N | L181F + A237V + R480K and/or G413L/S + H416D + E418A |
| DS420 | M1920 + L260P + C302G + D379V + R454A | L181F + A237V + R480K and/or G413L/S + H416D + E418A |
| DS421 | M1920 + L260P + C302G + D379V + E457L | L181F + A237V + R480K and/or G413L/S + H416D + E418A |
| DS422 | M1920 + L260P + C302G + D379V + E457N | L181F + A237V + R480K and/or G413L/S + H416D + E418A |
| DS423 | M1920 + L260P + C302G + D379V | L181F + A237V + R480K and/or G413L/S + H416D + E418A |
| DS424 | M1920 + L260P + C302G + R454P + E457L | L181F + A237V + R480K and/or G413L/S + H416D + E418A |
| DS425 | M1920 + L260P + C302G + R454P + E457N | L181F + A237V + R480K and/or G413L/S + H416D + E418A |
| DS426 | M1920 + L260P + C302G + R454P | L181F + A237V + R480K and/or G413L/S + H416D + E418A |
| DS427 | M1920 + L260P + C302G + R454A + E457L | L181F + A237V + R480K and/or G413L/S + H416D + E418A |
| DS428 | M1920 + L260P + C302G + R454A + E457N | L181F + A237V + R480K and/or G413L/S + H416D + E418A |
| DS429 | M1920 + L260P + C302G + R454A | L181F + A237V + R480K and/or G413L/S + H416D + E418A |
| DS430 | M1920 + L260P + C302G + E457L | L181F + A237V + R480K and/or G413L/S + H416D + E418A |
| DS431 | M1920 + L260P + C302G + E457N | L181F + A237V + R480K and/or G413L/S + H416D + E418A |
| DS432 | M1920 + L260P + C302G | L181F + A237V + R480K and/or G413L/S + H416D + E418A |
| DS487 | M1920 + C302R + R336L + D379V + R454P + E457L | L181F + A237V + R480K and/or G413L/S + H416D + E418A |
| DS488 | M1920 + C302R + R336L + D379V + R454P + E457N | L181F + A237V + R480K and/or G413L/S + H416D + E418A |
| DS489 | M1920 + C302R + R336L + D379V + R454P | L181F + A237V + R480K and/or G413L/S + H416D + E418A |
| DS490 | M1920 + C302R + R336L + D379V + R454A + E457L | L181F + A237V + R480K and/or G413L/S + H416D + E418A |
| DS491 | M1920 + C302R + R336L + D379V + R454A + E457N | L181F + A237V + R480K and/or G413L/S + H416D + E418A |
| DS492 | M1920 + C302R + R336L + D379V + R454A | L181F + A237V + R480K and/or G413L/S + H416D + E418A |
| DS493 | M1920 + C302R + R336L + D379V + E457L | L181F + A237V + R480K and/or G413L/S + H416D + E418A |
| DS494 | M1920 + C302R + R336L + D379V + E457N | L181F + A237V + R480K and/or G413L/S + H416D + E418A |
| DS495 | M1920 + C302R + R336L + D379V | L181F + A237V + R480K and/or G413L/S + H416D + E418A |
| DS496 | M1920 + C302R + R336L + R454P + E457L | L181F + A237V + R480K and/or G413L/S + H416D + E418A |
| DS497 | M1920 + C302R + R336L + R454P + E457N | L181F + A237V + R480K and/or G413L/S + H416D + E418A |
| DS498 | M1920 + C302R + R336L + R454P | L181F + A237V + R480K and/or G413L/S + H416D + E418A |
| DS499 | M1920 + C302R + R336L + R454A + E457L | L181F + A237V + R480K and/or G413L/S + H416D + E418A |
| DS500 | M1920 + C302R + R336L + R454A + E457N | L181F + A237V + R480K and/or G413L/S + H416D + E418A |
| DS501 | M1920 + C302R + R336L + R454A | L181F + A237V + R480K and/or G413L/S + H416D + E418A |
| DS502 | M1920 + C302R + R336L + E457L | L181F + A237V + R480K and/or G413L/S + H416D + E418A |
| DS503 | M1920 + C302R + R336L + E457N | L181F + A237V + R480K and/or G413L/S + H416D + E418A |
| DS504 | M1920 + C302R + R336L | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS505 | M1920 + C302R + R336N + D379V + R454P + E457L | L181F + A237V + R480K and/or G413L/S + H416D + E418A |
| DS506 | M1920 + C302R + R336N + D379V + R454P + E457N | L181F + A237V + R480K and/or G413L/S + H416D + E418A |
| DS507 | M1920 + C302R + R336N + D379V + R454P | L181F + A237V + R480K and/or G413L/S + H416D + E418A |
| DS508 | M1920 + C302R + R336N + D379V + R454A + E457L | L181F + A237V + R480K and/or G413L/S + H416D + E418A |
| DS509 | M1920 + C302R + R336N + D379V + R454A + E457N | L181F + A237V + R480K and/or G413L/S + H416D + E418A |
| DS510 | M1920 + C302R + R336N + D379V + R454A | L181F + A237V + R480K and/or G413L/S + H416D + E418A |
| DS511 | M1920 + C302R + R336N + D379V + E457L | L181F + A237V + R480K and/or G413L/S + H416D + E418A |
| DS512 | M1920 + C302R + R336N + D379V + E457N | L181F + A237V + R480K and/or G413L/S + H416D + E418A |
| DS513 | M1920 + C302R + R336N + D379V | L181F + A237V + R480K and/or G413L/S + H416D + E418A |
| DS514 | M1920 + C302R + R336N + R454P + E457L | L181F + A237V + R480K and/or G413L/S + H416D + E418A |
| DS515 | M1920 + C302R + R336N + R454P + E457N | L181F + A237V + R480K and/or G413L/S + H416D + E418A |
| DS516 | M1920 + C302R + R336N + R454P | L181F + A237V + R480K and/or G413L/S + H416D + E418A |
| DS517 | M1920 + C302R + R336N + R454A + E457L | L181F + A237V + R480K and/or G413L/S + H416D + E418A |
| DS518 | M1920 + C302R + R336N + R454A + E457N | L181F + A237V + R480K and/or G413L/S + H416D + E418A |
| DS519 | M1920 + C302R + R336N + R454A | L181F + A237V + R480K and/or G413L/S + H416D + E418A |
| DS520 | M1920 + C302R + R336N + E457L | L181F + A237V + R480K and/or G413L/S + H416D + E418A |
| DS521 | M1920 + C302R + R336N + E457N | L181F + A237V + R480K and/or G413L/S + H416D + E418A |
| DS522 | M1920 + C302R + R336N | L181F + A237V + R480K and/or G413L/S + H416D + E418A |
| DS523 | M1920 + C302R + D379V + R454P + E457L | L181F + A237V + R480K and/or G413L/S + H416D + E418A |
| DS524 | M1920 + C302R + D379V + R454P + E457N | L181F + A237V + R480K and/or G413L/S + H416D + E418A |
| DS525 | M1920 + C302R + D379V + R454P | L181F + A237V + R480K and/or G413L/S + H416D + E418A |
| DS526 | M1920 + C302R + D379V + R454A + E457L | L181F + A237V + R480K and/or G413L/S + H416D + E418A |
| DS527 | M1920 + C302R + D379V + R454A + E457N | L181F + A237V + R480K and/or G413L/S + H416D + E418A |
| DS528 | M1920 + C302R + D379V + R454A | L181F + A237V + R480K and/or G413L/S + H416D + E418A |
| DS529 | M1920 + C302R + D379V + E457L | L181F + A237V + R480K and/or G413L/S + H416D + E418A |
| DS530 | M1920 + C302R + D379V + E457N | L181F + A237V + R480K and/or G413L/S + H416D + E418A |
| DS531 | M1920 + C302R + D379V | L181F + A237V + R480K and/or G413L/S + H416D + E418A |
| DS532 | M1920 + C302R + R454P + E457L | L181F + A237V + R480K and/or G413L/S + H416D + E418A |
| DS533 | M1920 + C302R + R454P + E457N | L181F + A237V + R480K and/or G413L/S + H416D + E418A |
| DS534 | M1920 + C302R + R454P | L181F + A237V + R480K and/or G413L/S + H416D + E418A |
| DS535 | M1920 + C302R + R454A + E457L | L181F + A237V + R480K and/or G413L/S + H416D + E418A |
| DS536 | M1920 + C302R + R454A + E457N | L181F + A237V + R480K and/or G413L/S + H416D + E418A |
| DS537 | M1920 + C302R + R454A | L181F + A237V + R480K and/or G413L/S + H416D + E418A |
| DS538 | M1920 + C302R + E457L | L181F + A237V + R480K and/or G413L/S + H416D + E418A |
| DS539 | M1920 + C302R + E457N | L181F + A237V + R480K and/or G413L/S + H416D + E418A |
| DS540 | M1920 + C302R | L181F + A237V + R480K and/or G413L/S + H416D + E418A |
| DS541 | M1920 + C302G + R336L + D379V + R454P + E457L | L181F + A237V + R480K and/or G413L/S + H416D + E418A |
| DS542 | M1920 + C302G + R336L + D379V + R454P + E457N | L181F + A237V + R480K and/or G413L/S + H416D + E418A |
| DS543 | M1920 + C302G + R336L + D379V + R454P | L181F + A237V + R480K and/or G413L/S + H416D + E418A |
| DS544 | M1920 + C302G + R336L + D379V + R454A + E457L | L181F + A237V + R480K and/or G413L/S + H416D + E418A |
| DS545 | M1920 + C302G + R336L + D379V + R454A + E457N | L181F + A237V + R480K and/or G413L/S + H416D + E418A |
| DS546 | M1920 + C302G + R336L + D379V + R454A | L181F + A237V + R480K and/or G413L/S + H416D + E418A |
| DS547 | M1920 + C302G + R336L + D379V + E457L | L181F + A237V + R480K and/or G413L/S + H416D + E418A |
| DS548 | M1920 + C302G + R336L + D379V + E457N | L181F + A237V + R480K and/or G413L/S + H416D + E418A |
| DS549 | M1920 + C302G + R336L + D379V | L181F + A237V + R480K and/or G413L/S + H416D + E418A |
| DS550 | M1920 + C302G + R336L + R454P + E457L | L181F + A237V + R480K and/or G413L/S + H416D + E418A |
| DS551 | M1920 + C302G + R336L + R454P + E457N | L181F + A237V + R480K and/or G413L/S + H416D + E418A |
| DS552 | M1920 + C302G + R336L + R454P | L181F + A237V + R480K and/or G413L/S + H416D + E418A |
| DS553 | M1920 + C302G + R336L + R454A + E457L | L181F + A237V + R480K and/or G413L/S + H416D + E418A |
| DS554 | M1920 + C302G + R336L + R454A + E457N | L181F + A237V + R480K and/or G413L/S + H416D + E418A |
| DS555 | M1920 + C302G + R336L + R454A | L181F + A237V + R480K and/or G413L/S + H416D + E418A |
| DS556 | M1920 + C302G + R336L + E457L | L181F + A237V + R480K and/or G413L/S + H416D + E418A |
| DS557 | M1920 + C302G + R336L + E457N | L181F + A237V + R480K and/or G413L/S + H416D + E418A |
| DS558 | M1920 + C302G + R336L | L181F + A237V + R480K and/or G413L/S + H416D + E418A |
| DS559 | M1920 + C302G + R336N + D379V + R454P + E457L | L181F + A237V + R480K and/or G413L/S + H416D + E418A |
| DS560 | M1920 + C302G + R336N + D379V + R454P + E457N | L181F + A237V + R480K and/or G413L/S + H416D + E418A |
| DS561 | M1920 + C302G + R336N + D379V + R454P | L181F + A237V + R480K and/or G413L/S + H416D + E418A |
| DS562 | M1920 + C302G + R336N + D379V + R454A + E457L | L181F + A237V + R480K and/or G413L/S + H416D + E418A |
| DS563 | M1920 + C302G + R336N + D379V + R454A + E457N | L181F + A237V + R480K and/or G413L/S + H416D + E418A |
| DS564 | M1920 + C302G + R336N + D379V + R454A | L181F + A237V + R480K and/or G413L/S + H416D + E418A |
| DS565 | M1920 + C302G + R336N + D379V + E457L | L181F + A237V + R480K and/or G413L/S + H416D + E418A |
| DS566 | M1920 + C302G + R336N + D379V + E457N | L181F + A237V + R480K and/or G413L/S + H416D + E418A |
| DS567 | M1920 + C302G + R336N + D379V | L181F + A237V + R480K and/or G413L/S + H416D + E418A |
| DS568 | M1920 + C302G + R336N + R454P + E457L | L181F + A237V + R480K and/or G413L/S + H416D + E418A |
| DS569 | M1920 + C302G + R336N + R454P + E457N | L181F + A237V + R480K and/or G413L/S + H416D + E418A |
| DS570 | M1920 + C302G + R336N + R454P | L181F + A237V + R480K and/or G413L/S + H416D + E418A |
| DS571 | M1920 + C302G + R336N + R454A + E457L | L181F + A237V + R480K and/or G413L/S + H416D + E418A |
| DS572 | M1920 + C302G + R336N + R454A + E457N | L181F + A237V + R480K and/or G413L/S + H416D + E418A |
| DS573 | M1920 + C302G + R336N + R454A | L181F + A237V + R480K and/or G413L/S + H416D + E418A |
| DS574 | M1920 + C302G + R336N + E457L | L181F + A237V + R480K and/or G413L/S + H416D + E418A |
| DS575 | M1920 + C302G + R336N + E457N | L181F + A237V + R480K and/or G413L/S + H416D + E418A |
| DS576 | M1920 + C302G + R336N | L181F + A237V + R480K and/or G413L/S + H416D + E418A |
| DS577 | M1920 + C302G + D379V + R454P + E457L | L181F + A237V + R480K and/or G413L/S + H416D + E418A |
| DS578 | M1920 + C302G + D379V + R454P + E457N | L181F + A237V + R480K and/or G413L/S + H416D + E418A |
| DS579 | M1920 + C302G + D379V + R454P | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS580 | M1920 + C302G + D379V + R454A + E457L | L181F + A237V + R480K and/or G413L/S + H416D + E418A |
| DS581 | M1920 + C302G + D379V + R454A + E457N | L181F + A237V + R480K and/or G413L/S + H416D + E418A |
| DS582 | M1920 + C302G + D379V + R454A | L181F + A237V + R480K and/or G413L/S + H416D + E418A |
| DS583 | M1920 + C302G + D379V + E457L | L181F + A237V + R480K and/or G413L/S + H416D + E418A |
| DS584 | M1920 + C302G + D379V + E457N | L181F + A237V + R480K and/or G413L/S + H416D + E418A |
| DS585 | M1920 + C302G + D379V | L181F + A237V + R480K and/or G413L/S + H416D + E418A |
| DS586 | M1920 + C302G + R454P + E457L | L181F + A237V + R480K and/or G413L/S + H416D + E418A |
| DS587 | M1920 + C302G + R454P + E457N | L181F + A237V + R480K and/or G413L/S + H416D + E418A |
| DS588 | M1920 + C302G + R454P | L181F + A237V + R480K and/or G413L/S + H416D + E418A |
| DS589 | M1920 + C302G + R454A + E457L | L181F + A237V + R480K and/or G413L/S + H416D + E418A |
| DS590 | M1920 + C302G + R454A + E457N | L181F + A237V + R480K and/or G413L/S + H416D + E418A |
| DS591 | M1920 + C302G + R454A | L181F + A237V + R480K and/or G413L/S + H416D + E418A |
| DS592 | M1920 + C302G + E457L | L181F + A237V + R480K and/or G413L/S + H416D + E418A |
| DS593 | M1920 + C302G + E457N | L181F + A237V + R480K and/or G413L/S + H416D + E418A |
| DS594 | M1920 + C302G | L181F + A237V + R480K and/or G413L/S + H416D + E418A |
| DS649 | L260P + C302R + R336L + D379V + R454P + E457L | L181F + A237V + R480K and/or G413L/S + H416D + E418A |
| DS650 | L260P + C302R + R336L + D379V + R454P + E457N | L181F + A237V + R480K and/or G413L/S + H416D + E418A |
| DS651 | L260P + C302R + R336L + D379V + R454P | L181F + A237V + R480K and/or G413L/S + H416D + E418A |
| DS652 | L260P + C302R + R336L + D379V + R454A + E457L | L181F + A237V + R480K and/or G413L/S + H416D + E418A |
| DS653 | L260P + C302R + R336L + D379V + R454A + E457N | L181F + A237V + R480K and/or G413L/S + H416D + E418A |
| DS654 | L260P + C302R + R336L + D379V + R454A | L181F + A237V + R480K and/or G413L/S + H416D + E418A |
| DS655 | L260P + C302R + R336L + D379V + E457L | L181F + A237V + R480K and/or G413L/S + H416D + E418A |
| DS656 | L260P + C302R + R336L + D379V + E457N | L181F + A237V + R480K and/or G413L/S + H416D + E418A |
| DS657 | L260P + C302R + R336L + D379V | L181F + A237V + R480K and/or G413L/S + H416D + E418A |
| DS658 | L260P + C302R + R336L + R454P + E457L | L181F + A237V + R480K and/or G413L/S + H416D + E418A |
| DS659 | L260P + C302R + R336L + R454P + E457N | L181F + A237V + R480K and/or G413L/S + H416D + E418A |
| DS660 | L260P + C302R + R336L + R454P | L181F + A237V + R480K and/or G413L/S + H416D + E418A |
| DS661 | L260P + C302R + R336L + R454A + E457L | L181F + A237V + R480K and/or G413L/S + H416D + E418A |
| DS662 | L260P + C302R + R336L + R454A + E457N | L181F + A237V + R480K and/or G413L/S + H416D + E418A |
| DS663 | L260P + C302R + R336L + R454A | L181F + A237V + R480K and/or G413L/S + H416D + E418A |
| DS664 | L260P + C302R + R336L + E457L | L181F + A237V + R480K and/or G413L/S + H416D + E418A |
| DS665 | L260P + C302R + R336L + E457N | L181F + A237V + R480K and/or G413L/S + H416D + E418A |
| DS666 | L260P + C302R + R336L | L181F + A237V + R480K and/or G413L/S + H416D + E418A |
| DS667 | L260P + C302R + R336N + D379V + R454P + E457L | L181F + A237V + R480K and/or G413L/S + H416D + E418A |
| DS668 | L260P + C302R + R336N + D379V + R454P + E457N | L181F + A237V + R480K and/or G413L/S + H416D + E418A |
| DS669 | L260P + C302R + R336N + D379V + R454P | L181F + A237V + R480K and/or G413L/S + H416D + E418A |
| DS670 | L260P + C302R + R336N + D379V + R454A + E457L | L181F + A237V + R480K and/or G413L/S + H416D + E418A |
| DS671 | L260P + C302R + R336N + D379V + R454A + E457N | L181F + A237V + R480K and/or G413L/S + H416D + E418A |
| DS672 | L260P + C302R + R336N + D379V + R454A | L181F + A237V + R480K and/or G413L/S + H416D + E418A |
| DS673 | L260P + C302R + R336N + D379V + E457L | L181F + A237V + R480K and/or G413L/S + H416D + E418A |
| DS674 | L260P + C302R + R336N + D379V + E457N | L181F + A237V + R480K and/or G413L/S + H416D + E418A |
| DS675 | L260P + C302R + R336N + D379V | L181F + A237V + R480K and/or G413L/S + H416D + E418A |
| DS676 | L260P + C302R + R336N + R454P + E457L | L181F + A237V + R480K and/or G413L/S + H416D + E418A |
| DS677 | L260P + C302R + R336N + R454P + E457N | L181F + A237V + R480K and/or G413L/S + H416D + E418A |
| DS678 | L260P + C302R + R336N + R454P | L181F + A237V + R480K and/or G413L/S + H416D + E418A |
| DS679 | L260P + C302R + R336N + R454A + E457L | L181F + A237V + R480K and/or G413L/S + H416D + E418A |
| DS680 | L260P + C302R + R336N + R454A + E457N | L181F + A237V + R480K and/or G413L/S + H416D + E418A |
| DS681 | L260P + C302R + R336N + R454A | L181F + A237V + R480K and/or G413L/S + H416D + E418A |
| DS682 | L260P + C302R + R336N + E457L | L181F + A237V + R480K and/or G413L/S + H416D + E418A |
| DS683 | L260P + C302R + R336N + E457N | L181F + A237V + R480K and/or G413L/S + H416D + E418A |
| DS684 | L260P + C302R + R336N | L181F + A237V + R480K and/or G413L/S + H416D + E418A |
| DS685 | L260P + C302R + D379V + R454P + E457L | L181F + A237V + R480K and/or G413L/S + H416D + E418A |
| DS686 | L260P + C302R + D379V + R454P + E457N | L181F + A237V + R480K and/or G413L/S + H416D + E418A |
| DS687 | L260P + C302R + D379V + R454P | L181F + A237V + R480K and/or G413L/S + H416D + E418A |
| DS688 | L260P + C302R + D379V + R454A + E457L | L181F + A237V + R480K and/or G413L/S + H416D + E418A |
| DS689 | L260P + C302R + D379V + R454A + E457N | L181F + A237V + R480K and/or G413L/S + H416D + E418A |
| DS690 | L260P + C302R + D379V + R454A | L181F + A237V + R480K and/or G413L/S + H416D + E418A |
| DS691 | L260P + C302R + D379V + E457L | L181F + A237V + R480K and/or G413L/S + H416D + E418A |
| DS692 | L260P + C302R + D379V + E457N | L181F + A237V + R480K and/or G413L/S + H416D + E418A |
| DS693 | L260P + C302R + D379V | L181F + A237V + R480K and/or G413L/S + H416D + E418A |
| DS694 | L260P + C302R + R454P + E457L | L181F + A237V + R480K and/or G413L/S + H416D + E418A |
| DS695 | L260P + C302R + R454P + E457N | L181F + A237V + R480K and/or G413L/S + H416D + E418A |
| DS696 | L260P + C302R + R454P | L181F + A237V + R480K and/or G413L/S + H416D + E418A |
| DS697 | L260P + C302R + R454A + E457L | L181F + A237V + R480K and/or G413L/S + H416D + E418A |
| DS698 | L260P + C302R + R454A + E457N | L181F + A237V + R480K and/or G413L/S + H416D + E418A |
| DS699 | L260P + C302R + R454A | L181F + A237V + R480K and/or G413L/S + H416D + E418A |
| DS700 | L260P + C302R + E457L | L181F + A237V + R480K and/or G413L/S + H416D + E418A |
| DS701 | L260P + C302R + E457N | L181F + A237V + R480K and/or G413L/S + H416D + E418A |
| DS702 | L260P + C302R | L181F + A237V + R480K and/or G413L/S + H416D + E418A |
| DS703 | L260P + C302G + R336L + D379V + R454P + E457L | L181F + A237V + R480K and/or G413L/S + H416D + E418A |
| DS704 | L260P + C302G + R336L + D379V + R454P + E457N | L181F + A237V + R480K and/or G413L/S + H416D + E418A |
| DS705 | L260P + C302G + R336L + D379V + R454P | L181F + A237V + R480K and/or G413L/S + H416D + E418A |
| DS706 | L260P + C302G + R336L + D379V + R454A + E457L | L181F + A237V + R480K and/or G413L/S + H416D + E418A |
| DS707 | L260P + C302G + R336L + D379V + R454A + E457N | L181F + A237V + R480K and/or G413L/S + H416D + E418A |
| DS708 | L260P + C302G + R336L + D379V + R454A | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS709 | L260P + C302G + R336L + D379V + E457L | L181F + A237V + R480K and/or G413L/S + H416D + E418A |
| DS710 | L260P + C302G + R336L + D379V + E457N | L181F + A237V + R480K and/or G413L/S + H416D + E418A |
| DS711 | L260P + C302G + R336L + D379V | L181F + A237V + R480K and/or G413L/S + H416D + E418A |
| DS712 | L260P + C302G + R336L + R454P + E457L | L181F + A237V + R480K and/or G413L/S + H416D + E418A |
| DS713 | L260P + C302G + R336L + R454P + E457N | L181F + A237V + R480K and/or G413L/S + H416D + E418A |
| DS714 | L260P + C302G + R336L + R454P | L181F + A237V + R480K and/or G413L/S + H416D + E418A |
| DS715 | L260P + C302G + R336L + R454A + E457L | L181F + A237V + R480K and/or G413L/S + H416D + E418A |
| DS716 | L260P + C302G + R336L + R454A + E457N | L181F + A237V + R480K and/or G413L/S + H416D + E418A |
| DS717 | L260P + C302G + R336L + R454A | L181F + A237V + R480K and/or G413L/S + H416D + E418A |
| DS718 | L260P + C302G + R336L + E457L | L181F + A237V + R480K and/or G413L/S + H416D + E418A |
| DS719 | L260P + C302G + R336L + E457N | L181F + A237V + R480K and/or G413L/S + H416D + E418A |
| DS720 | L260P + C302G + R336L | L181F + A237V + R480K and/or G413L/S + H416D + E418A |
| DS721 | L260P + C302G + R336N + D379V + R454P + E457L | L181F + A237V + R480K and/or G413L/S + H416D + E418A |
| DS722 | L260P + C302G + R336N + D379V + R454P + E457N | L181F + A237V + R480K and/or G413L/S + H416D + E418A |
| DS723 | L260P + C302G + R336N + D379V + R454P | L181F + A237V + R480K and/or G413L/S + H416D + E418A |
| DS724 | L260P + C302G + R336N + D379V + R454A + E457L | L181F + A237V + R480K and/or G413L/S + H416D + E418A |
| DS725 | L260P + C302G + R336N + D379V + R454A + E457N | L181F + A237V + R480K and/or G413L/S + H416D + E418A |
| DS726 | L260P + C302G + R336N + D379V + R454A | L181F + A237V + R480K and/or G413L/S + H416D + E418A |
| DS727 | L260P + C302G + R336N + D379V + E457L | L181F + A237V + R480K and/or G413L/S + H416D + E418A |
| DS728 | L260P + C302G + R336N + D379V + E457N | L181F + A237V + R480K and/or G413L/S + H416D + E418A |
| DS729 | L260P + C302G + R336N + D379V | L181F + A237V + R480K and/or G413L/S + H416D + E418A |
| DS730 | L260P + C302G + R336N + R454P + E457L | L181F + A237V + R480K and/or G413L/S + H416D + E418A |
| DS731 | L260P + C302G + R336N + R454P + E457N | L181F + A237V + R480K and/or G413L/S + H416D + E418A |
| DS732 | L260P + C302G + R336N + R454P | L181F + A237V + R480K and/or G413L/S + H416D + E418A |
| DS733 | L260P + C302G + R336N + R454A + E457L | L181F + A237V + R480K and/or G413L/S + H416D + E418A |
| DS734 | L260P + C302G + R336N + R454A + E457N | L181F + A237V + R480K and/or G413L/S + H416D + E418A |
| DS735 | L260P + C302G + R336N + R454A | L181F + A237V + R480K and/or G413L/S + H416D + E418A |
| DS736 | L260P + C302G + R336N + E457L | L181F + A237V + R480K and/or G413L/S + H416D + E418A |
| DS737 | L260P + C302G + R336N + E457N | L181F + A237V + R480K and/or G413L/S + H416D + E418A |
| DS738 | L260P + C302G + R336N | L181F + A237V + R480K and/or G413L/S + H416D + E418A |
| DS739 | L260P + C302G + D379V + R454P + E457L | L181F + A237V + R480K and/or G413L/S + H416D + E418A |
| DS740 | L260P + C302G + D379V + R454P + E457N | L181F + A237V + R480K and/or G413L/S + H416D + E418A |
| DS741 | L260P + C302G + D379V + R454P | L181F + A237V + R480K and/or G413L/S + H416D + E418A |
| DS742 | L260P + C302G + D379V + R454A + E457L | L181F + A237V + R480K and/or G413L/S + H416D + E418A |
| DS743 | L260P + C302G + D379V + R454A + E457N | L181F + A237V + R480K and/or G413L/S + H416D + E418A |
| DS744 | L260P + C302G + D379V + R454A | L181F + A237V + R480K and/or G413L/S + H416D + E418A |
| DS745 | L260P + C302G + D379V + E457L | L181F + A237V + R480K and/or G413L/S + H416D + E418A |
| DS746 | L260P + C302G + D379V + E457N | L181F + A237V + R480K and/or G413L/S + H416D + E418A |
| DS747 | L260P + C302G + D379V | L181F + A237V + R480K and/or G413L/S + H416D + E418A |
| DS748 | L260P + C302G + R454P + E457L | L181F + A237V + R480K and/or G413L/S + H416D + E418A |
| DS749 | L260P + C302G + R454P + E457N | L181F + A237V + R480K and/or G413L/S + H416D + E418A |
| DS750 | L260P + C302G + R454P | L181F + A237V + R480K and/or G413L/S + H416D + E418A |
| DS751 | L260P + C302G + R454A + E457L | L181F + A237V + R480K and/or G413L/S + H416D + E418A |
| DS752 | L260P + C302G + R454A + E457N | L181F + A237V + R480K and/or G413L/S + H416D + E418A |
| DS753 | L260P + C302G + R454A | L181F + A237V + R480K and/or G413L/S + H416D + E418A |
| DS754 | L260P + C302G + E457L | L181F + A237V + R480K and/or G413L/S + H416D + E418A |
| DS755 | L260P + C302G + E457N | L181F + A237V + R480K and/or G413L/S + H416D + E418A |
| DS756 | L260P + C302G | L181F + A237V + R480K and/or G413L/S + H416D + E418A |
| DS811 | C302R + R336L + D379V + R454P + E457L | L181F + A237V + R480K and/or G413L/S + H416D + E418A |
| DS812 | C302R + R336L + D379V + R454P + E457N | L181F + A237V + R480K and/or G413L/S + H416D + E418A |
| DS813 | C302R + R336L + D379V + R454P | L181F + A237V + R480K and/or G413L/S + H416D + E418A |
| DS814 | C302R + R336L + D379V + R454A + E457L | L181F + A237V + R480K and/or G413L/S + H416D + E418A |
| DS815 | C302R + R336L + D379V + R454A + E457N | L181F + A237V + R480K and/or G413L/S + H416D + E418A |
| DS816 | C302R + R336L + D379V + R454A | L181F + A237V + R480K and/or G413L/S + H416D + E418A |
| DS817 | C302R + R336L + D379V + E457L | L181F + A237V + R480K and/or G413L/S + H416D + E418A |
| DS818 | C302R + R336L + D379V + E457N | L181F + A237V + R480K and/or G413L/S + H416D + E418A |
| DS819 | C302R + R336L + D379V | L181F + A237V + R480K and/or G413L/S + H416D + E418A |
| DS820 | C302R + R336L + R454P + E457L | L181F + A237V + R480K and/or G413L/S + H416D + E418A |
| DS821 | C302R + R336L + R454P + E457N | L181F + A237V + R480K and/or G413L/S + H416D + E418A |
| DS822 | C302R + R336L + R454P | L181F + A237V + R480K and/or G413L/S + H416D + E418A |
| DS823 | C302R + R336L + R454A + E457L | L181F + A237V + R480K and/or G413L/S + H416D + E418A |
| DS824 | C302R + R336L + R454A + E457N | L181F + A237V + R480K and/or G413L/S + H416D + E418A |
| DS825 | C302R + R336L + R454A | L181F + A237V + R480K and/or G413L/S + H416D + E418A |
| DS826 | C302R + R336L + E457L | L181F + A237V + R480K and/or G413L/S + H416D + E418A |
| DS827 | C302R + R336L + E457N | L181F + A237V + R480K and/or G413L/S + H416D + E418A |
| DS828 | C302R + R336L | L181F + A237V + R480K and/or G413L/S + H416D + E418A |
| DS829 | C302R + R336N + D379V + R454P + E457L | L181F + A237V + R480K and/or G413L/S + H416D + E418A |
| DS830 | C302R + R336N + D379V + R454P + E457N | L181F + A237V + R480K and/or G413L/S + H416D + E418A |
| DS831 | C302R + R336N + D379V + R454P | L181F + A237V + R480K and/or G413L/S + H416D + E418A |
| DS832 | C302R + R336N + D379V + R454A + E457L | L181F + A237V + R480K and/or G413L/S + H416D + E418A |
| DS833 | C302R + R336N + D379V + R454A + E457N | L181F + A237V + R480K and/or G413L/S + H416D + E418A |
| DS834 | C302R + R336N + D379V + R454A | L181F + A237V + R480K and/or G413L/S + H416D + E418A |
| DS835 | C302R + R336N + D379V + E457L | L181F + A237V + R480K and/or G413L/S + H416D + E418A |
| DS836 | C302R + R336N + D379V + E457N | L181F + A237V + R480K and/or G413L/S + H416D + E418A |
| DS837 | C302R + R336N + D379V | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS838 | C302R + R336N + R454P + E457L | L181F + A237V + R480K and/or G413L/S + H416D + E418A |
| DS839 | C302R + R336N + R454P + E457N | L181F + A237V + R480K and/or G413L/S + H416D + E418A |
| DS840 | C302R + R336N + R454P | L181F + A237V + R480K and/or G413L/S + H416D + E418A |
| DS841 | C302R + R336N + R454A + E457L | L181F + A237V + R480K and/or G413L/S + H416D + E418A |
| DS842 | C302R + R336N + R454A + E457N | L181F + A237V + R480K and/or G413L/S + H416D + E418A |
| DS843 | C302R + R336N + R454A | L181F + A237V + R480K and/or G413L/S + H416D + E418A |
| DS844 | C302R + R336N + E457L | L181F + A237V + R480K and/or G413L/S + H416D + E418A |
| DS845 | C302R + R336N + E457N | L181F + A237V + R480K and/or G413L/S + H416D + E418A |
| DS846 | C302R + R336N | L181F + A237V + R480K and/or G413L/S + H416D + E418A |
| DS847 | C302R + D379V + R454P + E457L | L181F + A237V + R480K and/or G413L/S + H416D + E418A |
| DS848 | C302R + D379V + R454P + E457N | L181F + A237V + R480K and/or G413L/S + H416D + E418A |
| DS849 | C302R + D379V + R454P | L181F + A237V + R480K and/or G413L/S + H416D + E418A |
| DS850 | C302R + D379V + R454A + E457L | L181F + A237V + R480K and/or G413L/S + H416D + E418A |
| DS851 | C302R + D379V + R454A + E457N | L181F + A237V + R480K and/or G413L/S + H416D + E418A |
| DS852 | C302R + D379V + R454A | L181F + A237V + R480K and/or G413L/S + H416D + E418A |
| DS853 | C302R + D379V + E457L | L181F + A237V + R480K and/or G413L/S + H416D + E418A |
| DS854 | C302R + D379V + E457N | L181F + A237V + R480K and/or G413L/S + H416D + E418A |
| DS855 | C302R + D379V | L181F + A237V + R480K and/or G413L/S + H416D + E418A |
| DS856 | C302R + R454P + E457L | L181F + A237V + R480K and/or G413L/S + H416D + E418A |
| DS857 | C302R + R454P + E457N | L181F + A237V + R480K and/or G413L/S + H416D + E418A |
| DS858 | C302R + R454P | L181F + A237V + R480K and/or G413L/S + H416D + E418A |
| DS859 | C302R + R454A + E457L | L181F + A237V + R480K and/or G413L/S + H416D + E418A |
| DS860 | C302R + R454A + E457N | L181F + A237V + R480K and/or G413L/S + H416D + E418A |
| DS861 | C302R + R454A | L181F + A237V + R480K and/or G413L/S + H416D + E418A |
| DS862 | C302R + E457L | L181F + A237V + R480K and/or G413L/S + H416D + E418A |
| DS863 | C302R + E457N | L181F + A237V + R480K and/or G413L/S + H416D + E418A |
| DS864 | C302R | L181F + A237V + R480K and/or G413L/S + H416D + E418A |
| DS865 | C302G + R336L + D379V + R454P + E457L | L181F + A237V + R480K and/or G413L/S + H416D + E418A |
| DS866 | C302G + R336L + D379V + R454P + E457N | L181F + A237V + R480K and/or G413L/S + H416D + E418A |
| DS867 | C302G + R336L + D379V + R454P | L181F + A237V + R480K and/or G413L/S + H416D + E418A |
| DS868 | C302G + R336L + D379V + R454A + E457L | L181F + A237V + R480K and/or G413L/S + H416D + E418A |
| DS869 | C302G + R336L + D379V + R454A + E457N | L181F + A237V + R480K and/or G413L/S + H416D + E418A |
| DS870 | C302G + R336L + D379V + R454A | L181F + A237V + R480K and/or G413L/S + H416D + E418A |
| DS871 | C302G + R336L + D379V + E457L | L181F + A237V + R480K and/or G413L/S + H416D + E418A |
| DS872 | C302G + R336L + D379V + E457N | L181F + A237V + R480K and/or G413L/S + H416D + E418A |
| DS873 | C302G + R336L + D379V | L181F + A237V + R480K and/or G413L/S + H416D + E418A |
| DS874 | C302G + R336L + R454P + E457L | L181F + A237V + R480K and/or G413L/S + H416D + E418A |
| DS875 | C302G + R336L + R454P + E457N | L181F + A237V + R480K and/or G413L/S + H416D + E418A |
| DS876 | C302G + R336L + R454P | L181F + A237V + R480K and/or G413L/S + H416D + E418A |
| DS877 | C302G + R336L + R454A + E457L | L181F + A237V + R480K and/or G413L/S + H416D + E418A |
| DS878 | C302G + R336L + R454A + E457N | L181F + A237V + R480K and/or G413L/S + H416D + E418A |
| DS879 | C302G + R336L + R454A | L181F + A237V + R480K and/or G413L/S + H416D + E418A |
| DS880 | C302G + R336L + E457L | L181F + A237V + R480K and/or G413L/S + H416D + E418A |
| DS881 | C302G + R336L + E457N | L181F + A237V + R480K and/or G413L/S + H416D + E418A |
| DS882 | C302G + R336L | L181F + A237V + R480K and/or G413L/S + H416D + E418A |
| DS883 | C302G + R336N + D379V + R454P + E457L | L181F + A237V + R480K and/or G413L/S + H416D + E418A |
| DS884 | C302G + R336N + D379V + R454P + E457N | L181F + A237V + R480K and/or G413L/S + H416D + E418A |
| DS885 | C302G + R336N + D379V + R454P | L181F + A237V + R480K and/or G413L/S + H416D + E418A |
| DS886 | C302G + R336N + D379V + R454A + E457L | L181F + A237V + R480K and/or G413L/S + H416D + E418A |
| DS887 | C302G + R336N + D379V + R454A + E457N | L181F + A237V + R480K and/or G413L/S + H416D + E418A |
| DS888 | C302G + R336N + D379V + R454A | L181F + A237V + R480K and/or G413L/S + H416D + E418A |
| DS889 | C302G + R336N + D379V + E457L | L181F + A237V + R480K and/or G413L/S + H416D + E418A |
| DS890 | C302G + R336N + D379V + E457N | L181F + A237V + R480K and/or G413L/S + H416D + E418A |
| DS891 | C302G + R336N + D379V | L181F + A237V + R480K and/or G413L/S + H416D + E418A |
| DS892 | C302G + R336N + R454P + E457L | L181F + A237V + R480K and/or G413L/S + H416D + E418A |
| DS893 | C302G + R336N + R454P + E457N | L181F + A237V + R480K and/or G413L/S + H416D + E418A |
| DS894 | C302G + R336N + R454P | L181F + A237V + R480K and/or G413L/S + H416D + E418A |
| DS895 | C302G + R336N + R454A + E457L | L181F + A237V + R480K and/or G413L/S + H416D + E418A |
| DS896 | C302G + R336N + R454A + E457N | L181F + A237V + R480K and/or G413L/S + H416D + E418A |
| DS897 | C302G + R336N + R454A | L181F + A237V + R480K and/or G413L/S + H416D + E418A |
| DS898 | C302G + R336N + E457L | L181F + A237V + R480K and/or G413L/S + H416D + E418A |
| DS899 | C302G + R336N + E457N | L181F + A237V + R480K and/or G413L/S + H416D + E418A |
| DS900 | C302G + R336N | L181F + A237V + R480K and/or G413L/S + H416D + E418A |
| DS901 | C302G + D379V + R454P + E457L | L181F + A237V + R480K and/or G413L/S + H416D + E418A |
| DS902 | C302G + D379V + R454P + E457N | L181F + A237V + R480K and/or G413L/S + H416D + E418A |
| DS903 | C302G + D379V + R454P | L181F + A237V + R480K and/or G413L/S + H416D + E418A |
| DS904 | C302G + D379V + R454A + E457L | L181F + A237V + R480K and/or G413L/S + H416D + E418A |
| DS905 | C302G + D379V + R454A + E457N | L181F + A237V + R480K and/or G413L/S + H416D + E418A |
| DS906 | C302G + D379V + R454A | L181F + A237V + R480K and/or G413L/S + H416D + E418A |
| DS907 | C302G + D379V + E457L | L181F + A237V + R480K and/or G413L/S + H416D + E418A |
| DS908 | C302G + D379V + E457N | L181F + A237V + R480K and/or G413L/S + H416D + E418A |
| DS909 | C302G + D379V | L181F + A237V + R480K and/or G413L/S + H416D + E418A |
| DS910 | C302G + R454P + E457L | L181F + A237V + R480K and/or G413L/S + H416D + E418A |
| DS911 | C302G + R454P + E457N | L181F + A237V + R480K and/or G413L/S + H416D + E418A |
| DS912 | C302G + R454P | L181F + A237V + R480K and/or G413L/S + H416D + E418A |

TABLE 1-continued

Variants of TdT having the amino acid sequence of SEQ ID N° 2 with at least a substitution on residue C302

| Name | Variable Mutations | Optional Constant Mutations |
|---|---|---|
| DS913 | C302G + R454A + E457L | L181F + A237V + R480K and/or G413L/S + H416D + E418A |
| DS914 | C302G + R454A + E457N | L181F + A237V + R480K and/or G413L/S + H416D + E418A |
| DS915 | C302G + R454A | L181F + A237V + R480K and/or G413L/S + H416D + E418A |
| DS916 | C302G + E457L | L181F + A237V + R480K and/or G413L/S + H416D + E418A |
| DS917 | C302G + E457N | L181F + A237V + R480K and/or G413L/S + H416D + E418A |
| DS918 | C302G | L181F + A237V + R480K and/or G413L/S + H416D + E418A |

In a particular embodiment, the variants of the invention comprise the amino acid sequence of SEQ ID N° 2 (or functionally equivalent sequence) and optionally additional amino acid fragments at the C-ter or N-ter. In another embodiment, the variants of the invention comprise the amino acid sequence of SEQ ID N° 1 (or functionally equivalent sequence) and optionally additional amino acid fragments at the C-ter or N-ter. In another embodiment, the variants of the invention consist solely on the amino acid sequence of SEQ ID N° 2 (or functionally equivalent sequence). More particularly, in a particular embodiment, the variants of the invention are deprived of the BRTC-like domain, which corresponds to residues 1 to 129 of SEQ ID N° 1.

According to a second aspect of the invention, the variant of Terminal deoxynucleotidyl Transferase (TdT) (i) comprises the amino acid sequence as set forth in SEQ ID N° 2 or a functionally equivalent sequence, with at least three amino acid substitutions selected from M192R/Q, L260P, C302G/R, R336L/N, D379V, R454P/N and E457N/L/T/S, or a functionally equivalent residue, wherein the positions are numbered by reference to the amino acid sequence set forth in SEQ ID N° 1, (ii) is able to synthesize a nucleic acid fragment without template and (iii) is able to incorporate a modified nucleotide into the nucleic fragment.

For instance, the variant of TdT comprises the combination of substitution selected from M192R+L260P+R336L, M192R+L260P+R336N, M192R+L260P+D379V, M192R+L260P+R454P, M192R+L260P+R454A, M192R+L260P+E457L, M192R+L260P+E457N, M192R+R336L+D379V, M192R+R336L+R454P, M192R+R336L+R454A, M192R+R336L+E457L, M192R+R336L+E457N, M192R+R336N+D379V, M192R+R336N+R454P, M192R+R336N+R454A, M192R+R336N+E457L, M192R+R336N+E457N, M192R+D379V+R454P, M192R+D379V+R454A, M192R+R454P+E457L, M192R+R454P+E457N, M192R+R454A+E457L, M192R+R454A+E457N, M192Q+L260P+R336L, M192Q+L260P+R336N, M192Q+L260P+D379V, M192Q+L260P+R454P, M192Q+L260P+R454A, M192Q+L260P+E457L, M192Q+L260P+E457N, M192Q+R336L+D379V, M192Q+R336L+R454P, M192Q+R336L+R454A, M192Q+R336L+E457L, M192Q+R336L+E457N, M192Q+D379V+R454P, M192Q+D379V+R454A, M192Q+D379V+E457L, M192Q+D379V+E457N, M192Q+R454P+E457L, M192Q+R454P+E457N, M192Q+R454A+E457L, M192Q+R454A+E457N, L260P+R336L+D379V, L260P+R336L+R454A, L260P+R336L+E457L, L260P+R336L+E457N, L260P+R336N+D379V, L260P+R336N+R454P, L260P+R336N+R454A, L260P+R336N+E457L, L260P+R336N+E457N, L260P+D379V+R454P, L260P+D379V+R454A, L260P+D379V+E457L, L260P+D379V+E457N, L260P+R454P+E457L, L260P+R454P+E457N, L260P+R454A+E457L, L260P+R454A+E457N, R336L+D379V+R454P, R336L+D379V+R454A, R336L+D379V+E457L, R336L+D379V+E457N, R336L+R454P+E457L, R336L+R454P+E457N, R336L+R454A+E457L, R336L+R454A+E457N, R336N+D379V+R454P, R336N+D379V+R454A, R336N+D379V+E457L, R336N+D379V+E457N, R336N+R454P+E457L, R336N+R454P+E457N, R336N+R454A+E457L, R336N+R454A+E457N, D379V+R454P+E457L, D379V+R454P+E457N, D379V+R454A+E457L, D379V+R454A+E457N and R336L+D379V+R454P, or functionally equivalent residue(s).

In a particular embodiment, the variant of TdT comprises the amino acid sequence of SEQ ID N° 2, or functionally equivalent sequence, with the combination of substitutions R336L+R454P+E457L (DS928), or functionally equivalent residues.

In a particular embodiment, the variant of TdT comprises the amino acid sequence of SEQ ID N° 2, or functionally equivalent sequence, with the combination of substitutions R336N+R454A+E457N (DS950), or functionally equivalent residues.

Such variant may further comprise at least one substitution at position corresponding to residues selected from L181, A237, L260, T340, G413, H416, E418, W450, R480 and A510, or functionally equivalent residue(s).

As exposed above, said variant may also comprise the combination of constant mutations L181F+A237V+R480K and/or G413L/S+H416D+E418A, or functionally equivalent residue(s).

According to a further aspect, the invention provides a variant of Terminal deoxynucleotidyl Transferase (TdT) which (i) comprises the amino acid sequence as set forth in SEQ ID N° 2 or a functionally equivalent sequence, with at least one amino acid substitution selected from M192R, M192Q, L260P, R336L, R336N, D379V, R454P, R454A, E457L, E457N, or functionally equivalent residue(s), wherein the positions are numbered by reference to the amino acid sequence set forth in SEQ ID N° 1, (ii) is able to synthesize a nucleic acid fragment without template and (iii) is able to incorporate a modified nucleotide into the nucleic fragment.

In another aspect, the invention provides a variant of Terminal deoxynucleotidyl Transferase (TdT) which (i) comprises the amino acid sequence as set forth in SEQ ID N° 2 or a functionally equivalent sequence, with at least the combination of substitutions selected from M192R+L260P, M192R+R336L, M192R+R336N, M192R+D379V, M192R+R454P, M192R+R454A, M192R+E457L, M192R+E457N, M192Q+L260P, M192Q+R336L, M192Q+R336N, M192Q+D379V, M192Q+R454P, M192Q+R454A, M192Q+E457L, M192Q+E457N, L260P+R336L, L260P+R336N, L260P+D379V, L260P+R454P, L260P+R454A, L260P+E457L, L260P+E457N, R336L+D379V, R336L+R454P, R336L+R454A, R336L+E457L, R336L+E457N, R336N+D379V, R336N+R454P, R336N+R454A, R336N+E457L, R336N+E457N, D379V+R454P, D379V+R454A, D379V+E457L, D379V+E457N, R454P+E457L, R454P+E457N, R454A+E457L and R454A+E457N, or functionally equivalent residue(s), wherein the positions are numbered by reference to the amino acid sequence set forth in SEQ ID N° 1, (ii) is able to synthesize a nucleic acid fragment without template and (iii) is able to incorporate a modified nucleotide into the nucleic fragment.

It is thus an object of the invention to provide a TdT variant having the amino acid sequence as set forth in SEQ ID N° 2, or functionally equivalent sequence, with any substitution or combination of substitutions listed in table 2, listed as "Variable Mutations", or functionally equivalent residue(s) and optionally one or both combinations of constant mutations L181F+A237V+R480K an G413L/S+H416D+E418A, or functionally equivalent residue(s).

According to a particular embodiment, the variant comprises at least one substitution or combination of substitutions as listed in table 2, and optionally one or more additional mutation(s).

TABLE 2

Variants of TdT having the amino acid sequence of SEQ ID N° 2

| Name | Variable Mutations | Optional Constant Mutations |
|---|---|---|
| DS109 | M192R + L260P + R336L + D379V + R454P + E457L | L181F + A237V + R480K and/or G413L/S + H416D + E418A |
| DS110 | M192R + L260P + R336L + D379V + R454P + E457N | L181F + A237V + R480K and/or G413L/S + H416D + E418A |
| DS111 | M192R + L260P + R336L + D379V + R454P | L181F + A237V + R480K and/or G413L/S + H416D + E418A |
| DS112 | M192R + L260P + R336L + D379V + R454A + E457L | L181F + A237V + R480K and/or G413L/S + H416D + E418A |
| DS113 | M192R + L260P + R336L + D379V + R454A + E457N | L181F + A237V + R480K and/or G413L/S + H416D + E418A |
| DS114 | M192R + L260P + R336L + D379V + R454A | L181F + A237V + R480K and/or G413L/S + H416D + E418A |
| DS115 | M192R + L260P + R336L + D379V + E457L | L181F + A237V + R480K and/or G413L/S + H416D + E418A |
| DS116 | M192R + L260P + R336L + D379V + E457N | L181F + A237V + R480K and/or G413L/S + H416D + E418A |
| DS117 | M192R + L260P + R336L + D379V | L181F + A237V + R480K and/or G413L/S + H416D + E418A |
| DS118 | M192R + L260P + R336L + R454P + E457L | L181F + A237V + R480K and/or G413L/S + H416D + E418A |
| DS119 | M192R + L260P + R336L + R454P + E457N | L181F + A237V + R480K and/or G413L/S + H416D + E418A |
| DS120 | M192R + L260P + R336L + R454P | L181F + A237V + R480K and/or G413L/S + H416D + E418A |
| DS121 | M192R + L260P + R336L + R454A + E457L | L181F + A237V + R480K and/or G413L/S + H416D + E418A |
| DS122 | M192R + L260P + R336L + R454A + E457N | L181F + A237V + R480K and/or G413L/S + H416D + E418A |
| DS123 | M192R + L260P + R336L + R454A | L181F + A237V + R480K and/or G413L/S + H416D + E418A |
| DS124 | M192R + L260P + R336L + E457L | L181F + A237V + R480K and/or G413L/S + H416D + E418A |
| DS125 | M192R + L260P + R336L + E457N | L181F + A237V + R480K and/or G413L/S + H416D + E418A |
| DS126 | M192R + L260P + R336L | L181F + A237V + R480K and/or G413L/S + H416D + E418A |
| DS127 | M192R + L260P + R336N + D379V + R454P + E457L | L181F + A237V + R480K and/or G413L/S + H416D + E418A |
| DS128 | M192R + L260P + R336N + D379V + R454P + E457N | L181F + A237V + R480K and/or G413L/S + H416D + E418A |
| DS129 | M192R + L260P + R336N + D379V + R454P | L181F + A237V + R480K and/or G413L/S + H416D + E418A |
| DS130 | M192R + L260P + R336N + D379V + R454A + E457L | L181F + A237V + R480K and/or G413L/S + H416D + E418A |
| DS131 | M192R + L260P + R336N + D379V + R454A + E457N | L181F + A237V + R480K and/or G413L/S + H416D + E418A |
| DS132 | M192R + L260P + R336N + D379V + R454A | L181F + A237V + R480K and/or G413L/S + H416D + E418A |
| DS133 | M192R + L260P + R336N + D379V + E457L | L181F + A237V + R480K and/or G413L/S + H416D + E418A |
| DS134 | M192R + L260P + R336N + D379V + E457N | L181F + A237V + R480K and/or G413L/S + H416D + E418A |
| DS135 | M192R + L260P + R336N + D379V | L181F + A237V + R480K and/or G413L/S + H416D + E418A |
| DS136 | M192R + L260P + R336N + R454P + E457L | L181F + A237V + R480K and/or G413L/S + H416D + E418A |
| DS137 | M192R + L260P + R336N + R454P + E457N | L181F + A237V + R480K and/or G413L/S + H416D + E418A |
| DS138 | M192R + L260P + R336N + R454P | L181F + A237V + R480K and/or G413L/S + H416D + E418A |
| DS139 | M192R + L260P + R336N + R454A + E457L | L181F + A237V + R480K and/or G413L/S + H416D + E418A |
| DS140 | M192R + L260P + R336N + R454A + E457N | L181F + A237V + R480K and/or G413L/S + H416D + E418A |
| DS141 | M192R + L260P + R336N + R454A | L181F + A237V + R480K and/or G413L/S + H416D + E418A |
| DS142 | M192R + L260P + R336N + E457L | L181F + A237V + R480K and/or G413L/S + H416D + E418A |
| DS143 | M192R + L260P + R336N + E457N | L181F + A237V + R480K and/or G413L/S + H416D + E418A |
| DS144 | M192R + L260P + R336N | L181F + A237V + R480K and/or G413L/S + H416D + E418A |
| DS145 | M192R + L260P + D379V + R454P + E457L | L181F + A237V + R480K and/or G413L/S + H416D + E418A |
| DS146 | M192R + L260P + D379V + R454P + E457N | L181F + A237V + R480K and/or G413L/S + H416D + E418A |
| DS147 | M192R + L260P + D379V + R454P | L181F + A237V + R480K and/or G413L/S + H416D + E418A |
| DS148 | M192R + L260P + D379V + R454A + E457L | L181F + A237V + R480K and/or G413L/S + H416D + E418A |
| DS149 | M192R + L260P + D379V + R454A + E457N | L181F + A237V + R480K and/or G413L/S + H416D + E418A |
| DS150 | M192R + L260P + D379V + R454A | L181F + A237V + R480K and/or G413L/S + H416D + E418A |
| DS151 | M192R + L260P + D379V + E457L | L181F + A237V + R480K and/or G413L/S + H416D + E418A |
| DS152 | M192R + L260P + D379V + E457N | L181F + A237V + R480K and/or G413L/S + H416D + E418A |
| DS153 | M192R + L260P + D379V | L181F + A237V + R480K and/or G413L/S + H416D + E418A |
| DS154 | M192R + L260P + R454P + E457L | L181F + A237V + R480K and/or G413L/S + H416D + E418A |
| DS155 | M192R + L260P + R454P + E457N | L181F + A237V + R480K and/or G413L/S + H416D + E418A |
| DS156 | M192R + L260P + R454P | L181F + A237V + R480K and/or G413L/S + H416D + E418A |
| DS157 | M192R + L260P + R454A + E457L | L181F + A237V + R480K and/or G413L/S + H416D + E418A |
| DS158 | M192R + L260P + R454A + E457N | L181F + A237V + R480K and/or G413L/S + H416D + E418A |
| DS159 | M192R + L260P + R454A | L181F + A237V + R480K and/or G413L/S + H416D + E418A |
| DS160 | M192R + L260P + E457L | L181F + A237V + R480K and/or G413L/S + H416D + E418A |
| DS161 | M192R + L260P + E457N | L181F + A237V + R480K and/or G413L/S + H416D + E418A |
| DS162 | M192R + L260P | L181F + A237V + R480K and/or G413L/S + H416D + E418A |
| DS271 | M192R + R336L + D379V + R454P + E457L | L181F + A237V + R480K and/or G413L/S + H416D + E418A |
| DS272 | M192R + R336L + D379V + R454P + E457N | L181F + A237V + R480K and/or G413L/S + H416D + E418A |
| DS273 | M192R + R336L + D379V + R454P | L181F + A237V + R480K and/or G413L/S + H416D + E418A |
| DS274 | M192R + R336L + D379V + R454A + E457L | L181F + A237V + R480K and/or G413L/S + H416D + E418A |
| DS275 | M192R + R336L + D379V + R454A + E457N | L181F + A237V + R480K and/or G413L/S + H416D + E418A |
| DS276 | M192R + R336L + D379V + R454A | L181F + A237V + R480K and/or G413L/S + H416D + E418A |

TABLE 2-continued

Variants of TdT having the amino acid sequence of SEQ ID N° 2

| Name | Variable Mutations | Optional Constant Mutations |
|---|---|---|
| DS277 | M192R + R336L + D379V + E457L | L181F + A237V + R480K and/or G413L/S + H416D + E418A |
| DS278 | M192R + R336L + D379V + E457N | L181F + A237V + R480K and/or G413L/S + H416D + E418A |
| DS279 | M192R + R336L + D379V | L181F + A237V + R480K and/or G413L/S + H416D + E418A |
| DS280 | M192R + R336L + R454P + E457L | L181F + A237V + R480K and/or G413L/S + H416D + E418A |
| DS281 | M192R + R336L + R454P + E457N | L181F + A237V + R480K and/or G413L/S + H416D + E418A |
| DS282 | M192R + R336L + R454P | L181F + A237V + R480K and/or G413L/S + H416D + E418A |
| DS283 | M192R + R336L + R454A + E457L | L181F + A237V + R480K and/or G413L/S + H416D + E418A |
| DS284 | M192R + R336L + R454A + E457N | L181F + A237V + R480K and/or G413L/S + H416D + E418A |
| DS285 | M192R + R336L + R454A | L181F + A237V + R480K and/or G413L/S + H416D + E418A |
| DS286 | M192R + R336L + E457L | L181F + A237V + R480K and/or G413L/S + H416D + E418A |
| DS287 | M192R + R336L + E457N | L181F + A237V + R480K and/or G413L/S + H416D + E418A |
| DS288 | M192R + R336L | L181F + A237V + R480K and/or G413L/S + H416D + E418A |
| DS289 | M192R + R336N + D379V + R454P + E457L | L181F + A237V + R480K and/or G413L/S + H416D + E418A |
| DS290 | M192R + R336N + D379V + R454P + E457N | L181F + A237V + R480K and/or G413L/S + H416D + E418A |
| DS291 | M192R + R336N + D379V + R454P | L181F + A237V + R480K and/or G413L/S + H416D + E418A |
| DS292 | M192R + R336N + D379V + R454A + E457L | L181F + A237V + R480K and/or G413L/S + H416D + E418A |
| DS293 | M192R + R336N + D379V + R454A + E457N | L181F + A237V + R480K and/or G413L/S + H416D + E418A |
| DS294 | M192R + R336N + D379V + R454A | L181F + A237V + R480K and/or G413L/S + H416D + E418A |
| DS295 | M192R + R336N + D379V + E457L | L181F + A237V + R480K and/or G413L/S + H416D + E418A |
| DS296 | M192R + R336N + D379V + E457N | L181F + A237V + R480K and/or G413L/S + H416D + E418A |
| DS297 | M192R + R336N + D379V | L181F + A237V + R480K and/or G413L/S + H416D + E418A |
| DS298 | M192R + R336N + R454P + E457L | L181F + A237V + R480K and/or G413L/S + H416D + E418A |
| DS299 | M192R + R336N + R454P + E457N | L181F + A237V + R480K and/or G413L/S + H416D + E418A |
| DS300 | M192R + R336N + R454P | L181F + A237V + R480K and/or G413L/S + H416D + E418A |
| DS301 | M192R + R336N + R454A + E457L | L181F + A237V + R480K and/or G413L/S + H416D + E418A |
| DS302 | M192R + R336N + R454A + E457N | L181F + A237V + R480K and/or G413L/S + H416D + E418A |
| DS303 | M192R + R336N + R454A | L181F + A237V + R480K and/or G413L/S + H416D + E418A |
| DS304 | M192R + R336N + E457L | L181F + A237V + R480K and/or G413L/S + H416D + E418A |
| DS305 | M192R + R336N + E457N | L181F + A237V + R480K and/or G413L/S + H416D + E418A |
| DS306 | M192R + R336N | L181F + A237V + R480K and/or G413L/S + H416D + E418A |
| DS307 | M192R + D379V + R454P + E457L | L181F + A237V + R480K and/or G413L/S + H416D + E418A |
| DS308 | M192R + D379V + R454P + E457N | L181F + A237V + R480K and/or G413L/S + H416D + E418A |
| DS309 | M192R + D379V + R454P | L181F + A237V + R480K and/or G413L/S + H416D + E418A |
| DS310 | M192R + D379V + R454A + E457L | L181F + A237V + R480K and/or G413L/S + H416D + E418A |
| DS311 | M192R + D379V + R454A + E457N | L181F + A237V + R480K and/or G413L/S + H416D + E418A |
| DS312 | M192R + D379V + R454A | L181F + A237V + R480K and/or G413L/S + H416D + E418A |
| DS313 | M192R + D379V + E457L | L181F + A237V + R480K and/or G413L/S + H416D + E418A |
| DS314 | M192R + D379V + E457N | L181F + A237V + R480K and/or G413L/S + H416D + E418A |
| DS315 | M192R + D379V | L181F + A237V + R480K and/or G413L/S + H416D + E418A |
| DS316 | M192R + R454P + E457L | L181F + A237V + R480K and/or G413L/S + H416D + E418A |
| DS317 | M192R + R454P + E457N | L181F + A237V + R480K and/or G413L/S + H416D + E418A |
| DS318 | M192R + R454P | L181F + A237V + R480K and/or G413L/S + H416D + E418A |
| DS319 | M192R + R454A + E457L | L181F + A237V + R480K and/or G413L/S + H416D + E418A |
| DS320 | M192R + R454A + E457N | L181F + A237V + R480K and/or G413L/S + H416D + E418A |
| DS321 | M192R + R454A | L181F + A237V + R480K and/or G413L/S + H416D + E418A |
| DS322 | M192R + E457L | L181F + A237V + R480K and/or G413L/S + H416D + E418A |
| DS323 | M192R + E457N | L181F + A237V + R480K and/or G413L/S + H416D + E418A |
| DS324 | M192R | L181F + A237V + R480K and/or G413L/S + H416D + E418A |
| DS433 | M192Q + L260P + R336L + D379V + R454P + E457L | L181F + A237V + R480K and/or G413L/S + H416D + E418A |
| DS434 | M192Q + L260P + R336L + D379V + R454P + E457N | L181F + A237V + R480K and/or G413L/S + H416D + E418A |
| DS435 | M192Q + L260P + R336L + D379V + R454P | L181F + A237V + R480K and/or G413L/S + H416D + E418A |
| DS436 | M192Q + L260P + R336L + D379V + R454A + E457L | L181F + A237V + R480K and/or G413L/S + H416D + E418A |
| DS437 | M192Q + L260P + R336L + D379V + R454A + E457N | L181F + A237V + R480K and/or G413L/S + H416D + E418A |
| DS438 | M192Q + L260P + R336L + D379V + R454A | L181F + A237V + R480K and/or G413L/S + H416D + E418A |
| DS439 | M192Q + L260P + R336L + D379V + E457L | L181F + A237V + R480K and/or G413L/S + H416D + E418A |
| DS440 | M192Q + L260P + R336L + D379V + E457N | L181F + A237V + R480K and/or G413L/S + H416D + E418A |
| DS441 | M192Q + L260P + R336L + D379V | L181F + A237V + R480K and/or G413L/S + H416D + E418A |
| DS442 | M192Q + L260P + R336L + R454P + E457L | L181F + A237V + R480K and/or G413L/S + H416D + E418A |
| DS443 | M192Q + L260P + R336L + R454P + E457N | L181F + A237V + R480K and/or G413L/S + H416D + E418A |
| DS444 | M192Q + L260P + R336L + R454P | L181F + A237V + R480K and/or G413L/S + H416D + E418A |
| DS445 | M192Q + L260P + R336L + R454A + E457L | L181F + A237V + R480K and/or G413L/S + H416D + E418A |
| DS446 | M192Q + L260P + R336L + R454A + E457N | L181F + A237V + R480K and/or G413L/S + H416D + E418A |
| DS447 | M192Q + L260P + R336L + R454A | L181F + A237V + R480K and/or G413L/S + H416D + E418A |
| DS448 | M192Q + L260P + R336L + E457L | L181F + A237V + R480K and/or G413L/S + H416D + E418A |
| DS449 | M192Q + L260P + R336L + E457N | L181F + A237V + R480K and/or G413L/S + H416D + E418A |
| DS450 | M192Q + L260P + R336L | L181F + A237V + R480K and/or G413L/S + H416D + E418A |
| DS451 | M192Q + L260P + R336N + D379V + R454P + E457L | L181F + A237V + R480K and/or G413L/S + H416D + E418A |
| DS452 | M192Q + L260P + R336N + D379V + R454P + E457N | L181F + A237V + R480K and/or G413L/S + H416D + E418A |
| DS453 | M192Q + L260P + R336N + D379V + R454P | L181F + A237V + R480K and/or G413L/S + H416D + E418A |
| DS454 | M192Q + L260P + R336N + D379V + R454A + E457L | L181F + A237V + R480K and/or G413L/S + H416D + E418A |
| DS455 | M192Q + L260P + R336N + D379V + R454A + E457N | L181F + A237V + R480K and/or G413L/S + H416D + E418A |
| DS456 | M192Q + L260P + R336N + D379V + R454A | L181F + A237V + R480K and/or G413L/S + H416D + E418A |
| DS457 | M192Q + L260P + R336N + D379V + E457L | L181F + A237V + R480K and/or G413L/S + H416D + E418A |
| DS458 | M192Q + L260P + R336N + D379V + E457N | L181F + A237V + R480K and/or G413L/S + H416D + E418A |
| DS459 | M192Q + L260P + R336N + D379V | L181F + A237V + R480K and/or G413L/S + H416D + E418A |

TABLE 2-continued

Variants of TdT having the amino acid sequence of SEQ ID N° 2

| Name | Variable Mutations | Optional Constant Mutations |
|---|---|---|
| DS460 | M1920 + L260P + R336N + R454P + E457L | L181F + A237V + R480K and/or G413L/S + H416D + E418A |
| DS461 | M1920 + L260P + R336N + R454P + E457N | L181F + A237V + R480K and/or G413L/S + H416D + E418A |
| DS462 | M1920 + L260P + R336N + R454P | L181F + A237V + R480K and/or G413L/S + H416D + E418A |
| DS463 | M1920 + L260P + R336N + R454A + E457L | L181F + A237V + R480K and/or G413L/S + H416D + E418A |
| DS464 | M1920 + L260P + R336N + R454A + E457N | L181F + A237V + R480K and/or G413L/S + H416D + E418A |
| DS465 | M1920 + L260P + R336N + R454A | L181F + A237V + R480K and/or G413L/S + H416D + E418A |
| DS466 | M1920 + L260P + R336N + E457L | L181F + A237V + R480K and/or G413L/S + H416D + E418A |
| DS467 | M1920 + L260P + R336N + E457N | L181F + A237V + R480K and/or G413L/S + H416D + E418A |
| DS468 | M1920 + L260P + R336N | L181F + A237V + R480K and/or G413L/S + H416D + E418A |
| DS469 | M1920 + L260P + D379V + R454P + E457L | L181F + A237V + R480K and/or G413L/S + H416D + E418A |
| DS470 | M1920 + L260P + D379V + R454P + E457N | L181F + A237V + R480K and/or G413L/S + H416D + E418A |
| DS471 | M1920 + L260P + D379V + R454P | L181F + A237V + R480K and/or G413L/S + H416D + E418A |
| DS472 | M1920 + L260P + D379V + R454A + E457L | L181F + A237V + R480K and/or G413L/S + H416D + E418A |
| DS473 | M1920 + L260P + D379V + R454A + E457N | L181F + A237V + R480K and/or G413L/S + H416D + E418A |
| DS474 | M1920 + L260P + D379V + R454A | L181F + A237V + R480K and/or G413L/S + H416D + E418A |
| DS475 | M1920 + L260P + D379V + E457L | L181F + A237V + R480K and/or G413L/S + H416D + E418A |
| DS476 | M1920 + L260P + D379V + E457N | L181F + A237V + R480K and/or G413L/S + H416D + E418A |
| DS477 | M1920 + L260P + D379V | L181F + A237V + R480K and/or G413L/S + H416D + E418A |
| DS478 | M1920 + L260P + R454P + E457L | L181F + A237V + R480K and/or G413L/S + H416D + E418A |
| DS479 | M1920 + L260P + R454P + E457N | L181F + A237V + R480K and/or G413L/S + H416D + E418A |
| DS480 | M1920 + L260P + R454P | L181F + A237V + R480K and/or G413L/S + H416D + E418A |
| DS481 | M1920 + L260P + R454A + E457L | L181F + A237V + R480K and/or G413L/S + H416D + E418A |
| DS482 | M1920 + L260P + R454A + E457N | L181F + A237V + R480K and/or G413L/S + H416D + E418A |
| DS483 | M1920 + L260P + R454A | L181F + A237V + R480K and/or G413L/S + H416D + E418A |
| DS484 | M1920 + L260P + E457L | L181F + A237V + R480K and/or G413L/S + H416D + E418A |
| DS485 | M1920 + L260P + E457N | L181F + A237V + R480K and/or G413L/S + H416D + E418A |
| DS486 | M1920 + L260P | L181F + A237V + R480K and/or G413L/S + H416D + E418A |
| DS595 | M1920 + R336L + D379V + R454P + E457L | L181F + A237V + R480K and/or G413L/S + H416D + E418A |
| DS596 | M1920 + R336L + D379V + R454P + E457N | L181F + A237V + R480K and/or G413L/S + H416D + E418A |
| DS597 | M1920 + R336L + D379V + R454P | L181F + A237V + R480K and/or G413L/S + H416D + E418A |
| DS598 | M1920 + R336L + D379V + R454A + E457L | L181F + A237V + R480K and/or G413L/S + H416D + E418A |
| DS599 | M1920 + R336L + D379V + R454A + E457N | L181F + A237V + R480K and/or G413L/S + H416D + E418A |
| DS600 | M1920 + R336L + D379V + R454A | L181F + A237V + R480K and/or G413L/S + H416D + E418A |
| DS601 | M1920 + R336L + D379V + E457L | L181F + A237V + R480K and/or G413L/S + H416D + E418A |
| DS602 | M1920 + R336L + D379V + E457N | L181F + A237V + R480K and/or G413L/S + H416D + E418A |
| DS603 | M1920 + R336L + D379V | L181F + A237V + R480K and/or G413L/S + H416D + E418A |
| DS604 | M1920 + R336L + R454P + E457L | L181F + A237V + R480K and/or G413L/S + H416D + E418A |
| DS605 | M1920 + R336L + R454P + E457N | L181F + A237V + R480K and/or G413L/S + H416D + E418A |
| DS606 | M1920 + R336L + R454P | L181F + A237V + R480K and/or G413L/S + H416D + E418A |
| DS607 | M1920 + R336L + R454A + E457L | L181F + A237V + R480K and/or G413L/S + H416D + E418A |
| DS608 | M1920 + R336L + R454A + E457N | L181F + A237V + R480K and/or G413L/S + H416D + E418A |
| DS609 | M1920 + R336L + R454A | L181F + A237V + R480K and/or G413L/S + H416D + E418A |
| DS610 | M1920 + R336L + E457L | L181F + A237V + R480K and/or G413L/S + H416D + E418A |
| DS611 | M1920 + R336L + E457N | L181F + A237V + R480K and/or G413L/S + H416D + E418A |
| DS612 | M1920 + R336L | L181F + A237V + R480K and/or G413L/S + H416D + E418A |
| DS613 | M1920 + R336N + D379V + R454P + E457L | L181F + A237V + R480K and/or G413L/S + H416D + E418A |
| DS614 | M1920 + R336N + D379V + R454P + E457N | L181F + A237V + R480K and/or G413L/S + H416D + E418A |
| DS615 | M1920 + R336N + D379V + R454P | L181F + A237V + R480K and/or G413L/S + H416D + E418A |
| DS616 | M1920 + R336N + D379V + R454A + E457L | L181F + A237V + R480K and/or G413L/S + H416D + E418A |
| DS617 | M1920 + R336N + D379V + R454A + E457N | L181F + A237V + R480K and/or G413L/S + H416D + E418A |
| DS618 | M1920 + R336N + D379V + R454A | L181F + A237V + R480K and/or G413L/S + H416D + E418A |
| DS619 | M1920 + R336N + D379V + E457L | L181F + A237V + R480K and/or G413L/S + H416D + E418A |
| DS620 | M1920 + R336N + D379V + E457N | L181F + A237V + R480K and/or G413L/S + H416D + E418A |
| DS621 | M1920 + R336N + D379V | L181F + A237V + R480K and/or G413L/S + H416D + E418A |
| DS622 | M1920 + R336N + R454P + E457L | L181F + A237V + R480K and/or G413L/S + H416D + E418A |
| DS623 | M1920 + R336N + R454P + E457N | L181F + A237V + R480K and/or G413L/S + H416D + E418A |
| DS624 | M1920 + R336N + R454P | L181F + A237V + R480K and/or G413L/S + H416D + E418A |
| DS625 | M1920 + R336N + R454A + E457L | L181F + A237V + R480K and/or G413L/S + H416D + E418A |
| DS626 | M1920 + R336N + R454A + E457N | L181F + A237V + R480K and/or G413L/S + H416D + E418A |
| DS627 | M1920 + R336N + R454A | L181F + A237V + R480K and/or G413L/S + H416D + E418A |
| DS628 | M1920 + R336N + E457L | L181F + A237V + R480K and/or G413L/S + H416D + E418A |
| DS629 | M1920 + R336N + E457N | L181F + A237V + R480K and/or G413L/S + H416D + E418A |
| DS630 | M1920 + R336N | L181F + A237V + R480K and/or G413L/S + H416D + E418A |
| DS631 | M1920 + D379V + R454P + E457L | L181F + A237V + R480K and/or G413L/S + H416D + E418A |
| DS632 | M1920 + D379V + R454P + E457N | L181F + A237V + R480K and/or G413L/S + H416D + E418A |
| DS633 | M1920 + D379V + R454P | L181F + A237V + R480K and/or G413L/S + H416D + E418A |
| DS634 | M1920 + D379V + R454A + E457L | L181F + A237V + R480K and/or G413L/S + H416D + E418A |
| DS635 | M1920 + D379V + R454A + E457N | L181F + A237V + R480K and/or G413L/S + H416D + E418A |
| DS636 | M1920 + D379V + R454A | L181F + A237V + R480K and/or G413L/S + H416D + E418A |
| DS637 | M1920 + D379V + E457L | L181F + A237V + R480K and/or G413L/S + H416D + E418A |
| DS638 | M1920 + D379V + E457N | L181F + A237V + R480K and/or G413L/S + H416D + E418A |
| DS639 | M1920 + D379V | L181F + A237V + R480K and/or G413L/S + H416D + E418A |
| DS640 | M1920 + R454P + E457L | L181F + A237V + R480K and/or G413L/S + H416D + E418A |
| DS641 | M1920 + R454P + E457N | L181F + A237V + R480K and/or G413L/S + H416D + E418A |
| DS642 | M1920 + R454P | L181F + A237V + R480K and/or G413L/S + H416D + E418A |
| DS643 | M1920 + R454A + E457L | L181F + A237V + R480K and/or G413L/S + H416D + E418A |

TABLE 2-continued

Variants of TdT having the amino acid sequence of SEQ ID N° 2

| Name | Variable Mutations | Optional Constant Mutations |
|---|---|---|
| DS644 | M1920 + R454A + E457N | L181F + A237V + R480K and/or G413L/S + H416D + E418A |
| DS645 | M1920 + R454A | L181F + A237V + R480K and/or G413L/S + H416D + E418A |
| DS646 | M1920 + E457L | L181F + A237V + R480K and/or G413L/S + H416D + E418A |
| DS647 | M1920 + E457N | L181F + A237V + R480K and/or G413L/S + H416D + E418A |
| DS648 | M1920 | L181F + A237V + R480K and/or G413L/S + H416D + E418A |
| DS757 | L260P + R336L + D379V + R454P + E457L | L181F + A237V + R480K and/or G413L/S + H416D + E418A |
| DS758 | L260P + R336L + D379V + R454P + E457N | L181F + A237V + R480K and/or G413L/S + H416D + E418A |
| DS759 | L260P + R336L + D379V + R454P | L181F + A237V + R480K and/or G413L/S + H416D + E418A |
| DS760 | L260P + R336L + D379V + R454A + E457L | L181F + A237V + R480K and/or G413L/S + H416D + E418A |
| DS761 | L260P + R336L + D379V + R454A + E457N | L181F + A237V + R480K and/or G413L/S + H416D + E418A |
| DS762 | L260P + R336L + D379V + R454A | L181F + A237V + R480K and/or G413L/S + H416D + E418A |
| DS763 | L260P + R336L + D379V + E457L | L181F + A237V + R480K and/or G413L/S + H416D + E418A |
| DS764 | L260P + R336L + D379V + E457N | L181F + A237V + R480K and/or G413L/S + H416D + E418A |
| DS765 | L260P + R336L + D379V | L181F + A237V + R480K and/or G413L/S + H416D + E418A |
| DS766 | L260P + R336L + R454P + E457L | L181F + A237V + R480K and/or G413L/S + H416D + E418A |
| DS767 | L260P + R336L + R454P + E457N | L181F + A237V + R480K and/or G413L/S + H416D + E418A |
| DS768 | L260P + R336L + R454P | L181F + A237V + R480K and/or G413L/S + H416D + E418A |
| DS769 | L260P + R336L + R454A + E457L | L181F + A237V + R480K and/or G413L/S + H416D + E418A |
| DS770 | L260P + R336L + R454A + E457N | L181F + A237V + R480K and/or G413L/S + H416D + E418A |
| DS771 | L260P + R336L + R454A | L181F + A237V + R480K and/or G413L/S + H416D + E418A |
| DS772 | L260P + R336L + E457L | L181F + A237V + R480K and/or G413L/S + H416D + E418A |
| DS773 | L260P + R336L + E457N | L181F + A237V + R480K and/or G413L/S + H416D + E418A |
| DS774 | L260P + R336L | L181F + A237V + R480K and/or G413L/S + H416D + E418A |
| DS775 | L260P + R336N + D379V + R454P + E457L | L181F + A237V + R480K and/or G413L/S + H416D + E418A |
| DS776 | L260P + R336N + D379V + R454P + E457N | L181F + A237V + R480K and/or G413L/S + H416D + E418A |
| DS777 | L260P + R336N + D379V + R454P | L181F + A237V + R480K and/or G413L/S + H416D + E418A |
| DS778 | L260P + R336N + D379V + R454A + E457L | L181F + A237V + R480K and/or G413L/S + H416D + E418A |
| DS779 | L260P + R336N + D379V + R454A + E457N | L181F + A237V + R480K and/or G413L/S + H416D + E418A |
| DS780 | L260P + R336N + D379V + R454A | L181F + A237V + R480K and/or G413L/S + H416D + E418A |
| DS781 | L260P + R336N + D379V + E457L | L181F + A237V + R480K and/or G413L/S + H416D + E418A |
| DS782 | L260P + R336N + D379V + E457N | L181F + A237V + R480K and/or G413L/S + H416D + E418A |
| DS783 | L260P + R336N + D379V | L181F + A237V + R480K and/or G413L/S + H416D + E418A |
| DS784 | L260P + R336N + R454P + E457L | L181F + A237V + R480K and/or G413L/S + H416D + E418A |
| DS785 | L260P + R336N + R454P + E457N | L181F + A237V + R480K and/or G413L/S + H416D + E418A |
| DS786 | L260P + R336N + R454P | L181F + A237V + R480K and/or G413L/S + H416D + E418A |
| DS787 | L260P + R336N + R454A + E457L | L181F + A237V + R480K and/or G413L/S + H416D + E418A |
| DS788 | L260P + R336N + R454A + E457N | L181F + A237V + R480K and/or G413L/S + H416D + E418A |
| DS789 | L260P + R336N + R454A | L181F + A237V + R480K and/or G413L/S + H416D + E418A |
| DS790 | L260P + R336N + E457L | L181F + A237V + R480K and/or G413L/S + H416D + E418A |
| DS791 | L260P + R336N + E457N | L181F + A237V + R480K and/or G413L/S + H416D + E418A |
| DS792 | L260P + R336N | L181F + A237V + R480K and/or G413L/S + H416D + E418A |
| DS793 | L260P + D379V + R454P + E457L | L181F + A237V + R480K and/or G413L/S + H416D + E418A |
| DS794 | L260P + D379V + R454P + E457N | L181F + A237V + R480K and/or G413L/S + H416D + E418A |
| DS795 | L260P + D379V + R454P | L181F + A237V + R480K and/or G413L/S + H416D + E418A |
| DS796 | L260P + D379V + R454A + E457L | L181F + A237V + R480K and/or G413L/S + H416D + E418A |
| DS797 | L260P + D379V + R454A + E457N | L181F + A237V + R480K and/or G413L/S + H416D + E418A |
| DS798 | L260P + D379V + R454A | L181F + A237V + R480K and/or G413L/S + H416D + E418A |
| DS799 | L260P + D379V + E457L | L181F + A237V + R480K and/or G413L/S + H416D + E418A |
| DS800 | L260P + D379V + E457N | L181F + A237V + R480K and/or G413L/S + H416D + E418A |
| DS801 | L260P + D379V | L181F + A237V + R480K and/or G413L/S + H416D + E418A |
| DS802 | L260P + R454P + E457L | L181F + A237V + R480K and/or G413L/S + H416D + E418A |
| DS803 | L260P + R454P + E457N | L181F + A237V + R480K and/or G413L/S + H416D + E418A |
| DS804 | L260P + R454P | L181F + A237V + R480K and/or G413L/S + H416D + E418A |
| DS805 | L260P + R454A + E457L | L181F + A237V + R480K and/or G413L/S + H416D + E418A |
| DS806 | L260P + R454A + E457N | L181F + A237V + R480K and/or G413L/S + H416D + E418A |
| DS807 | L260P + R454A | L181F + A237V + R480K and/or G413L/S + H416D + E418A |
| DS808 | L260P + E457L | L181F + A237V + R480K and/or G413L/S + H416D + E418A |
| DS809 | L260P + E457N | L181F + A237V + R480K and/or G413L/S + H416D + E418A |
| DS810 | L260P | L181F + A237V + R480K and/or G413L/S + H416D + E418A |
| DS921 | R336L + D379V + R454P | L181F + A237V + R480K and/or G413L/S + H416D + E418A |
| DS922 | R336L + D379V + R454A + E457L | L181F + A237V + R480K and/or G413L/S + H416D + E418A |
| DS923 | R336L + D379V + R454A + E457N | L181F + A237V + R480K and/or G413L/S + H416D + E418A |
| DS924 | R336L + D379V + R454A | L181F + A237V + R480K and/or G413L/S + H416D + E418A |
| DS925 | R336L + D379V + E457L | L181F + A237V + R480K and/or G413L/S + H416D + E418A |
| DS926 | R336L + D379V + E457N | L181F + A237V + R480K and/or G413L/S + H416D + E418A |
| DS927 | R336L + D379V | L181F + A237V + R480K and/or G413L/S + H416D + E418A |
| DS928 | R336L + R454P + E457L | L181F + A237V + R480K and/or G413L/S + H416D + E418A |
| DS929 | R336L + R454P + E457N | L181F + A237V + R480K and/or G413L/S + H416D + E418A |
| DS930 | R336L + R454P | L181F + A237V + R480K and/or G413L/S + H416D + E418A |
| DS931 | R336L + R454A + E457L | L181F + A237V + R480K and/or G413L/S + H416D + E418A |
| DS932 | R336L + R454A + E457N | L181F + A237V + R480K and/or G413L/S + H416D + E418A |
| DS933 | R336L + R454A | L181F + A237V + R480K and/or G413L/S + H416D + E418A |
| DS934 | R336L + E457L | L181F + A237V + R480K and/or G413L/S + H416D + E418A |
| DS935 | R336L + E457N | L181F + A237V + R480K and/or G413L/S + H416D + E418A |
| DS936 | R336L | L181F + A237V + R480K and/or G413L/S + H416D + E418A |
| DS937 | R336N + D379V + R454P + E457L | L181F + A237V + R480K and/or G413L/S + H416D + E418A |

TABLE 2-continued

Variants of TdT having the amino acid sequence of SEQ ID N° 2

| Name | Variable Mutations | Optional Constant Mutations |
|---|---|---|
| DS938 | R336N + D379V + R454P + E457N | L181F + A237V + R480K and/or G413L/S + H416D + E418A |
| DS939 | R336N + D379V + R454P | L181F + A237V + R480K and/or G413L/S + H416D + E418A |
| DS940 | R336N + D379V + R454A + E457L | L181F + A237V + R480K and/or G413L/S + H416D + E418A |
| DS941 | R336N + D379V + R454A + E457N | L181F + A237V + R480K and/or G413L/S + H416D + E418A |
| DS942 | R336N + D379V + R454A | L181F + A237V + R480K and/or G413L/S + H416D + E418A |
| DS943 | R336N + D379V + E457L | L181F + A237V + R480K and/or G413L/S + H416D + E418A |
| DS944 | R336N + D379V + E457N | L181F + A237V + R480K and/or G413L/S + H416D + E418A |
| DS945 | R336N + D379V | L181F + A237V + R480K and/or G413L/S + H416D + E418A |
| DS946 | R336N + R454P + E457L | L181F + A237V + R480K and/or G413L/S + H416D + E418A |
| DS947 | R336N + R454P + E457N | L181F + A237V + R480K and/or G413L/S + H416D + E418A |
| DS948 | R336N + R454P | L181F + A237V + R480K and/or G413L/S + H416D + E418A |
| DS949 | R336N + R454A + E457L | L181F + A237V + R480K and/or G413L/S + H416D + E418A |
| DS950 | R336N + R454A + E457N | L181F + A237V + R480K and/or G413L/S + H416D + E418A |
| DS951 | R336N + R454A | L181F + A237V + R480K and/or G413L/S + H416D + E418A |
| DS952 | R336N + E457L | L181F + A237V + R480K and/or G413L/S + H416D + E418A |
| DS953 | R336N + E457N | L181F + A237V + R480K and/or G413L/S + H416D + E418A |
| DS954 | R336N | L181F + A237V + R480K and/or G413L/S + H416D + E418A |
| DS955 | D379V + R454P + E457L | L181F + A237V + R480K and/or G413L/S + H416D + E418A |
| DS956 | D379V + R454P + E457N | L181F + A237V + R480K and/or G413L/S + H416D + E418A |
| DS957 | D379V + R454P | L181F + A237V + R480K and/or G413L/S + H416D + E418A |
| DS958 | D379V + R454A + E457L | L181F + A237V + R480K and/or G413L/S + H416D + E418A |
| DS959 | D379V + R454A + E457N | L181F + A237V + R480K and/or G413L/S + H416D + E418A |
| DS960 | D379V + R454A | L181F + A237V + R480K and/or G413L/S + H416D + E418A |
| DS961 | D379V + E457L | L181F + A237V + R480K and/or G413L/S + H416D + E418A |
| DS962 | D379V + E457N | L181F + A237V + R480K and/or G413L/S + H416D + E418A |
| DS963 | D379V | L181F + A237V + R480K and/or G413L/S + H416D + E418A |
| DS964 | R454P + E457L | L181F + A237V + R480K and/or G413L/S + H416D + E418A |
| DS965 | R454P + E457N | L181F + A237V + R480K and/or G413L/S + H416D + E418A |
| DS966 | R454P | L181F + A237V + R480K and/or G413L/S + H416D + E418A |
| DS967 | R454A + E457L | L181F + A237V + R480K and/or G413L/S + H416D + E418A |
| DS968 | R454A + E457N | L181F + A237V + R480K and/or G413L/S + H416D + E418A |
| DS969 | R454A | L181F + A237V + R480K and/or G413L/S + H416D + E418A |
| DS970 | E457L | L181F + A237V + R480K and/or G413L/S + H416D + E418A |
| DS971 | E457N | L181F + A237V + R480K and/or G413L/S + H416D + E418A |
| DS919 | R336L + D379V + R454P + E457L | L181F + A237V + R480K and/or G413L/S + H416D + E418A |
| DS920 | R336L + D379V + R454P + E457N | L181F + A237V + R480K and/or G413L/S + H416D + E418A |

According to the invention, the variant of TdT has a substitution or combination of substitutions described above and at least 80% identity with SEQ ID N° 1 or functionally equivalent sequence, preferably at least 85%, 90%, 95%, 96%, 97%, 98%, or 99% identity with SEQ ID N° 1 or functionally equivalent sequence.

According to the invention, all variants of TdT as disclosed above are able to both synthesize a nucleic acid fragment without template and incorporate a modified nucleotide into the nucleic acid fragment. Advantageously, said variants have an increased ability to incorporate a modified nucleotide, preferably a 3'O-modified nucleotide, into a nucleic acid fragment as compared to a TdT of SEQ ID N° 1 or SEQ ID N° 2.

In some of the embodiments described above, the efficiency of a variant TdT in incorporating a 3'O-modified nucleoside triphosphate is at least 110 percent that of a wild type TdT of sequence SEQ ID NO: 1; in other embodiments, the efficiency of a variant TdT in incorporating a 3'O-modified nucleoside triphosphate is at least 150 percent that of a wild type TdT of sequence SEQ ID NO: 1; in other embodiments, the efficiency of a variant TdT in incorporating a 3'O-modified nucleoside triphosphate is at least 200 percent that of a wild type TdT of sequence SEQ ID NO: 1.

Additional Modifications

In an embodiment, the variant of TdT further includes any type of tagging peptide in its N-terminal, C-terminal or both extremity, such as a His-tag sequence. Said tagging peptide could be used for purification, identification, increasing expression, secretability or increasing catalytic activity. It will be understood that such different tags are extensively described in the literature and thus all tag known to a skilled person are covered by the present invention.

The variants of the invention can also include one or more exogenous or heterologous features at the N- and/or C-terminal regions of the protein for use, e.g., in the purification of the recombinant polymerase.

The variant of the invention may further comprise a substitution of residues between positions C378 to L406, wherein the positions are numbered by reference to the amino acid sequence set forth in SEQ ID N° 1, or functionally equivalent residues, by residues H363 to C390 of the Polμ polymerase of sequence SEQ ID N° 3, wherein the positions are numbered by reference to the amino acid sequence set forth in SEQ ID N° 3 or functionally equivalent residues.

Advantageously, the variant of TdT comprises at least the amino acid sequence SEQ ID N° 2 or functionally equivalent sequence, with the disclosed substitution(s). In a particular embodiment, the variant of TdT consists solely in the amino acid sequence of SEQ ID N° 2 (or functionally equivalent sequence) with the disclosed substitution(s). In another particular embodiment, the variant of TdT comprises at least the amino acid sequence SEQ ID N° 1 or functionally equivalent sequence, with the disclosed substitution(s) in SEQ ID N° 2. Preferably the variant has the amino acid sequence as set forth in SEQ ID N° 1, or functionally equivalent sequence, except full or part of the BRTC-like domain corresponding to residues 1 to 130 of SEQ ID N° 1.

Modified Nucleotides

According to the invention, the variants of TdT are able to incorporate modified nucleotides, preferably modified 3'O-nucleotides and more preferably 3'O-blocked nucleotides.

In the context of the invention, the expression "Modified Nucleotide" refers to a molecule containing a nucleoside (i.e. a base attached to a deoxyribose or ribose sugar molecule) bound to three phosphate groups which has at least one additional group on one of its extremity: 2', 3', 5' or base. Said additional group blocks further addition of nucleotides by preventing the formation of any phosphodiester bond (3'O-modification, 2' or 2'O modifications) or by sterically preventing the polymerase to attach to any nucleic acid fragments that comprises on its 3' extremity such modified nucleotide (5' or base modification). Furtherly, said additional group has advantageously a reversible nature allowing that group to be removed through a specific cleaving reaction.

Nucleosides or nucleotide triphosphates include deoxyadenosine triphosphate (dATP), deoxyguanosine triphosphate (dGTP), deoxycytidine triphosphate (dCTP) or deoxythymidine triphosphate (dTTP) for examples of nucleotide containing deoxyribose. Adenosine triphosphate (ATP), guanosine triphosphate (GTP), cytidine triphosphate (CTP) or uridine triphosphate (UTP) are further examples of nucleotide triphosphates containing ribose. Other types of nucleosides may be bound to three phosphates to form nucleotide triphosphates, such as naturally occurring modified nucleosides and artificial nucleosides.

In a particular embodiment, the modified nucleotide is a 3'O-blocked nucleotide, which comprises a group reversibly attached to the 3' end of the nucleotide triphosphate to prevent further nucleotide addition. Said group could have diverse chemical natures, such as azidomethyl, aminoxy, and allyl.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

wherein —Z is any of —C(R')2-0-R", —C(R')2-N(R")2, —C(R')2-N(H)R", —C(R')2-S—R" and —C(R')2-F, wherein each R" is or is part of a removable protecting group; each R is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')2 represents an alkylidene group of formula =C(R''')2 wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is —(R')2-F, the F is exchanged for OH, SH or NH2, preferably OH, which intermediate dissociates under aqueous conditions to afford a molecule with a free 3'-OH; with the proviso that where Z is —C(R')2-S—R", both R groups are not H. In certain embodiments, R of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, —Z of the modified nucleotide or nucleoside is of formula —C(R')2-N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less.

In a further particular embodiment, "3'O modified nucleotide" refers to nucleotide triphosphate bearing at the 3' extremity either a 3'-O-methyl, 3'-azido, 3'-O-azidomethyl, 3'-O-amino, 3'-aminoxy or 3'-O-allyl group. In a further embodiment, the 3'-blocked nucleotide triphosphate is blocked by either a 3'-O-azidomethyl, 3'-aminoxy or 3'-O-allyl group. In other embodiments, "3'O modified nucleotide" refers to nucleotide triphosphate bearing at the 3' extremity either esters, ethers, carbonitriles, phosphates, carbonates, carbamates, hydroxylamine, borates, nitrates, sugars, phosphoramide, phosphoramidates, phenylsulfenates, sulfates, sulfones or amino acids. In some embodiments, the foregoing 3'-O-blocking groups have a molecule weight of 100 or less.

In still other embodiments, 3'-O-blocking groups of the invention include methyl, 3'-O-(2-nitrobenzyl), allyl, amine, azidomethyl, tert-butoxy ethoxy, or propargyl.

In further particular embodiment, "3'O modified nucleotide" refers to a nucleotide triphosphate having a terminator effector modifying group such as those described in WO2016034807.

Interestingly, the variants of the invention exhibit an increased affinity for modified nucleotides, as compared to wild type TdT, and thereby an increased ability to incorporate such modified nucleotide in a nucleic acid sequence during nucleic acid synthesis. More particularly, the variants of the invention are able to use and incorporate modified 3'O-nucleotides (and more particularly, 3'O-blocked nucleotide) in nucleic acid sequence, which is not possible with wild type TdT (see Knapp et al. Chem. Eur. J., 2011, 17:2903).

According to a particular aspect, the invention relates to variants of TdT able to work with modified nucleotides in a nucleic acids enzymatic synthesis process, particularly with 3'O-modified nucleotides (e.g., 3'O-blocked nucleotide), and having the ability to produce long length nucleic acid molecules or derivative of nucleic acid molecules.

Enzymatic Synthesis of Nucleic Acid

It is the purpose of the present invention to provide variants of TdT that may be used for the synthesis of nucleic acid, such as described in Ybert et al, WO2015/159023; Jensen et al, Biochemistry, 57: 1821-1832 (2018); Hiatt et al, U.S. Pat. No. 5,808,045. More particularly, it is the purpose of the present invention to provide variants of TdT suitable to add modified nucleotides to an initiating nucleic acid strand. The blocking group may be then removed for allowing a new addition of modified nucleotide.

According to the invention, by use of a variant of the invention, it is possible to implement successive cycles comprising additions and deprotections. This process will therefore allow by multiple cycles of addition of a reversible modified nucleotide and further removal of the blocking group to allow the controlled extension of an initiating nucleic acid strand into a defined sequence.

The present invention contemplates the use of modified TdT according to the present invention in any enzymatic nucleic acid synthesis process.

It is also the purpose of the present invention to provide a process for synthesizing a nucleic acid molecule without template, comprising a step of contacting a nucleic acid primer with both at least one nucleotide, preferably at least one 3'O-modified nucleotide, and a variant of the invention.

The present invention contemplates the concept of enzymatic nucleic acids synthesis process. In such process, nucleic acids molecules are de novo synthesized in absence of any template strand. Accordingly, ordered sequence of nucleotides are coupled to an initiating fragment nucleic acid fragment with the help of the variant of the invention. It will be understood that quantitative coupling and more generally high coupling efficiency of each nucleotide to the growing nucleic acid chain is of great importance. It will also be understood that non-terminator nucleotides, such as natural nucleotides or permanent labeled nucleotides, will not permit any control over the sequence synthesized and will result, for example, in uncontrolled and undesired poly-additions.

According to a particular embodiment, the enzymatic nucleic acid synthesis process comprises:
a. Providing a nucleic acid molecule linked to a solid support;
b. Reacting previous nucleic acid molecule with a reversible terminator modified nucleotide and a variant of TdT according to the present invention;

According to another particular embodiment, the enzymatic nucleic acid process comprises:
a. Providing a nucleic acid molecule linked to a solid support;
b. Adding a reversible modified nucleotide and a variant of TdT according to the present invention;
c. First removing of one or several reagents from the solid support;
d. Reacting the reversible moiety of the reversible modified nucleotide in order to deprotect it for further subsequent elongation;
e. Second removing of one or several reagents from the solid support;
f. Optionally and finally cleaving the nucleic acid molecule from the solid support.

According to another particular embodiment, the enzymatic nucleic acid process comprise cycles subdivided in the following way:
a. A phase of elongation of Xi nucleotides to one end of said fragments, it being possible for X to be between 1 and 5, preferably between 1 and 3, i being the number of the cycle, making it possible to obtain fragments comprising n+Xi nucleotides, known as first phase, and comprising the following stages:
  a first stage of attaching, to a first support, a first end of initial nucleic acid fragments or nucleic acid fragments in the course of elongation, including n nucleotides,
  a stage of addition of the reagents necessary for the variant of TdT,
  a stage of variant of TdT addition of Xi nucleotides to the second end of said nucleic acid fragments, X being between 1 and 5, preferably 1 and 3, i being the number of the cycle,
  an optional stage of removal of the undesirable reagents from the reaction medium,
  a stage of detaching, from said first support, said fragments comprising n+Xi nucleotides,
  a first stage of transfer of said fragments comprising n+Xi nucleotides,
b. A phase of purification of the fragments having a correct sequence comprising n+Xi nucleotides, known as second phase, comprising the following successive stages:
  a second stage of attaching, to a second support, said fragments comprising n+Xi nucleotides by their end carrying the Xi nucleotides added during the first phase,
  a stage of removal of the fragments, which have not been attached to the second support,
  a stage of detaching said fragments comprising n+Xi nucleotides from said second support,
  an optional stage of removal, from the reaction medium, of the undesirable residual reagents;
c. An optional phase of amplification, preferably enzymatic amplification, such as by PCR, of the fragments having a correct sequence comprising n+Xi nucleotides, known as third phase, comprising the following successive stages:
  a stage of addition of the reagents necessary for the amplification,
  a stage (optionally composed of substages making the process possible) of multiplication by a multiplication factor Yi of the fragments comprising n+Xi nucleotides, i being the cycle number, it being possible for Y to be between 1 and $4 \times 10^{10}$, preferably between 1 and $1 \times 10^9$,
  a stage of transfer of the fragments comprising n+Xi nucleotides,
  each cycle being carried out in a reaction medium compatible with an enzymatic addition and an enzymatic amplification, such as an aqueous medium, the synthesis process also comprising, at the end of all of the i elongation cycles, a stage of final amplification by a multiplication factor Yf.

In some embodiments, the method of synthesizing a polynucleotide comprises the steps of (a) providing an initiating fragment having a free 3'-hydroxyl; (b) reacting under extension conditions the initiating fragment or an extension intermediate having a free 3'-hydroxyl with a variant TdT of the invention in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized.

In some embodiments, the method of synthesizing a polynucleotide comprises the steps of (a) providing an initiating fragment attached to a solid support, the initiator being an oligonucleotide having a free 3'-hydroxyl; (b) reacting under extension conditions the initiating fragment or an extension intermediate having a free 3'-hydroxyl with a variant TdT of the invention in the presence of a 3'-O-blocked nucleoside triphosphate to produce a 3'-O-blocked extension intermediate; (c) washing the solid support to remove unincorporated 3'-O-blocked nucleoside triphosphate; (d) deblocking the extension intermediate by exposing the solid support to a deblocking agent to produce an extension intermediate having a free 3'-hydroxyl; and (e) repeating steps (b) and (d) until the polynucleotide is synthesized. The method may include a further step of cleaving the completed polynucleotide from the solid support.

In some embodiments, for step (b), TdT catalyzed addition reactions, the enzymatic conditions may contain from about 0.20 and about 200 µM of the nucleotide having the removable blocking moiety protecting the 3'-hydroxyl and from about 0.20 to 200 μM of free and unmodified 3'-hydroxyls derived from the initiating substrate. In some embodiments, the reaction buffer contains from about 10 to about 500 mM potassium cacodylate buffer (pH between 6.5 and 7.5). and from about 0.01 to about 10 mM of a divalent cation (e.g. $CoCl_2$ or $MnCl_2$). Other buffer compositions and components may be suitable for particular desired embodiment of the present invention.

In the context of the invention, the expression "cleaving reaction" refers to any action of substance or physical conditions, which is able to cleave the additional group previously described on reversible modified nucleotides. A person skilled in the art is able to determine a cleaving reaction for any previously listed group.

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For example, tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiment, the cleaving reaction is involving: TCEP, a palladium complex or sodium nitrite.

In particular embodiment, the cleaving reaction is performed in the presence of additional components such as denaturant (urea, guanidinium chloride, formamide or betaine for example). In a further embodiment, the cleavage reaction is performed with one or more buffers. It will be understood by the person skilled in the art that the choice of buffer is dependent on the exact mechanism of reaction.

The present invention relates to variants of TdT with the capacity to incorporate, in a quantitative way, modified nucleotides. By "quantitative way" or "quantitative reaction", it is meant a reaction that goes to completion, i.e. in which reactants are totally converted into the product. Polymerase that incorporates in a quantitative way reversible modified nucleotide is a polymerase able to elongate every fragment of nucleic acid with all the nucleotides available leading to the conversion of all the initiating fragments of length n, to fragments of length n+1.

As used herein, "initiating fragment" refers to a short oligonucleotide sequence with a free 3'-end, which can be further elongated. In one embodiment, the initiating fragment is a DNA initiating fragment. In an alternative embodiment, the initiating fragment is an RNA initiating fragment.

In one embodiment, the initiating fragment possesses between 3 and 100 nucleotides, in particular between 3 and 20 nucleotides.

In one embodiment, the initiating fragment is single-stranded. In an alternative embodiment, the initiating fragment is double-stranded.

In one embodiment, the initiating fragment is immobilized on a solid support. The initiating fragment may be attached with various method to a solid support resulting in a stable under the various enzymatic or synthesis reaction conditions that the fragment will undergo.

In one embodiment, the initiating fragment is immobilized on a solid support via a reversible interacting moiety, such as a chemically-cleavable linker, an antibody/immunogenic epitope, a biotin/biotin-binding protein or glutathione-GST tag. In a further embodiment, the initiating fragment is immobilized on a solid support via a chemically-cleavable linker, such as a disulfide, allyl, or azide-masked hemiaminal ether linker.

In an initiating fragment, the immobilized part contains at least one restriction site. The use of restriction enzymes and restriction sites to selectively hydrolyze nucleic acids chain at a specific site is describe in the literature. Any skilled person will be able to choose the appropriate restriction enzyme that will match the initiating fragment cleaving site sequence.

In an alternative embodiment, the initiating fragment contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Nucleic Acid Molecules

It is also the purpose of the invention to provide a nucleic acid molecule encoding a variant of the invention. As used herein, a "nucleic acid molecule" refers to a polymer of nucleosides. In one embodiment, the nucleic acid is a DNA. In an alternative embodiment, the nucleic acid is RNA. In an alternative embodiment, the nucleic acid is XNA.

It will be understood by a skilled person that each of the previously listed nucleic acid molecules could bear modification on the bases of the nucleotides that constitute the polymeric molecule.

Such modifications could be natural modifications such as epigenetic modifications, or unnatural modification such as labels.

In one embodiment, nucleic acid molecules are DNA, RNA or XNA bearing naturally occurring epigenetic modifications such as methylation, hydfroxymethylation, formylation or 5-carboxylation.

In one embodiment, nucleic acid molecules are DNA, RNA or XNA bearing unnaturally occurring modifications such as fluorescent tag, fluorescent label, interaction groups.

In one embodiment, nucleic acid molecules are polymeric molecules having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

Applications

Described herein is the use of variants of TdT to be used for nucleic acid synthesis, oligonucleotide synthesis, probe synthesis, tagging, nucleic acid amplification, aptamers, therapeutic nucleic acid molecules, drug target discovery and validation, disease diagnosis, metabolic engineering, data storage, crops improvement, library design, sequencing pools, nucleic acid labeling or attachment or any other application that is involving nucleic acid molecules. Production of Variant TdTs Variants of the invention may be produced by mutating known reference or wild type TdT-coding polynucleotides, then expressing it using conventional molecular biology techniques. For example, the mouse TdT gene (SEQ ID NO: 1) may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or it may be directly cloned from mouse cells using protocols described by Boule et al, Mol. Biotechnology, 10: 199-208 (1998), or Bentolila et al, EMBO J., 14: 4221-4229 (1995); or the like.

For example, an isolated TdT gene may be inserted into an expression vector, such as pET32 (Novagen) to give a vector pCTdT which then may be used to make and express variant TdT proteins using conventional protocols. Vectors with the correct sequence may be transformed in *E. coli* producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 µm filter to remove any debris before column purification.

TdT protein may be purified from the centrifugate in a one-step affinity procedure. For example, Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDSPAGE gels.

Kits, Enzyme and Nucleotide Composition

A particular aspect of the invention is relative to the composition and the use of kits comprising a variant of TdT according to the invention, or to any particular aspect of the present invention, with optionally any combination of one or more components selected from: an initiating fragment, one or more reversible terminator nucleotides, additional enzyme and reagents used in a cleaving reaction. Said kits can be used in a method of enzymatic nucleic acid synthesis.

The present invention covers the composition of matter comprising variants of TdT according to the invention, or to any particular aspect of the present invention, with reversible modified nucleotide in a mix with appropriate buffer and ratio concentration.

EXAMPLES

Example 1—Generation, Expression and Purification of Variants of TdT According to the Invention Expression Strain Generation The TdT mouse gene has been generated from the pET28 plasmid described in [Boule et al., 1998, Mol. Biotechnol. 10, 199-208]. Sequence SEQ ID N° 4 (Tag TdT) has been amplified by using the following primers:
T7-pro: TAATACGACTCACTATAGGG (SEQ ID N° 5)
T7-ter: GCTAGTTATTGCTCAGCGG (SEQ ID N° 6)

through standard molecular biology techniques. The sequence is then cloned into plasmid pET32 backbone to give the new pCTdT plasmid.

After sequencing pCTdT is transformed into commercial E. coli cells, BL21 (DE3, from Novagen). Growing colonies on plate with kanamycin are isolated and named Ec-CTdT.

Polymerase Variants Generation

The pCTdT vector is used as starting vector. Specific primers comprising one or several point mutations have been generated from Agilent online software (http://www.genomics.agilent.com:80/primerDesignProgram.jsp). The commercially available kit QuickChange II (Agilent) has been used to generate the desired modified polymerase comprising the targeted mutations. Experimental procedure has followed the supplier's protocol. The resulting plasmids coding for the DSi or DSi' variants are named pDSi or pDSi', where i is the variant number given in Table 1 or Table 2. After generation of the different pDSi or pDSi' vectors, each of them have been sequenced. Vectors with the correct sequence have been transformed in E. coli producer strains, as described before. Clones able to grow on kanamycin LB-agar plates are isolated and name Ec-DSi or Ec-DSi'.

Expression

The Ec-CTdT and Ec-DSi or Ec-DSi' strains have been used for inoculating 250 mL erlens with 50 mL of LB media supplemented with appropriate amount of kanamycin. After overnight growth at 37° C., appropriate volumes of these pre-cultures have been used to inoculate 5 L erlens with 2 L LB media with kanamycin. The initial OD for the 5 L cultures is chosen to be 0.01. The erlens are put at 37° C. under strong agitation and the OD of the different cultures are regularly checked. After reaching an OD comprised between 0.6 and 0.9 each erlen is supplemented by the addition of 1 mL of 1M IPTG (Isopropyl β-D-1-thiogalactopyranoside, Sigma). The erlens are put back to agitation under a controlled temperature of 37° C. After overnight expression, the cells are harvested in several pellets. Pellets expressing the same variants are pooled and stored at −20° C., eventually for several months.

Extraction

Previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1h30 at 10,000 rpm. Centrifugate is pass through a 0.2 µm filter to remove any debris before column purification.

Purification

A one-step affinity procedure is used to purify the produced and extracted polymerase enzymes. A Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH$_4$]$_2$SO$_4$). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDS-PAGE gels.

Results are presented by FIG. 1. The gel shows, for each TdT (both variants and wild-type), the column flowthrough (FT) and the different fractions F1 to F4, corresponding to the elution peaks. A molecular weight marker (M) was also loaded in the gel. FIG. 1 shows that the variants of TdT according to the invention present a high purity level (about 90%) and a good expression as compared to TdT wild-type (see columns F2 and/or F3).

Example 2—Evaluation of the Activity of Variants of TdT with Fluorescent Primers Activity Test Elongation performance of variants DS11 DS29, DS173, DS659, DS874 from table 1 generated, expressed and purified according to example 1 is evaluated through the following assay. All the results are compared with each other and with the wild type TdT enzyme (SEQ ID N° 1) and to a control tube lacking any polymerase enzyme.

TABLE 3

| Activity test | | |
|---|---|---|
| Reagent | Concentration | Volume |
| H$_2$O | — | 12 µL |
| Activity Buffer | 10× | 2 µL |
| dNTP | 250 µM | 2 µL |
| Purified enzyme | 20 µM | 2 µL |
| Fluorescent primer DNA | 500 nM | 2 µL |

The Activity buffer comprises, for example, TdT reaction buffer (available from New England Biolabs) supplemented with CoCl$_2$. Primer used is the following:

5'-AAAAAAAAAAAAAAGGGG-3' (SEQ ID N° 7)

The primer has also an ATTO fluorescent dye on the 5' extremity.

Nucleotides used (noted as dNTP in table 3) are 3'-O-amino-2',3'-dideoxynucleotides-5'-triphosphate (ONH$_2$, Firebird Biosciences) such as 3'-O-amino-2',3'-dideoxyadenosine-5'-triphosphate for example.

For each different variant tested, one tube is used for the reaction. The reagents are added in the tube, starting from water, and then in the order of Table 3. After 30 min at 37° C. the reaction is stopped by addition of formamide (Sigma).

Analysis

The analysis is involving polyacrylamide gel analysis. Samples from activity test are analyzed through polyacrylamide 16% (biorad) denaturing gel. Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A tension of 500 to 2,000V is applied between the top and bottom of the gel for 3 to 6h at room temperature. Once migrated according to the sample target size, system is dismounted, and gel fluorescence is scanned through the use of Typhoon instrument (GE Life Sciences). After image acquisition, ImageJ software (image-j.nih.gov/ij/) is used to analyze the percentage of incorporation of the modified nucleotides.

Figure 2:
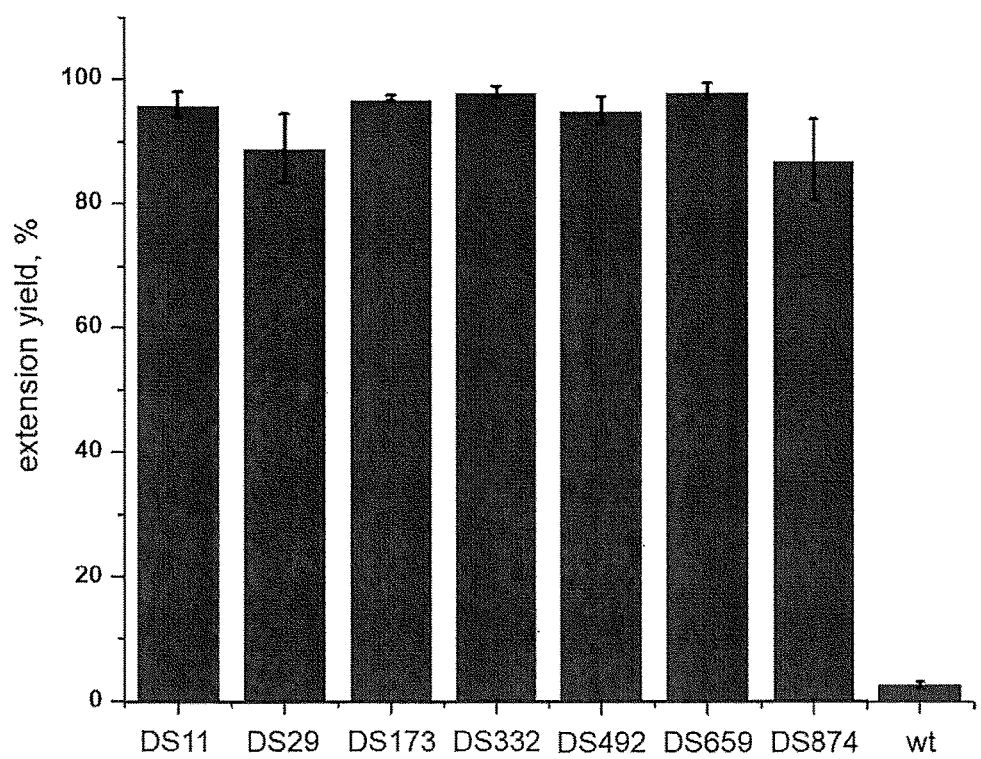
FIG. 2: Comparative results of performances for an elongation assay using wt TdT and TdT variants of the invention. The assay involves fluorescent labeled primers and 3'-O-amino reversible terminator modified nucleotides. The results represent mean value of n=3 experiments for each enzyme.

Results are showed on FIG. 2. For each variant, on the x-axis, the extension percentage has been evaluated as the quantity of expected elongated product over the total quantity of DNA loaded on the gel. Each experiment has been performed in triplicates. The bar height, y-axis, corresponds to the mean value of those three experiments. All the variants according to the invention show more than a 10-fold increase of activity compared to the wt enzyme, confirming the possibility of developing a nucleic acid synthesis technology with these variants.

Example 3—Evaluation of the Activity of Variants of TdT with Unlabeled Primer

Activity Test

Elongation performance of variants DS928 and DS950 from table 2 generated, expressed and purified according to example 1 was evaluated through the following assay. All the results are compared with a reference variant (SEQ ID N° 9) obtained from previous research and to a control tube lacking any polymerase enzyme.

TABLE 4

| Activity test | | |
|---|---|---|
| Reagent | Concentration | Volume |
| H$_2$O | — | 12 µL |
| Activity Buffer | 10× | 2 µL |
| dNTP | 250 µM | 2 µL |
| Purified enzyme | 20 µM | 2 µL |
| Fluorescent primer DNA | 500 nM | 2 µL |

Primer used is the following:
5'-TTTTTTTTTTTTAAATAAGG-3' (SEQ ID N° 8)

Nucleotides used (noted as dNTP in table 4) were 3'-O-amino-2',3'-dideoxynucleotides-5'-triphosphate (ONH2, Firebird Biosciences) such as 3'-O-amino-2',3'-dideoxyadenosine-5'-triphosphate for example.

For each variant tested one tube was used for the reaction. The reagents were added in the tube starting from the water and then in the order of Table 4. After 30 min at 37° C. the reaction was stopped by addition of formamide (Sigma).

Analysis

The analysis used liquid chromatography and mass spectrometer detection and quantification (LC/MS). Samples from activity test were analyzed through LC/MS. Samples were loaded into the LC/MS instrument and a standard oligonucleotide separation method was performed. Acquisition of data was followed by deconvolution and spectrum calculation.

Figure 3:
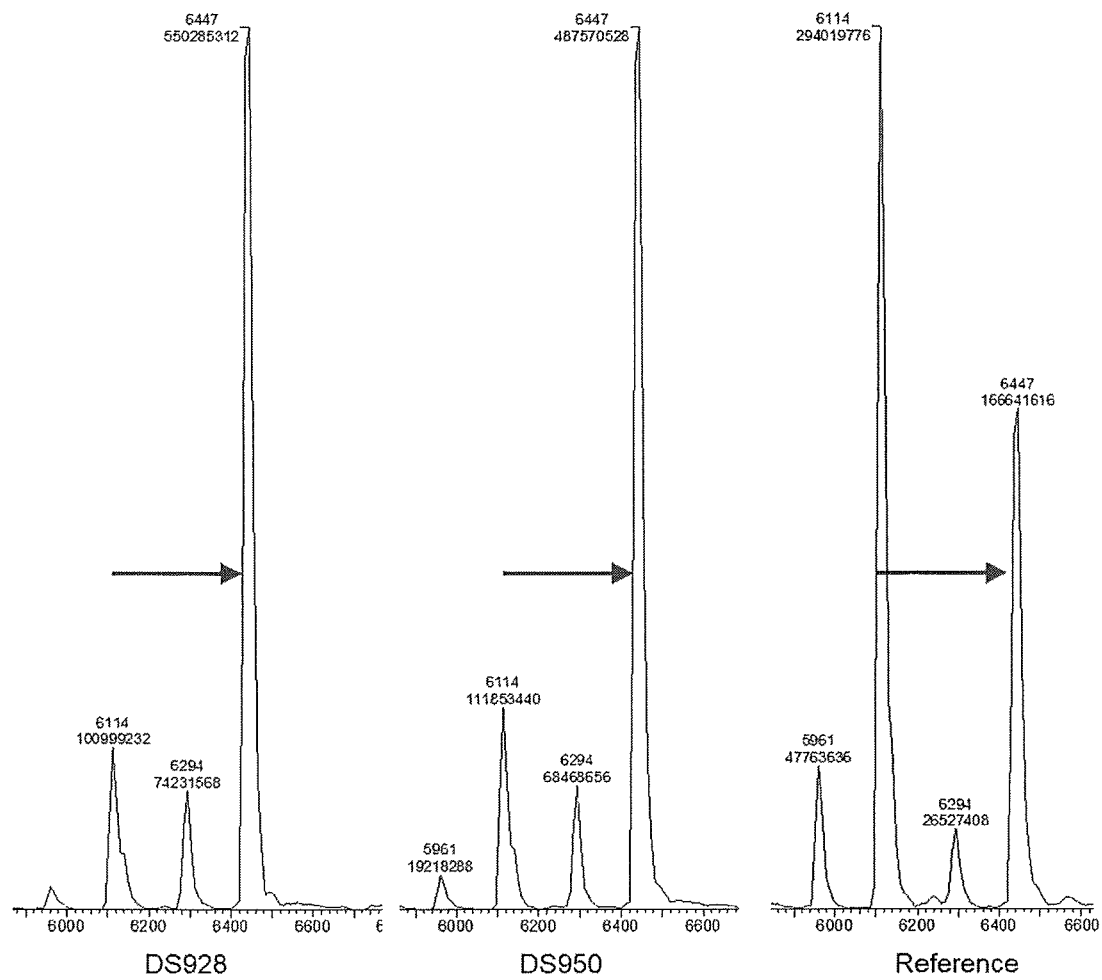
FIG. 3: Mass spectrum analysis of the results obtained for the elongation assay with different TdT variants of the invention. Only the relevant part of the mass spectrum is shown. The arrow shows the peak (mass) for the expected elongated primer.

Results are showed on FIG. 3. The spectrums correspond to the extension analysis of variants DS928, DS950 and references respectively. Initial primer mass is around 6114 and the expected extended product mass is around 6447 (emphasized by the arrows). The intensity of the signal (i.e., the height of the peaks) may be directly correlated to the quantity of material. Both variants DS928, DS950 show significant improvement in the elongation of the starting primer as compared to the reference variant. These results confirm that the new variants according to the invention bring indisputable improvement over the TdT of the prior art.

The invention claimed is:

1. A variant of Terminal deoxynucleotidyl Transferase (TdT) which (i) comprises amino acids 130 to 510 of the amino acid sequence as set forth in SEQ ID NO:1, with an amino acid substitution selected from C302G/R/P/A/N/S/N/Q/D, wherein the position is numbered by reference to the amino acid sequence set forth in SEQ ID NO:1, (ii) is capable of synthesizing a nucleic acid fragment without template and (iii) is capable of incorporating a modified nucleotide into the nucleic acid fragment.

2. The variant of TdT according to claim 1, wherein the variant further comprises at least two amino acid substitutions corresponding to residues selected from M192, L260, R336, D379, R454 and E457.

3. The variant of TdT according to claim 2, wherein the substitutions are selected from M192R/Q/G/A/V/D/N/H/E, L260P/M/E/N/F/K/D/A/G, R336N/L/K/H/G/D/A/P, D379V/A/G/N/E/R/H/K/T, R454P/N/A/L/K/H/G/D, and E457N/T/S/L/V/K/H/G/D.

4. The variant of TdT according to claim 2, wherein the substitution is selected from M192R/Q, L260P, R336L/N, D379V, R454P/N and E457N/L/T/S.

5. The variant of TdT according to claim 1, wherein the variant further comprises at least one substitution at position corresponding to residues selected from T340, G413, H416, E418, W450, and A510.

6. The variant of TdT according to claim 5, wherein the substitution is selected from T340S/N/Q/C/G/M/K/D, G413L/S/P/R, H416D, E418A/V, W450Y/F/P/L/I/V/A/G/E, and A510V/T/G.

7. The variant of TdT according to claim 1, wherein the variant further comprises at least one substitution at position corresponding to residues selected from L181, A237, L260, T340, G413, H416, E418, W450, R480 and A510.

8. The variant of TdT according to claim 7, wherein the substitution is selected from L181F+A237V+R480K and G413L/S+H416D+E418A.

9. The variant of TdT according to claim 1, wherein the variant further comprises at the N-terminal end or C-terminal end of SEQ ID NO:1 a tag-sequence.

10. The variant of TdT according to claim 1, wherein the tag-sequence is a His-tag sequence.

11. The variant of TdT according to claim 1, wherein the variant comprises at least a combination of substitution selected from the combinations of substitutions disclosed in table 1.

* * * * *

UNITED STATES PATENT AND TRADEMARK OFFICE
CERTIFICATE OF CORRECTION

PATENT NO. : 10,435,676 B2  
APPLICATION NO. : 16/242904  
DATED : October 8, 2019  
INVENTOR(S) : Elise Champion et al.

Page 1 of 1

It is certified that error appears in the above-identified patent and that said Letters Patent is hereby corrected as shown below:

In the Claims

In Claim 1, Column 61, Lines 44–45, please change "C302G/R/P/AN/S/N/O/D" to --C302G/R/P/A/V/S/N/Q/D--.

Signed and Sealed this
Twenty-third Day of June, 2020

Andrei Iancu
*Director of the United States Patent and Trademark Office*